United States Patent
Yu et al.

(10) Patent No.: US 10,556,951 B2
(45) Date of Patent: Feb. 11, 2020

(54) ANTI-CD33 ANTIBODIES AND IMMUNOCONJUGATES

(71) Applicant: GENENTECH, INC., South San Francisco, CA (US)

(72) Inventors: Shang-Fan Yu, Milpitas, CA (US); Wei-Ching Liang, Foster City, CA (US); Yan Wu, Foster City, CA (US); Steven Leong, Berkeley, CA (US); Andrew Polson, Berkeley, CA (US)

(73) Assignee: Genentech, Inc., South San Francisco, CA (US)

( * ) Notice: Subject to any disclaimer, the term of this patent is extended or adjusted under 35 U.S.C. 154(b) by 151 days.

(21) Appl. No.: 15/918,842

(22) Filed: Mar. 12, 2018

(65) Prior Publication Data

US 2018/0312586 A1    Nov. 1, 2018

Related U.S. Application Data

(60) Division of application No. 15/171,128, filed on Jun. 2, 2016, now Pat. No. 9,951,133, which is a continuation of application No. PCT/US2014/069874, filed on Dec. 12, 2014.

(60) Provisional application No. 61/916,087, filed on Dec. 13, 2013.

(51) Int. Cl.
| | |
|---|---|
| *A61K 39/395* | (2006.01) |
| *C07K 16/28* | (2006.01) |
| *G01N 33/574* | (2006.01) |
| *A61K 47/68* | (2017.01) |
| *A61K 39/00* | (2006.01) |

(52) U.S. Cl.
CPC ...... *C07K 16/2803* (2013.01); *A61K 47/6809* (2017.08); *A61K 47/6849* (2017.08); *G01N 33/57492* (2013.01); *A61K 2039/505* (2013.01); *C07K 2317/33* (2013.01); *C07K 2317/73* (2013.01); *C07K 2317/77* (2013.01); *C07K 2317/92* (2013.01); *G01N 2333/70596* (2013.01); *G01N 2458/00* (2013.01)

(58) Field of Classification Search
CPC .................................................. C07K 16/2803
See application file for complete search history.

(56) References Cited

U.S. PATENT DOCUMENTS

2014/0294868 A1    2/2014 Howard et al.

FOREIGN PATENT DOCUMENTS

| WO | WO 2004/043344 A2 | 5/2004 |
|---|---|---|
| WO | WO 2010/009124 A2 | 1/2010 |
| WO | WO 2011/130598 A1 | 10/2011 |
| WO | 2012/045752 A1 | 4/2012 |
| WO | 2013/173496 A2 | 11/2013 |
| WO | 2014/159981 A2 | 10/2014 |
| WO | 2014/160871 A2 | 10/2014 |
| WO | 2015/023355 A1 | 2/2015 |

OTHER PUBLICATIONS

Sgouros et al., "Pharmacokinetics and Dosimetry of an α-Particle Emitter Labeled Antibody: $^{213}$Bi-HuM195 (Anti-CD33) in Patients with Leukemia," J Nucl. Med., 40: 1935-1946 (1999).
Davis et al. "Glycosylation govern the binding of antipeptide antibodies to regions of hypervariable amino acid sequence within recombinant gb120 of human immunodeficiency virus type 1," *Journal of General Virology*, 71: 2889-2898 (1990).
Ruckwardt et al. "Sequence variation within the dominant amino terminus epitope affects antibody binding and neutralization of human immunodeficiency virus type 1 Tat protein," Journal of Virology 78(23): 13190-13196 (2004).
Notification of Transmittal of the International Search Report and the Written Opinion of the International Searching Authority, or the Declaration, pp. 12 (dated Mar. 11, 2015).

*Primary Examiner* — Sheela J. Huff
(74) *Attorney, Agent, or Firm* — McNeill Baur PLLC

(57) ABSTRACT

The invention provides anti-CD33 antibodies and immunoconjugates and methods of using the same.

39 Claims, 28 Drawing Sheets

Specification includes a Sequence Listing.

Light Chain Variable Region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7A1  | E | I | V | L | T | Q | S | P | L | S | L | P | V | T | P | G | E | P | A | S | I | S | C | R | S | S | Q | S | L | L | H | S | N | G | Y | N | Y | L | D | W | Y | L |
| 9C2  | D | V | V | M | T | Q | S | P | L | S | L | P | V | T | P | G | E | P | A | S | I | S | C | R | S | S | Q | S | L | L | H | S | N | G | Y | N | Y | L | D | W | Y | L |
| 10D3 | D | I | V | M | T | Q | S | P | L | S | L | P | V | T | P | G | E | P | A | S | I | S | C | R | S | S | Q | S | L | L | H | S | N | G | Y | N | Y | L | D | W | Y | L |
| 15G15 | E | I | V | L | T | Q | S | P | L | S | L | P | V | T | P | G | E | P | A | S | I | S | C | R | S | S | Q | S | L | L | H | S | N | G | Y | N | Y | L | D | W | Y | L |

CDR L1 - Contact: 30–36
CDR L1 - Chothia: 24–34
CDR L1 - Kabat: 24–34

| Kabat number | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7A1  | Q | Q | K | P | G | Q | S | P | Q | L | L | I | Y | L | G | S | N | R | A | S | G | V | P | D | R | F | S | G | S | G | S | G | T | D | F | T | L | K | I | S | R | V |
| 9C2  | Q | Q | K | P | G | Q | S | P | Q | L | L | I | Y | L | G | S | N | R | A | S | G | V | P | D | R | F | S | G | S | G | S | G | T | D | F | T | L | K | I | S | R | V |
| 10D3 | Q | Q | K | P | G | Q | S | P | Q | L | L | I | Y | L | G | S | N | R | A | S | G | V | P | D | R | F | S | G | S | G | S | G | T | D | F | T | L | K | I | S | R | V |
| 15G15 | Q | Q | K | P | G | Q | S | P | Q | L | L | I | Y | L | G | S | N | R | A | S | G | V | P | D | R | F | S | G | S | G | S | G | T | D | F | T | L | K | I | S | R | V |

CDR L2 - Contact: 46–55
CDR L2 - Chothia: 50–56
CDR L2 - Kabat: 50–56

| Kabat number | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|
| 7A1  | A | E | D | V | G | V | Y | Y | C | M | Q | A | L | Q | T | P | W | T | F | G | Q | G | T | K | V | E | I | K |
| 9C2  | A | E | D | V | G | V | Y | Y | C | M | Q | A | L | Q | T | P | W | T | F | G | Q | G | T | K | V | E | I | K |
| 10D3 | A | E | D | V | G | V | Y | Y | C | M | Q | A | L | Q | T | P | W | T | F | G | Q | G | T | K | V | E | I | K |
| 15G15 | A | E | D | V | G | V | Y | Y | C | M | Q | A | L | Q | T | P | W | T | F | G | Q | G | T | K | V | E | I | K |

CDR L3 - Contact: 89–96
CDR L3 - Chothia: 89–97
CDR L3 - Kabat: 89–97

FIG. 1A

Heavy Chain Variable Region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7A1 | Q | V | Q | L | V | Q | S | G | A | E | V | K | K | P | G | S | S | V | K | V | S | C | K | A | S | G | G | T | F | S | S | Y | A | V | S | W | V | R | Q | A | P | G |
| 9C2 | Q | V | Q | L | V | Q | S | G | A | E | V | K | K | P | G | S | S | V | K | V | S | C | K | A | S | G | G | T | F | S | S | Y | A | I | S | W | V | R | Q | A | P | G |
| 10D3 | E | V | Q | L | V | E | S | G | A | E | V | K | K | P | G | S | S | V | K | V | S | C | K | A | S | G | G | T | F | S | S | H | A | I | S | W | V | R | Q | A | P | G |
| 15G15 | Q | V | Q | L | V | Q | S | G | A | E | V | K | K | P | G | S | S | V | K | V | S | C | K | A | S | G | G | I | F | S | N | H | A | I | S | W | V | R | Q | A | P | G |

CDR H1 - Contact: 30-36
CDR H1 - Chothia: 26-32
CDR H1 - Kabat: 31-35

| Kabat number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7A1 | Q | G | L | E | W | M | G | G | I | I | P | I | F | G | T | A | D | Y | A | Q | K | F | Q | G | R | V | T | I | T | A | D | E | S | T | S | T | A | Y | M | E | L |
| 9C2 | Q | G | L | E | W | M | G | G | I | I | P | I | F | G | T | A | D | Y | A | Q | K | F | Q | G | R | V | T | I | T | A | D | E | S | T | S | T | A | Y | M | E | L |
| 10D3 | Q | G | L | E | W | M | G | G | I | I | P | I | F | G | A | A | N | Y | A | Q | K | F | Q | G | R | V | T | I | T | A | D | D | S | T | N | T | A | Y | L | E | L |
| 15G15 | Q | G | L | E | W | M | G | G | I | I | P | I | F | G | T | A | N | Y | A | Q | K | F | Q | G | R | V | T | I | T | A | D | E | S | T | S | T | A | F | M | E | L |

CDR H2 - Contact: 47-58
CDR H2 - Chothia: 50-56
CDR H2 - Kabat: 50-65

| Kabat number | 82b | 82c | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|
| 7A1 | S | L | R | S | E | D | T | A | V | Y | Y | Y | C | A | R | E | L | A | D | A | F | D | I | W | G | Q | G | T | M | V | T | V | S |
| 9C2 | S | L | R | S | E | D | T | A | V | Y | Y | Y | C | A | R | E | T | W | A | D | A | F | D | I | W | G | Q | G | T | M | V | T | V | S |
| 10D3 | S | L | R | S | E | D | T | A | V | Y | Y | Y | C | A | R | E | L | L | D | V | F | D | I | W | G | Q | G | T | T | V | T | V | S |
| 15G15 | S | L | R | S | E | D | T | A | V | Y | Y | Y | C | A | R | E | W | A | D | V | F | D | I | W | G | Q | G | T | M | V | T | V | S |

CDR H3 - Contact: 93-101
CDR H3 - Chothia: 95-102
CDR H3 - Kabat: 95-102

Light Chain Variable Region

| Kabat number | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|
| | | | | | | | | | | | | | | CDR L3 - Contact | | | | | | | | | | | | | |
| | | | | | | | | | | | | CDR L3 - Chothia | | | | | | | | | | | | | | | |
| | | | | | | | | | | | | CDR L3 - Kabat | | | | | | | | | | | | | | | |
| 15G15 | A | E | D | V | G | V | Y | Y | C | M | Q | A | L | Q | T | P | W | T | F | G | Q | G | T | K | V | E | I | K |
| 15G15.33 | A | E | D | V | G | V | Y | Y | C | M | Q | A | L | Q | T | P | W | T | F | G | Q | G | T | K | V | E | I | K |
| 15G15.37 | A | E | D | V | G | V | Y | Y | C | M | Q | A | L | Q | T | P | W | T | F | G | Q | G | T | K | V | E | I | K |
| 15G15.83 | A | E | D | V | G | V | Y | Y | C | M | Q | A | L | Q | T | P | W | T | F | G | Q | G | T | K | V | E | I | K |
| 15G15.88 | A | E | D | V | G | V | Y | Y | C | M | Q | A | L | Q | T | P | W | T | F | G | Q | G | T | K | V | E | I | K |
| 15G15.7 | A | E | D | V | G | V | Y | Y | C | M | Q | A | L | Q | T | P | W | T | F | G | Q | G | T | K | V | E | I | K |
| 15G15.17 | A | E | D | V | G | V | Y | Y | C | M | Q | A | L | Q | T | P | W | T | F | G | Q | G | T | K | V | E | I | K |
| 15G15.30 | A | E | D | V | G | V | Y | Y | C | M | Q | A | L | Q | T | P | W | T | F | G | Q | G | T | K | V | E | I | K |
| 15G15.31 | A | E | D | V | G | V | Y | Y | C | M | Q | A | L | Q | T | P | W | T | F | G | Q | G | T | K | V | E | I | K |
| 15G15.39 | A | E | D | V | G | V | Y | Y | C | M | Q | A | L | Q | T | P | W | T | F | G | Q | G | T | K | V | E | I | K |
| 15G15.84 | A | E | D | V | G | V | Y | Y | C | M | Q | A | L | Q | T | P | W | T | F | G | Q | G | T | K | V | E | I | K |

Heavy Chain Variable Region

| Kabat number | 82b | 82c | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|
| 15G15    | S | L | R | S | E | D | T | A | V | Y | Y | C | A | R | E | W | A | D | V | F | D | I | W | G | Q | G | T | M | V | T | V | S | S |
| 15G15.33 | S | L | R | S | E | D | T | A | V | Y | Y | C | A | R | E | W | A | D | V | F | D | I | W | G | Q | G | T | M | V | T | V | S | S |
| 15G15.37 | S | L | R | S | E | D | T | A | V | Y | Y | C | A | R | E | W | A | D | V | F | D | I | W | G | Q | G | T | M | V | T | V | S | S |
| 15G15.83 | S | L | R | S | E | D | T | A | V | Y | Y | C | A | R | E | W | A | D | V | F | D | I | W | G | Q | G | T | M | V | T | V | S | S |
| 15G15.88 | S | L | R | S | E | D | T | A | V | Y | Y | C | A | R | E | W | A | D | V | F | D | I | W | G | Q | G | T | M | V | T | V | S | S |
| 15G15.7  | S | L | R | S | E | D | T | A | V | Y | Y | C | A | R | E | W | A | D | V | F | D | I | W | G | Q | G | T | M | V | T | V | S | S |
| 15G15.17 | S | L | R | S | E | D | T | A | V | Y | Y | C | A | R | E | W | A | D | V | F | D | I | W | G | Q | G | T | M | V | T | V | S | S |
| 15G15.30 | S | L | R | S | E | D | T | A | V | Y | Y | C | A | R | E | W | A | D | V | F | D | I | W | G | Q | G | T | M | V | T | V | S | S |
| 15G15.31 | S | L | R | S | E | D | T | A | V | Y | Y | C | A | R | E | W | A | D | V | F | D | I | W | G | Q | G | T | M | V | T | V | S | S |
| 15G15.39 | S | L | R | S | E | D | T | A | V | Y | Y | C | A | R | E | W | A | D | V | F | D | I | W | G | Q | G | T | M | V | T | V | S | S |
| 15G15.84 | S | L | R | S | E | D | T | A | V | Y | Y | C | A | R | E | W | A | D | V | F | D | I | W | G | Q | G | T | M | V | T | V | S | S |

CDR H3 - Contact (positions 95–101)
CDR H3 - Chothia (positions 96–101)
CDR H3 - Kabat (positions 95–102)

Heavy Chain Variable Region

FIG. 3B

CDR H1 - Contact: positions 30-35
CDR H1 - Chothia: positions 26-32
CDR H1 - Kabat: positions 31-35

CDR H2 - Contact: positions 47-58
CDR H2 - Chothia: positions 52-56
CDR H2 - Kabat: positions 50-65

CDR H3 - Contact: positions 93-101
CDR H3 - Chothia: positions 95-102
CDR H3 - Kabat: positions 95-102

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 23E4 | E | V | Q | L | Q | Q | S | G | A | E | L | V | R | P | G | A | S | V | K | L | S | C | K | A | S | G | Y | T | F | T | N | Y | W | M | N | W | V | K | Q | R | P | G |
| 27C6 | E | V | Q | L | Q | Q | S | G | P | E | L | L | K | P | G | A | S | V | K | M | S | C | K | A | S | G | Y | A | F | T | S | Y | Y | M | H | W | V | K | Q | S | P | G |
| 33F3 | E | V | Q | L | Q | Q | S | G | P | E | L | V | K | P | G | A | S | V | K | M | S | C | K | A | S | G | Y | T | F | T | S | Y | Y | M | N | W | V | K | Q | S | H | G |
| 33F9 | E | V | Q | L | Q | Q | S | G | A | E | L | V | K | P | G | A | S | V | K | L | S | C | K | A | S | G | Y | T | F | T | S | Y | W | M | H | W | M | K | Q | R | P | G |
| 33H4 | E | V | Q | L | Q | Q | S | G | A | E | L | V | K | P | G | A | S | V | K | V | S | C | K | A | F | G | Y | T | F | T | P | I | E | W | M | K | Q | K | Q | K | H | G |

| Kabat number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 23E4 | Q | G | L | E | W | I | G | M | I | D | P | S | D | N | E | T | H | Y | S | Q | K | F | K | D | K | A | T | L | T | V | D | K | S | S | S | T | A | Y | M | Q | L | S |
| 27C6 | K | K | S | L | E | W | I | G | Y | I | D | P | Y | N | G | G | T | R | H | N | Q | K | F | K | G | K | A | T | L | T | V | D | K | S | S | S | T | A | Y | M | Q | L | S |
| 33F3 | K | S | L | E | W | I | G | Y | I | D | P | Y | N | G | D | T | K | Y | N | Q | K | F | K | G | K | A | T | L | T | V | D | K | S | S | S | T | A | Y | M | E | L | S |
| 33F9 | Q | G | L | E | W | I | G | Y | I | N | P | Y | N | D | G | T | K | Y | N | E | K | F | K | G | K | A | T | L | T | V | D | K | S | S | S | T | A | Y | M | E | L | L |
| 33H4 | K | S | L | E | W | I | G | E | I | H | P | Y | N | D | Q | I | K | Y | N | E | R | F | K | G | R | A | K | L | T | I | D | R | S | S | S | T | V | Y | L | E | L | G |

| Kabat number | 82b | 82c | 83 | 84 | 85 | 86 | 87 | 88 | 89 | 90 | 91 | 92 | 93 | 94 | 95 | 96 | 97 | 98 | 99 | 100 | 100a | 100b | 100c | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|
| 23E4 | S | L | T | S | E | D | S | A | V | Y | Y | C | A | G | S | Q | N | F | G | W | N | F | . | . | Y | Y | W | G | Q | G | T | L | V | T | V | S |
| 27C6 | S | L | T | S | E | D | S | A | V | Y | Y | C | A | R | . | . | . | . | . | . | . | . | . | D | Y | W | G | Q | G | T | T | V | T | V | S | S |
| 33F3 | S | L | T | S | E | D | S | A | V | Y | Y | C | A | R | G | Y | . | . | . | . | . | . | . | . | D | Y | W | G | Q | G | T | L | V | T | V | S |
| 33F9 | S | L | T | S | E | D | S | A | V | Y | Y | C | A | R | G | N | Y | Y | V | E | D | . | . | A | M | D | Y | W | G | Q | G | T | L | V | T | V | S |
| 33H4 | R | L | T | S | D | D | S | A | V | Y | Y | C | A | R | G | Y | Y | Y | Y | A | A | M | D | F | W | G | Q | G | T | T | V | T | V | S | S |

Light Chain Variable Region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9C3   | D | I | Q | M | T | Q | S | P | S | S | L | S | A | S | V | G | D | R | V | T | I | T | C | R | A | S | Q | G | I | R | N | D | L | G | W | Y | Q | Q | K | P | G | K |
| 9C3.2 | D | I | Q | M | T | Q | S | P | S | S | L | S | A | S | V | G | D | R | V | T | I | T | C | R | A | S | Q | G | I | R | N | D | L | G | W | Y | Q | Q | K | P | G | K |
| 9C3.3 | D | I | Q | M | T | Q | S | P | S | S | L | S | A | S | V | G | D | R | V | T | I | T | C | R | A | S | Q | G | I | R | N | D | L | G | W | Y | Q | Q | K | P | G | K |
| 9C3.4 | D | I | Q | M | T | Q | S | P | S | S | L | S | A | S | V | G | D | R | V | T | I | T | C | R | A | S | Q | G | I | R | N | D | L | G | W | Y | Q | Q | K | P | G | K |

CDR L1 – Contact: positions 24–34; CDR L1 – Chothia: 26–32; CDR L1 – Kabat: 24–34

| Kabat number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9C3   | A | P | K | K | L | L | I | Y | A | A | S | S | L | Q | S | G | V | P | S | R | F | T | G | S | G | S | G | T | E | F | T | L | T | I | S | S | L | Q | P | E | D | F |
| 9C3.2 | A | P | K | R | L | L | I | Y | A | A | S | S | L | Q | S | G | V | P | S | R | F | S | G | S | G | S | G | T | D | F | T | L | T | I | S | S | L | Q | P | E | D | F |
| 9C3.3 | A | P | K | R | L | L | I | Y | A | A | S | S | L | Q | S | G | V | P | S | R | F | S | G | S | G | S | G | T | D | F | T | L | T | I | S | S | L | Q | P | E | D | F |
| 9C3.4 | A | P | K | R | L | L | I | Y | A | A | S | S | L | Q | S | G | V | P | S | R | F | S | G | S | G | S | G | T | D | F | T | L | T | I | S | S | L | Q | P | E | D | F |

CDR L2 – Contact: 47–55; CDR L2 – Chothia: 50–56; CDR L2 – Kabat: 50–56

| Kabat number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|
| 9C3   | T | Y | Y | C | L | Q | H | N | S | Y | P | W | T | F | G | Q | G | T | K | L | E | I | K |
| 9C3.2 | T | Y | Y | C | L | Q | H | N | S | Y | P | W | T | F | G | Q | G | T | K | L | E | I | K |
| 9C3.3 | T | Y | Y | C | L | Q | H | N | S | Y | P | W | T | F | G | Q | G | T | K | L | E | I | K |
| 9C3.4 | T | Y | Y | C | L | Q | H | N | S | Y | P | W | T | F | G | Q | G | T | K | L | E | I | K |

CDR L3 – Contact: 89–96; CDR L3 – Chothia: 91–96; CDR L3 – Kabat: 89–97

*FIG. 4A*

Heavy Chain Variable Region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9C3   | E | V | Q | L | V | E | S | G | G | G | A | L | I | Q | P | G | G | S | L | R | L | S | C | V | A | S | G | F | T | I | S | G | N | Y | M | S | W | V | R | Q | A | P | G |
| 9C3.2 | E | V | Q | L | V | E | S | G | G | G | A | L | I | Q | P | G | G | S | L | R | L | S | C | V | A | S | G | F | T | I | S | G | N | Y | M | S | W | V | R | Q | A | P | G |
| 9C3.3 | E | V | Q | L | V | E | S | G | G | G | A | L | I | Q | P | G | G | S | L | R | L | S | C | V | A | S | G | F | T | I | S | G | N | Y | M | S | W | V | R | Q | A | P | G |
| 9C3.4 | E | V | Q | L | V | E | S | G | G | G | A | L | I | Q | P | G | G | S | L | R | L | S | C | V | A | S | G | F | T | I | S | G | N | Y | M | S | W | V | R | Q | A | P | G |

CDR H1 – Contact: positions 30–35; CDR H1 – Chothia: 26–32; CDR H1 – Kabat: 31–35

| Kabat number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a | 82b |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9C3   | K | G | L | E | W | V | S | L | I | Y | S | G | D | S | T | Y | Y | A | D | S | V | K | G | R | F | T | I | S | R | D | I | S | K | N | T | V | Y | L | Q | M | N | S |
| 9C3.2 | K | G | L | E | W | V | S | L | I | Y | S | G | D | S | T | Y | Y | A | D | S | V | K | G | R | F | T | I | S | R | D | I | S | K | N | T | V | Y | L | Q | M | N | S |
| 9C3.3 | K | G | L | E | W | V | S | L | I | Y | S | G | D | S | T | Y | Y | A | D | S | V | K | G | R | F | A | I | S | R | D | I | S | K | N | T | V | Y | L | Q | M | N | S |
| 9C3.4 | K | G | L | E | W | V | S | L | I | Y | S | G | D | S | T | Y | Y | A | D | S | V | K | G | R | F | A | I | S | R | D | I | S | K | N | T | V | Y | L | Q | M | N | S |

CDR H2 – Contact: positions 47–58; CDR H2 – Chothia: 52–56; CDR H2 – Kabat: 50–65

| Kabat number | 82c | 83 | 84 | 85 | 86 | 87 | 88 | 89 | 90 | 91 | 92 | 93 | 94 | 95 | 96 | 97 | 98 | 99 | 100 | 100a | 100b | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|
| 9C3   | L | R | V | E | D | T | A | V | Y | Y | C | V | R | R | D | G | Y | Y | Y | V | S | D | M | V | W | G | K | G | T | T | V | T | V | S |
| 9C3.2 | L | R | V | E | D | T | A | V | Y | Y | C | V | R | R | D | G | Y | Y | Y | V | S | D | M | V | W | G | K | G | T | T | V | T | V | S |
| 9C3.3 | L | R | A | E | D | T | A | V | Y | Y | C | V | R | R | D | G | Y | Y | Y | V | S | D | M | V | W | G | Q | G | T | T | V | T | V | S |
| 9C3.4 | L | R | A | E | D | T | A | V | Y | Y | C | V | R | R | D | G | Y | Y | Y | V | S | D | M | V | W | G | Q | G | T | T | V | T | V | S |

CDR H3 – Contact: positions 93–101; CDR H3 – Chothia / Kabat: 95–102

| Reference Ab | Binning Antibody | | | | | Reference Ab | Binning Antibody | | | | |
|---|---|---|---|---|---|---|---|---|---|---|---|
| | My9.6 | 27C6 | 23E4 | 33H4 | 33F9 | | 9C2 | 7A1 | 10D3 | 15G15 | Buffer |
| My9.6 | (−) | (+) | (+) | (+) | (−) | My9.6 | (−) | (−) | (−) | (−) | (−) |
| Different Epitope | | | | | | Different Epitope | | | | | |

FIG. 8D

| Reference Ab | Binning Antibody | | | | | Reference Ab | Binning Antibody | | | | |
|---|---|---|---|---|---|---|---|---|---|---|---|
| | My9.6 | 27C6 | 23E4 | 33H4 | 33F9 | | 9C2 | 7A1 | 10D3 | 15G15 | Buffer |
| 15G15 | (−) | (+) | (−) | (−) | (+) | 15G15 | (−) | (−) | (−) | (−) | (−) |
| Different Epitope | | | | | | Different Epitope | | | | | |

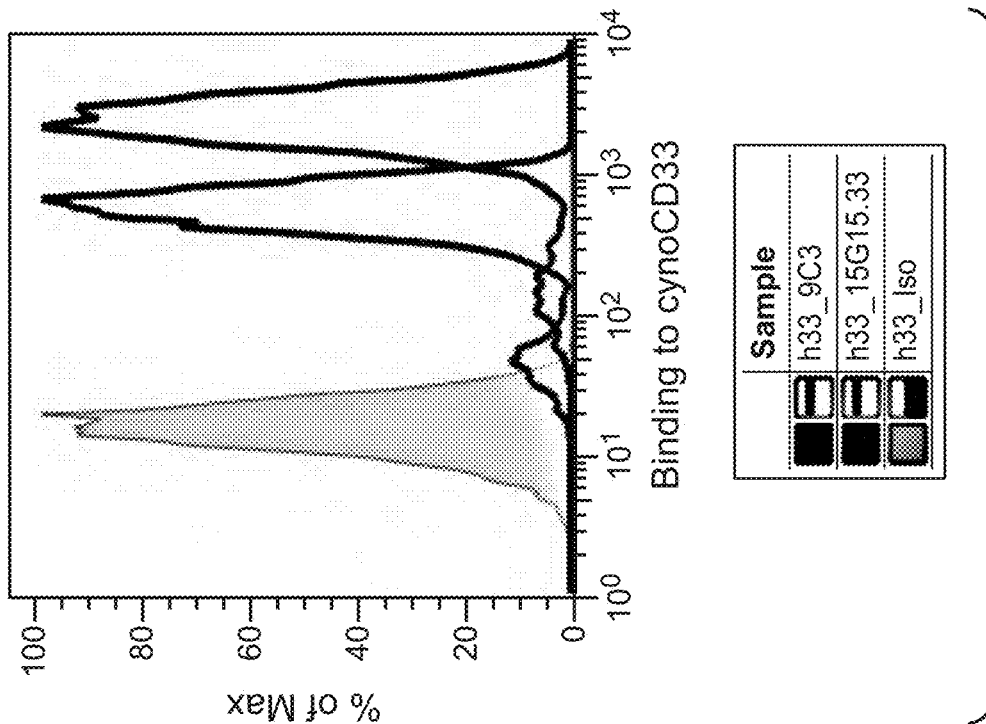
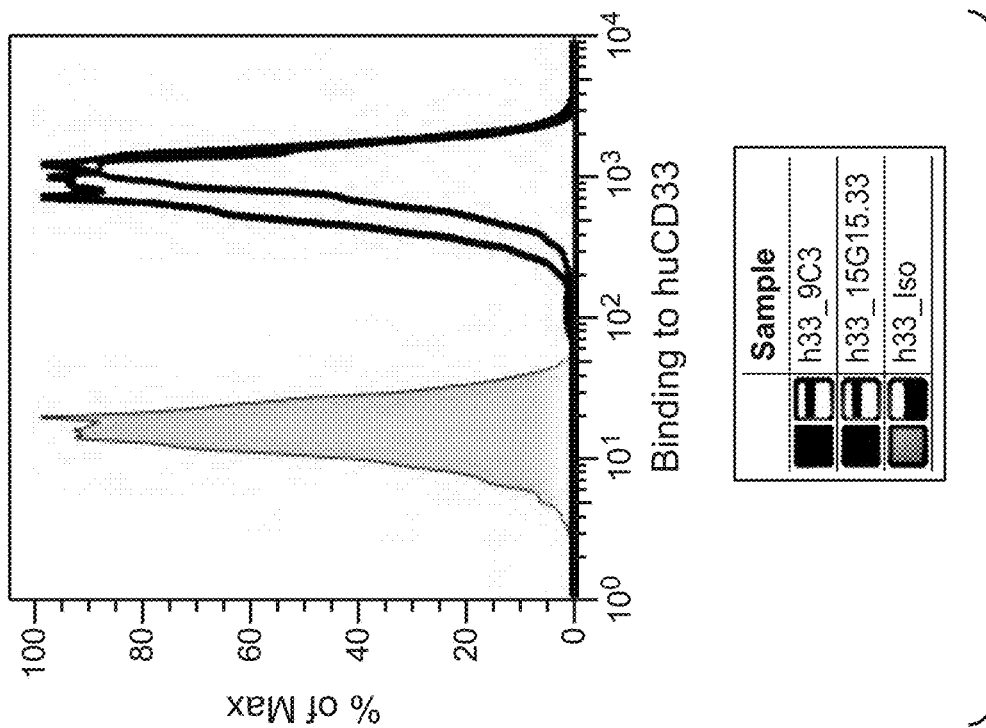
FIG. 10A
FIG. 10B

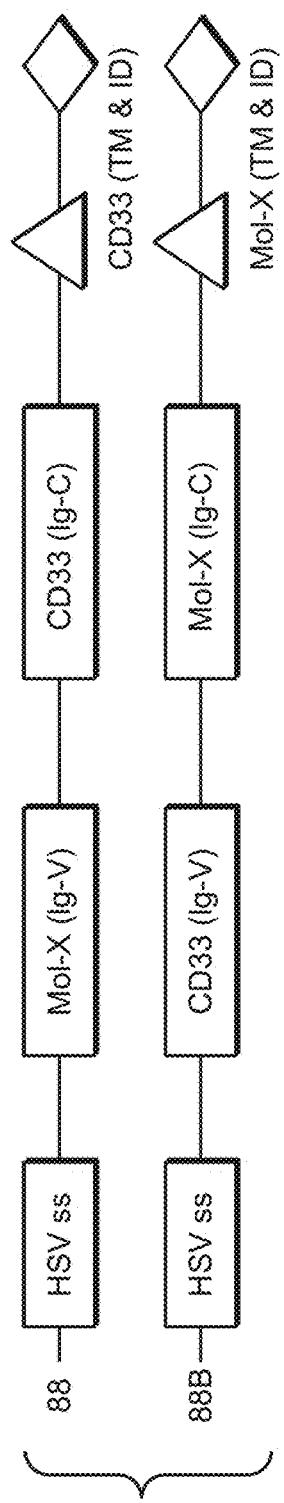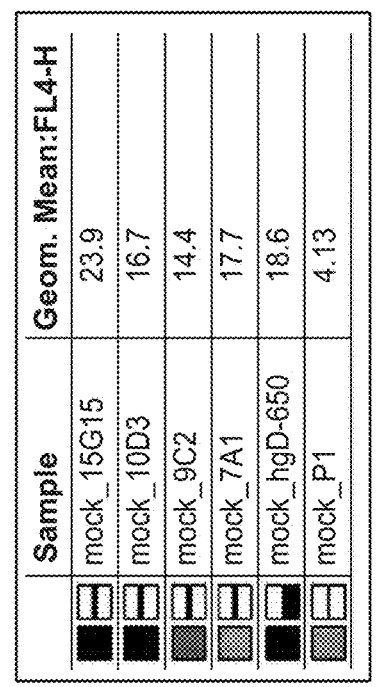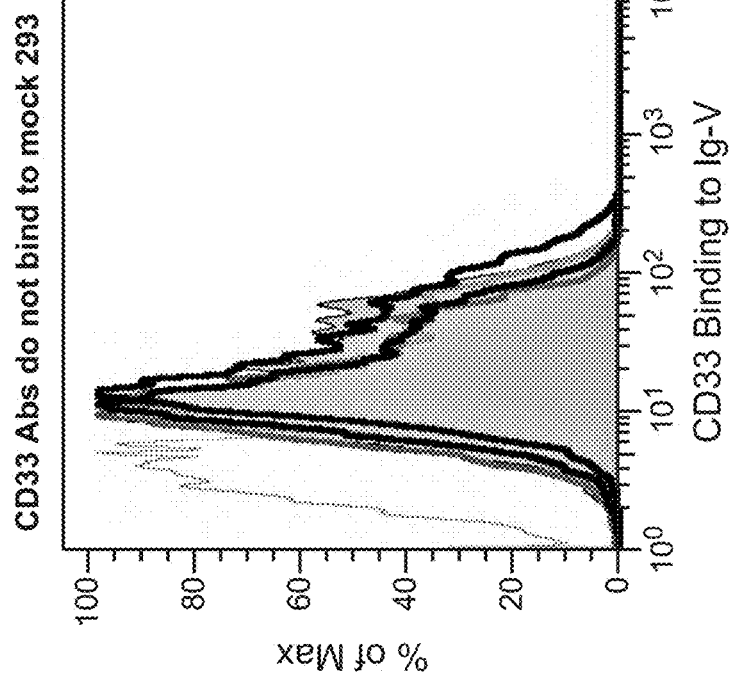
FIG. 12A
FIG. 12B

```
huCD33_G69    1  MDPNFWLQVQESVTVQEGLCVLVPCTFFHPIPYYDKNSPVHGYWFREGAI  50
_huCD33_R69   1  MDPNFWLQVQESVTVQEGLCVLVPCTFFHPIPYYDKNSPVHGYWFREGAI  50

(S102A)                      (S115A)
huCD33_G69    51 ISGDSPVATNKLDQEVQEETQGRFRLLGDPSRNNCSLSIVDARRRDNGSY  100
_huCD33_R69   51 ISRDSPVATNKLDQEVQEETQGRFRLLGDPSRNNCSLSIVDARRRDNGSY  100 huCD33_G69   101 FFRMERGSTKYSYKSPQLS  119
_huCD33_R69  101 FFRMERGSTKYSYKSPQLS  119
```

Ig-V Like Domain

*FIG. 13C*

```
huCD33_G69    1  MDPNFWLQVQESVTVQEGLCVLVPCTFFHPIPYYDKNSPVHGYWFREGAI  50
_huCD33_R69   1  MDPNFWLQVQESVTVQEGLCVLVPCTFFHPIPYYDKNSPVHGYWFREGAI  50

(R69G)
huCD33_G69    51 ISGDSPVATNKLDQEVQEETQGRFRLLGDPSRNNCSLSIVDARRRDNGSY  100
_huCD33_R69   51 ISRDSPVATNKLDQEVQEETQGRFRLLGDPSRNNCSLSIVDARRRDNGSY  100 huCD33_G69   101 FFRMERGSTKYSYKSPQLS  119
_huCD33_R69  101 FFRMERGSTKYSYKSPQLS  119
```

Ig-V Like Domain

*FIG. 14A*

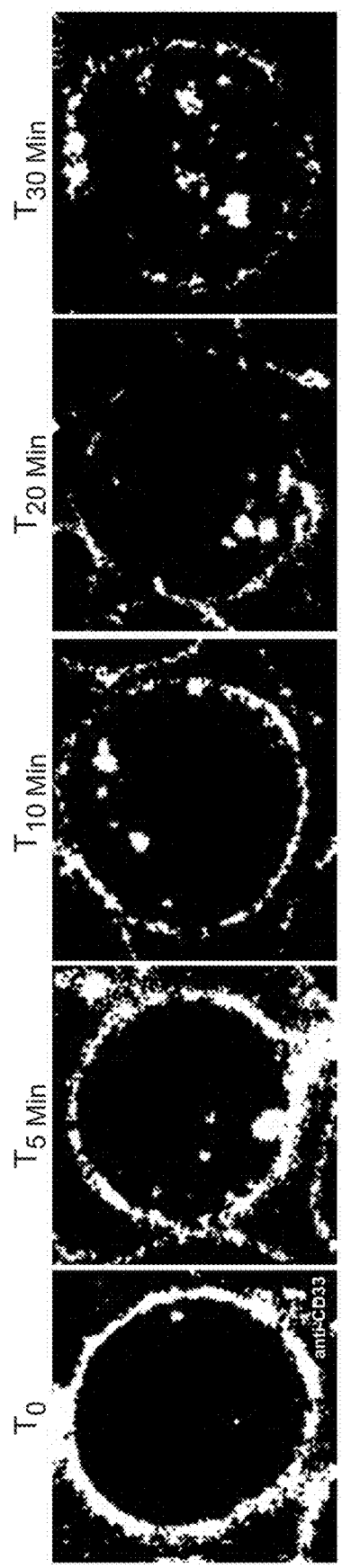
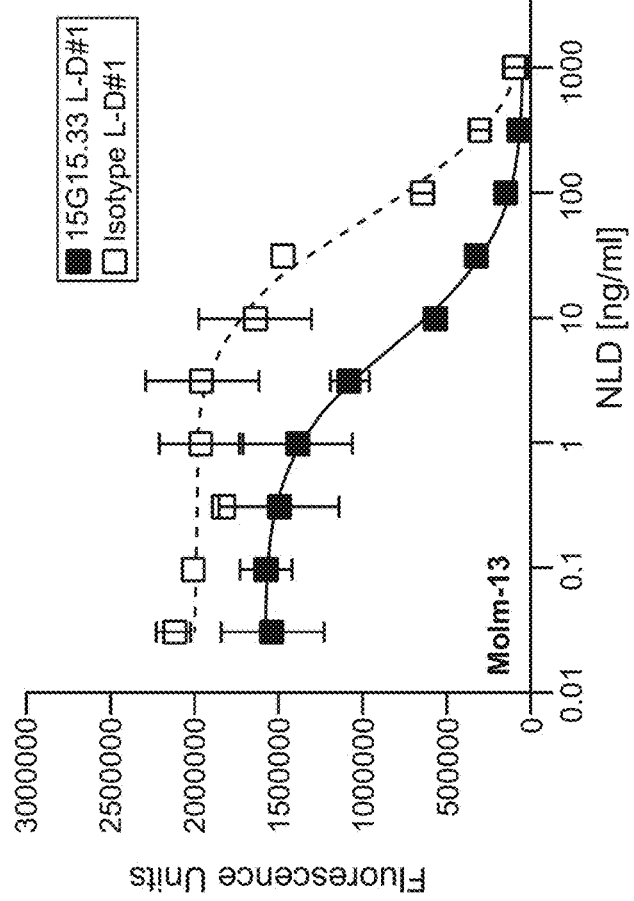
FIG. 15A
FIG. 15B

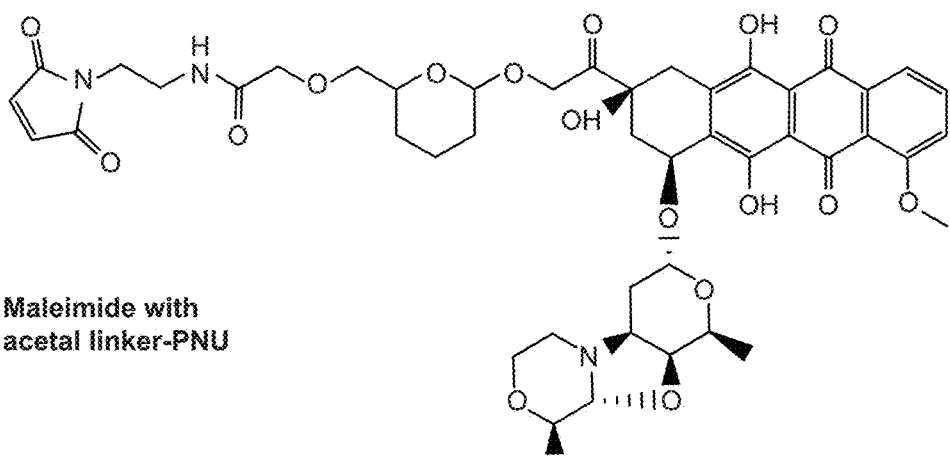
Maleimide with acetal linker-PNU
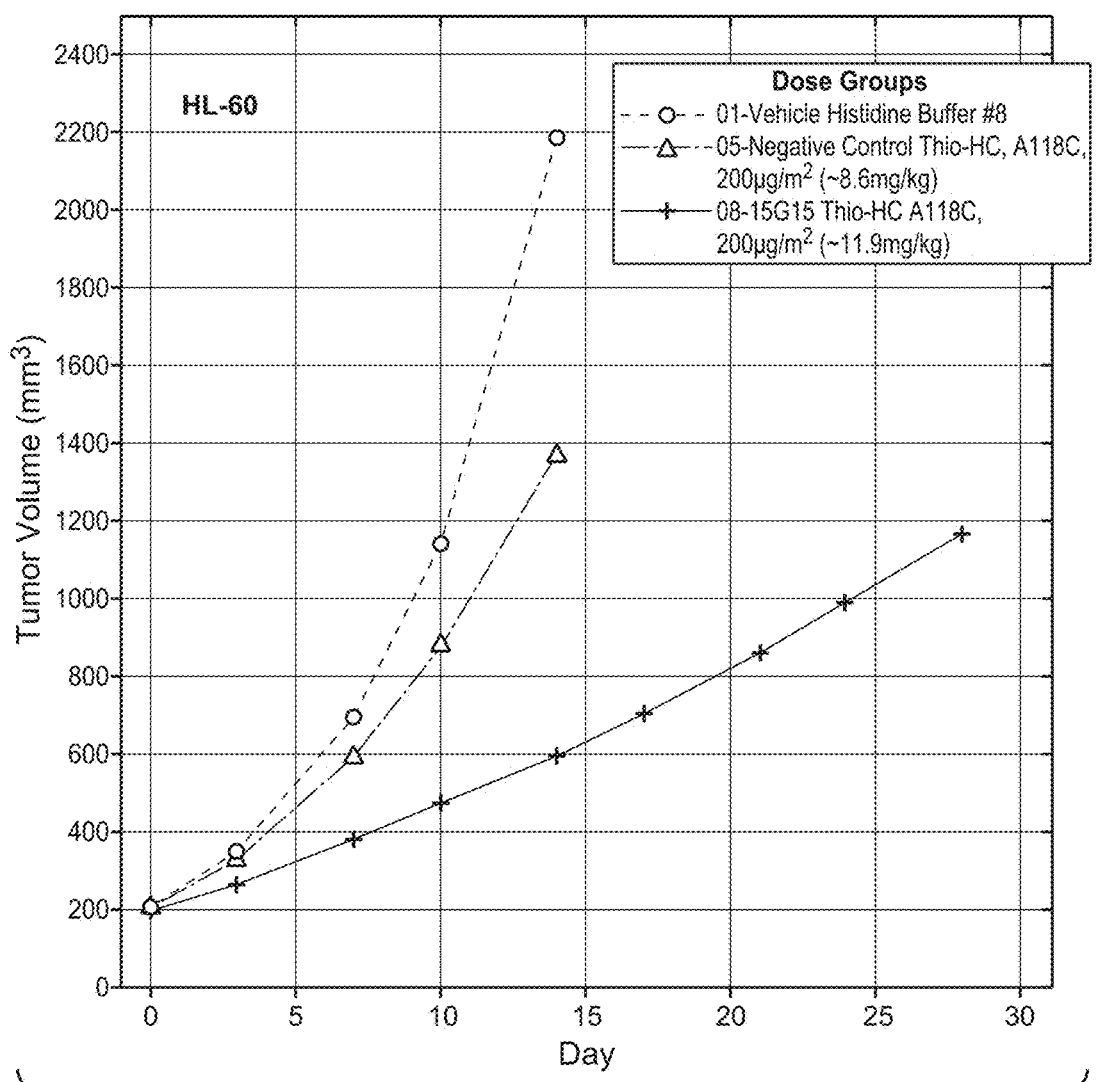
FIG. 17

ANTI-CD33 ANTIBODIES AND IMMUNOCONJUGATES

CROSS REFERENCE TO RELATED APPLICATIONS

This application is a divisional of U.S. patent application Ser. No. 15/171,128, filed Jun. 2, 2016, which is a continuation of International Application No. PCT/US2014/069874, filed Dec. 12, 2014, which claims priority to U.S. Provisional Application No. 61/916,087, filed Dec. 13, 2013; each of which is incorporated by reference herein in its entirety for any purpose.

SEQUENCE LISTING

The present application is filed with a Sequence Listing in electronic format. The Sequence Listing is provided as a file entitled "2018-06-06_01146-0032-01US_Replacement_Seq_List_ST25" created on Jun. 6, 2018, which is 80,397 bytes in size. The information in the electronic format of the sequence listing is incorporated herein by reference in its entirety.

FIELD OF THE INVENTION

The present invention relates to anti-CD33 antibodies and immunoconjugates and methods of using the same.

BACKGROUND

CD33, a member of the sialic acid binding, immunoglobulin-like lectin family, is a 67-kDa glycosylated transmembrane protein. It is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells. See Sabbath et al., *J. Clin. Invest.* 75:756-56 (1985) and Andrews et al., *Blood* 68:1030-5 (1986). CD33 contains two tyrosine residues on its cytoplasmic tail, each of which is followed by hydrophobic residues similar to the immunoreceptor tyrosine-based inhibitory motif (ITIM) seen in many inhibitory receptors.

Monoclonal antibody (mAb)-based therapy has become an important treatment modality for cancer. Leukemia is well suited to this approach because of the accessibility of malignant cells in the blood, bone marrow, spleen, and lymph nodes and the well-defined immunophenotypes of the various lineages and stages of hematopoietic differentiation that permit identification of antigenic targets. Most studies for acute myeloid leukemia (AML) have focused on CD33. Responses with the unconjugated anti-CD33 mAb lintuzumab have had modest single agent and activity against AML and failed to improve patient outcomes in two randomized trials when combined with conventional chemotherapy. The immunoconjugate gemtuzumab ozogamicin (GO; Mylotarg), an anti-CD33 monoclonal antibody conjugated to the antitumor antibiotic calicheamicin, improved survival in a subset of AML patients when combined with standard chemotherapy, but safety concerns led to marketing withdrawal in the US. Additionally, three phase I studies of an anti-CD33-maytansine conjugate (AVE9633; huMy9-6-DM4) in AML patients. The maximum tolerated dose (MTD) was determined only in one of the phase I studies (administration schedule day 1/8) as the other two studies were discontinued before reaching the MTD since no signs of activity were apparent at doses much higher than the saturating dose. The activity of AVE9633 in the phase I administration schedule day 1/8 was modest. Lapusan et al., *Invest. New Drugs* 30:1121-1131 (2012).

There is a need in the art for safe and effective agents that target CD33 for the diagnosis and treatment of CD33-associated conditions, such as cancer. The invention fulfills that need and provides other benefits.

SUMMARY

The invention provides anti-CD33 antibodies and immunoconjugates and methods of using the same.

In some embodiments, an isolated antibody that binds to CD33 is provided. In some embodiments, the antibody binds to CD33 and has one or more of the following characteristics:

a) binds to recombinant human CD33;
b) binds to recombinant cynomolgus monkey CD33;
c) binds to endogenous CD33 on the surface of human peripheral blood mononucleocytes (PBMCs);
d) binds to endogenous CD33 on the surface of cynomolgus monkey PBMCs;
e) binds to endogenous CD33 on the surface of a cancer cell;
f) binds to endogenous CD33 on the surface of an AML cancer cell;
g) binds to endogenous CD33 on the surface of Molm-13 cells;
h) binds to CD33 comprising a R69G mutation;
i) binds to CD33 Ig V domain;
j) binds to CD33 that is void of N-linked glycosylation at N100;
k) binds to CD33 that is void of N-linked glycosylation at N113;
l) binds to CD33 comprising an S102A mutation;
m) binds to CD33 comprising an S115A mutation;
n) does not bind CD33 Ig C2 domain;
o) competes for human CD33 binding with My9.6 antibody;
p) competes for human CD33 binding with antibody 33H4;
q) competes for human CD33 binding with antibody 23E4;
r) binds to endogenous human CD33 with a Kd of less than 15 nM, less than 10 nM, less than 7 nM, less than 5 nM, or less than 3 nM;
s) binds to recombinant human CD33 with a Kd of less than 10 nM, less than 7 nM, less than 5 nM, or less than 3 nM; and/or
t) binds to recombinant cynomolgus monkey CD33 with a Kd of less than 10 nM, less than 7 nM, less than 5 nM, or less than 3 nM, less than 2 nM, or less than 1 nM.

In some embodiments, an isolated antibody that binds to CD33 is provided, wherein the antibody comprises (a) HVR-H1 comprising the amino acid sequence of SEQ ID NO: 112; (b) HVR-H2 comprising the amino acid sequence of SEQ ID NO: 113; (c) HVR-H3 comprising the amino acid sequence of SEQ ID NO: 114; (d) HVR-L1 comprising the amino acid sequence of SEQ ID NO:5; (e) HVR-L2 comprising the amino acid sequence of SEQ ID NO: 111; and (f) HVR-L3 comprising the amino acid sequence of SEQ ID NO:7. In some embodiments, the antibody comprises (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises (a) HVR-H1 comprising the amino acid sequence of SEQ ID NO: 118; (b) HVR-H2 comprising the amino acid sequence of SEQ ID NO: 119; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO: 111; and (f) HVR-L3 comprising the amino acid sequence of SEQ ID NO:7.

In some embodiments, an antibody that binds CD33 comprises (a) HVR-H1 comprising the amino acid sequence of SEQ ID NO:8, SEQ ID NO: 11, SEQ ID NO:20, SEQ ID NO:23, or SEQ ID NO:30; (b) HVR-H2 comprising the amino acid sequence of SEQ ID NO:9, SEQ ID NO: 12, SEQ ID NO:21, SEQ ID NO:24, SEQ ID NO:31, SEQ ID NO:32, SEQ ID NO:33, SEQ ID NO:34, or SEQ ID NO:35; (c) HVR-H3 comprising the amino acid sequence of SEQ ID NO:10, SEQ ID NO:13, SEQ ID NO:22, or SEQ ID NO:25; (d) HVR-L1 comprising the amino acid sequence of SEQ ID NO:5; (e) HVR-L2 comprising the amino acid sequence of SEQ ID NO:6, SEQ ID NO:26, SEQ ID NO:27, SEQ ID NO:28, or SEQ ID NO:29; and (f) HVR-L3 comprising the amino acid sequence of SEQ ID NO:7.

In some embodiments, an antibody that binds CD33 comprises:

(i) (a) HVR-H1 comprising the amino acid sequence of SEQ ID NO:8; (b) HVR-H2 comprising the amino acid sequence of SEQ ID NO:9; (c) HVR-H3 comprising the amino acid sequence of SEQ ID NO: 10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(ii) (a) HVR-H1 comprising the amino acid sequence of SEQ ID NO: 11; (b) HVR-H2 comprising the amino acid sequence of SEQ ID NO: 12; (c) HVR-H3 comprising the amino acid sequence of SEQ ID NO: 13; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(iii) (a) HVR-H1 comprising the amino acid sequence of SEQ ID NO:20; (b) HVR-H2 comprising the amino acid sequence of SEQ ID NO:21; (c) HVR-H3 comprising the amino acid sequence of SEQ ID NO:22; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(iv) (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(v) (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:26; and (f) HVR-L3 comprising the amino acid sequence of SEQ ID NO:7;

(vi) (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:27; and (f) HVR-L3 comprising the amino acid sequence of SEQ ID NO:7;

(vii) (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:28; and (f) HVR-L3 comprising the amino acid sequence of SEQ ID NO:7;

(viii) (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:29; and (f) HVR-L3 comprising the amino acid sequence of SEQ ID NO:7;

(ix) (a) HVR-H1 comprising the amino acid sequence of SEQ ID NO:30; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(x) (a) HVR-H1 comprising the amino acid sequence of SEQ ID NO:23; (b) HVR-H2 comprising the amino acid sequence of SEQ ID NO:31; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(xi) (a) HVR-H1 comprising the amino acid sequence of SEQ ID NO:23; (b) HVR-H2 comprising the amino acid sequence of SEQ ID NO:32; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(xii) (a) HVR-H1 comprising the amino acid sequence of SEQ ID NO:23; (b) HVR-H2 comprising the amino acid sequence of SEQ ID NO:33; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7;

(xiii) (a) HVR-H1 comprising the amino acid sequence of SEQ ID NO:23; (b) HVR-H2 comprising the amino acid sequence of SEQ ID NO:34; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7; or (xiv) (a) HVR-H1 comprising the amino acid sequence of SEQ ID NO:23; (b) HVR-H2 comprising the amino acid sequence of SEQ ID NO:35; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In some embodiments, an antibody that binds CD33 comprises:
   a) a heavy chain variable region comprising the sequence of SEQ ID NO: 66 and a light chain variable region comprising the sequence of SEQ ID NO: 65;
   b) a heavy chain variable region comprising the sequence of SEQ ID NO: 68 and a light chain variable region comprising the sequence of SEQ ID NO: 67;
   c) a heavy chain variable region comprising the sequence of SEQ ID NO: 78 and a light chain variable region comprising the sequence of SEQ ID NO: 77;
   d) a heavy chain variable region comprising the sequence of SEQ ID NO: 80 and a light chain variable region comprising the sequence of SEQ ID NO: 79;
   e) a heavy chain variable region comprising the sequence of SEQ ID NO: 82 and a light chain variable region comprising the sequence of SEQ ID NO: 81;
   f) a heavy chain variable region comprising the sequence of SEQ ID NO: 84 and a light chain variable region comprising the sequence of SEQ ID NO: 83;
   g) a heavy chain variable region comprising the sequence of SEQ ID NO: 86 and a light chain variable region comprising the sequence of SEQ ID NO: 85;
   h) a heavy chain variable region comprising the sequence of SEQ ID NO: 88 and a light chain variable region comprising the sequence of SEQ ID NO: 87;
   i) a heavy chain variable region comprising the sequence of SEQ ID NO: 90 and a light chain variable region comprising the sequence of SEQ ID NO: 89;
   j) a heavy chain variable region comprising the sequence of SEQ ID NO: 92 and a light chain variable region comprising the sequence of SEQ ID NO: 91;
   k) a heavy chain variable region comprising the sequence of SEQ ID NO: 94 and a light chain variable region comprising the sequence of SEQ ID NO: 93;
   l) a heavy chain variable region comprising the sequence of SEQ ID NO: 96 and a light chain variable region comprising the sequence of SEQ ID NO: 95;
   m) a heavy chain variable region comprising the sequence of SEQ ID NO: 98 and a light chain variable region comprising the sequence of SEQ ID NO: 97; or
   n) a heavy chain variable region comprising the sequence of SEQ ID NO: 100 and a light chain variable region comprising the sequence of SEQ ID NO: 99.

In some embodiments, an isolated antibody that binds to CD33 is provided. In some embodiments, the antibody binds to CD33 and has one or more of the following characteristics:
   u) binds to recombinant human CD33;
   v) binds to recombinant cynomolgus monkey CD33;
   w) binds to endogenous CD33 on the surface of human peripheral blood mononucleocytes (PBMCs);
   x) binds to recombinant human CD33 with a Kd of less than 10 nM, less than 7 nM, less than 5 nM, less than 3 nM, less than 2 nM, or less than 1 nM; and/or
   y) binds to recombinant cynomolgus monkey CD33 with a Kd of less than 10 nM, less than 7 nM, less than 5 nM, less than 3 nM, less than 2 nM, or less than 1 nM.

In some embodiments, an isolated antibody that binds to CD33 comprises (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19; (d) HVR-L1 comprising the amino acid sequence of SEQ ID NO: 14; (e) HVR-L2 comprising the amino acid sequence of SEQ ID NO: 15; and (f) HVR-L3 comprising the amino acid sequence of SEQ ID NO: 16.

In some embodiments, an antibody that binds CD33 comprises:
   z) a heavy chain variable region comprising the sequence of SEQ ID NO: 70 and a light chain variable region comprising the sequence of SEQ ID NO: 69;
   aa) a heavy chain variable region comprising the sequence of SEQ ID NO: 72 and a light chain variable region comprising the sequence of SEQ ID NO: 71;
   bb) a heavy chain variable region comprising the sequence of SEQ ID NO: 74 and a light chain variable region comprising the sequence of SEQ ID NO: 73; or
   cc) a heavy chain variable region comprising the sequence of SEQ ID NO: 76 and a light chain variable region comprising the sequence of SEQ ID NO: 75.

In some embodiments, an isolated antibody that binds to CD33 comprises (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In some embodiments, an isolated antibody that binds to CD33 comprises (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:26; and (f) HVR-L3 comprising the amino acid sequence of SEQ ID NO:7.

In some embodiments, an isolated antibody that binds to CD33 comprises (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19; (d) HVR-L1 comprising the amino acid sequence of SEQ ID NO: 14; (e) HVR-L2 comprising the amino acid sequence of SEQ ID NO: 15; and (f) HVR-L3 comprising the amino acid sequence of SEQ ID NO: 16.

In some embodiments, the antibody is a monoclonal antibody. In some embodiments, the antibody is a human, humanized, or chimeric antibody. In some embodiments, the antibody is an IgG1, IgG2a or IgG2b antibody. In some embodiments, the antibody is an antibody fragment that binds CD33. In some embodiments, CD33 is human CD33 has the sequence of SEQ ID NO: 1, with or without a signal sequence (e.g., with or without amino acids 1-17).

In some embodiments, an isolated nucleic acid encoding an antibody described herein is provided. In some embodiments, a host cell comprising the nucleic acid is provided. In some embodiments, a method of producing an antibody comprising culturing the host cell so that the antibody is produced is provided.

In some embodiments, an immunoconjugate comprising an antibody described herein and a cytotoxic agent is provided. In some embodiments, the immunoconjugate has the formula Ab-(L-D)p, wherein:
(a) Ab is the antibody of any one of claim 1 to 15;
(b) L is a linker;
(c) D is a cytotoxic agent; and
(d) p ranges from 1-8.

In some embodiments, the cytotoxic agent is selected from a maytansinoid, a calicheamicin, a pyrrolobenzodiazepine, and a nemorubicin derivative. In some embodiments, D is a pyrrolobenzodiazepine of Formula A:

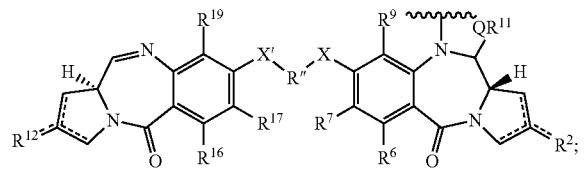

A wherein the dotted lines indicate the optional presence of a double bond between C1 and C2 or C2 and C3;

$R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{3-8}$ heterocyclyl and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms and/or aromatic rings that are optionally substituted; and X and X' are independently selected from O, S and N(H).
In some embodiments, D has the structure:

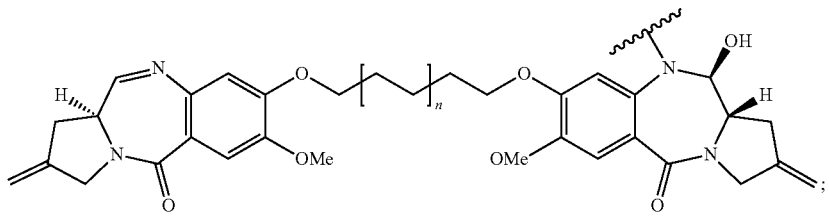

wherein n is 0 or 1.

In some embodiments, D is a nemorubicin derivative. In some embodiments, D has a structure selected from:

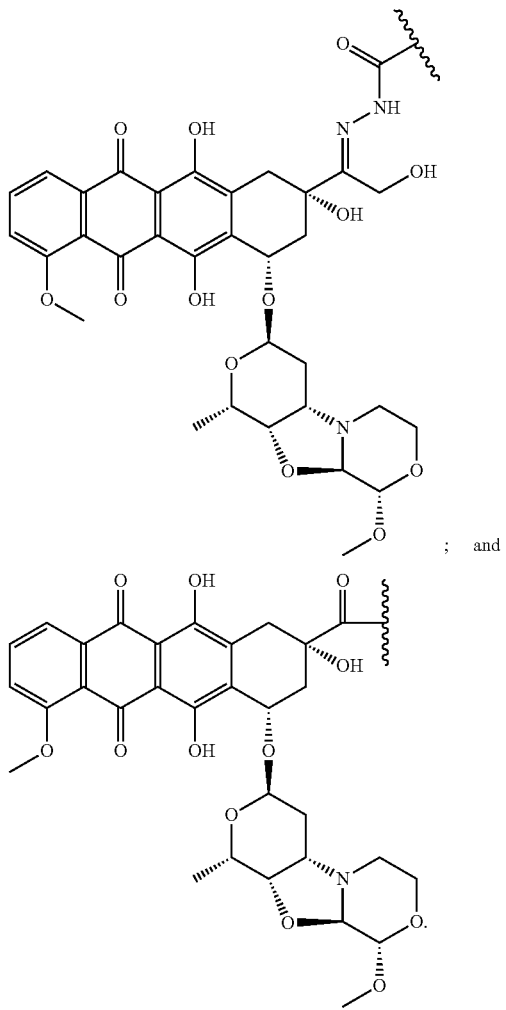

In some embodiments, an immunoconjugate comprises a linker that is cleavable by a protease. In some embodiments, an immunoconjugate comprises a linker that is acid-labile. In some embodiments, the linker comprises hydrazone.

In some embodiments, an immunoconjugate comprising an antibody described herein has a formula selected from:

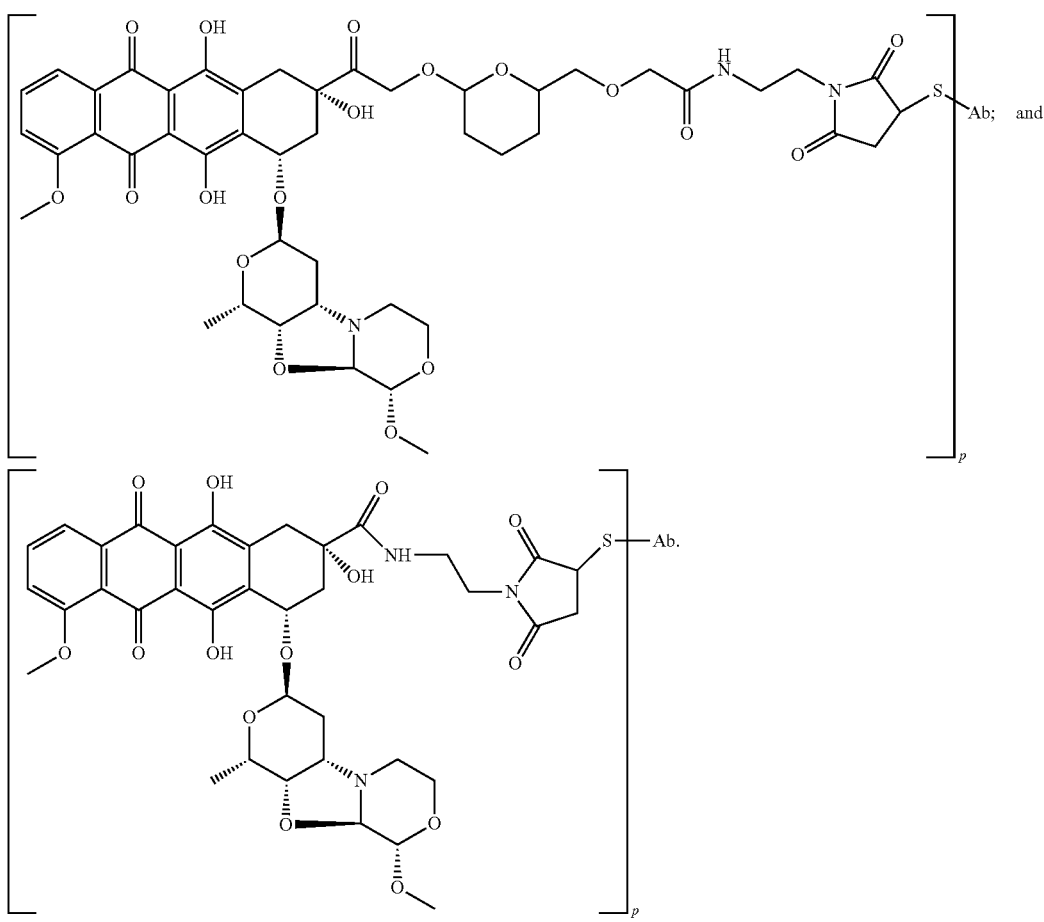

In any of the immunoconjugate embodiments described herein, p ranges from 2-5.

In some embodiments, pharmaceutical formulations are provided. In some embodiments, a pharmaceutical formulation comprises an immunoconjugate described herein and a pharmaceutically acceptable carrier. In some embodiments, the pharmaceutical formulation comprises an additional therapeutic agent.

In some embodiments, methods of treatment are provided. In some embodiments, methods of treating CD33-positive cancers are provided. In some embodiments, a method of treatment comprises administering to an individual an effective amount of an immunoconjugate described herein or a pharmaceutical formulation described herein. In some embodiments, the CD33-positive cancer is AML. In some embodiments, the method comprises administering an additional therapeutic agent to the individual.

In some embodiments, methods of inhibiting proliferation of a CD33-positive cell are provided. In some embodiments, the method comprises exposing the cell to an immunoconjugate described herein under conditions permissive for binding of the immunoconjugate to CD33 on the surface of the cell, thereby inhibiting proliferation of the cell. In some embodiments, the cell is an AML cancer cell.

In some embodiments, a method of detecting human CD33 in a biological sample is provided. In some embodiments, a method comprises contacting the biological sample with an anti-CD33 antibody under conditions permissive for binding of the anti-CD33 antibody to a naturally occurring human CD33, and detecting whether a complex is formed between the anti-CD33 antibody and a naturally occurring human CD33 in the biological sample. In some embodiments, an anti-CD33 antibody is an antibody described herein. In some embodiments, the biological sample is an AML cancer sample.

In some embodiments, a method for detecting a CD33-positive cancer is provided. In some such embodiments, a method comprises (i) administering a labeled anti-CD33 antibody to a subject having or suspected of having a CD33-positive cancer, and (ii) detecting the labeled anti-CD33 antibody in the subject, wherein detection of the labeled anti-CD33 antibody indicates a CD33-positive cancer in the subject. In some embodiments, an anti-CD33 antibody is an antibody described herein. In some such embodiments, the labeled anti-CD33 antibody comprises an anti-CD33 antibody conjugated to a positron emitter. In some embodiments, the positron emitter is $^{89}$Zr.

BRIEF DESCRIPTION OF THE FIGURES

FIG. 1A-1B shows alignment of the light chain variable region sequences (SEQ ID NOs: 65, 67, 77, and 79, respectively) (A) and heavy chain variable region sequences (SEQ ID NOs: 66, 68, 78, and 80, respectively) (B) of 7A1, 9C2, 10D3, and 15G15.

Figure 2A-1:
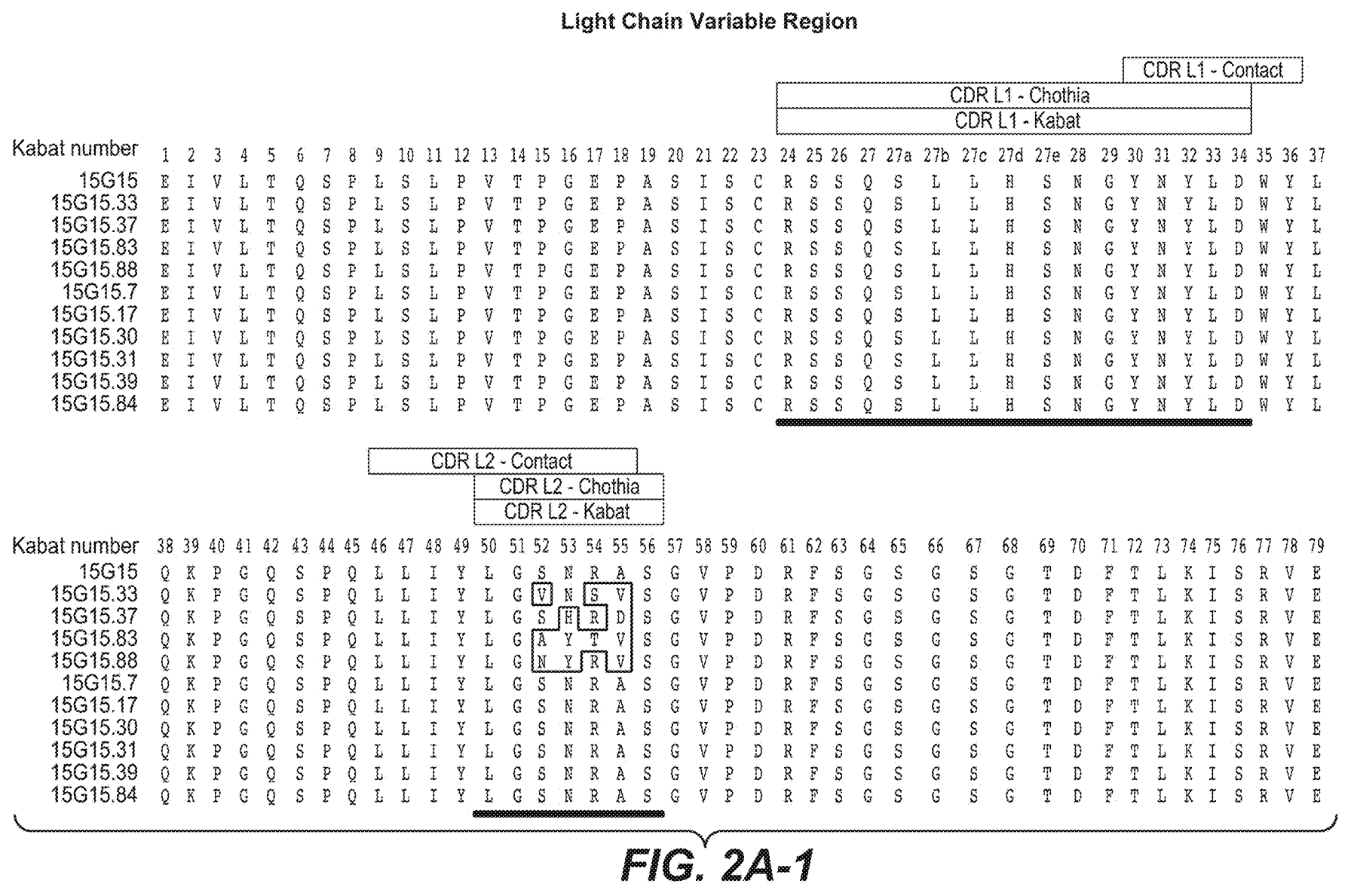
Figure 2B-1:
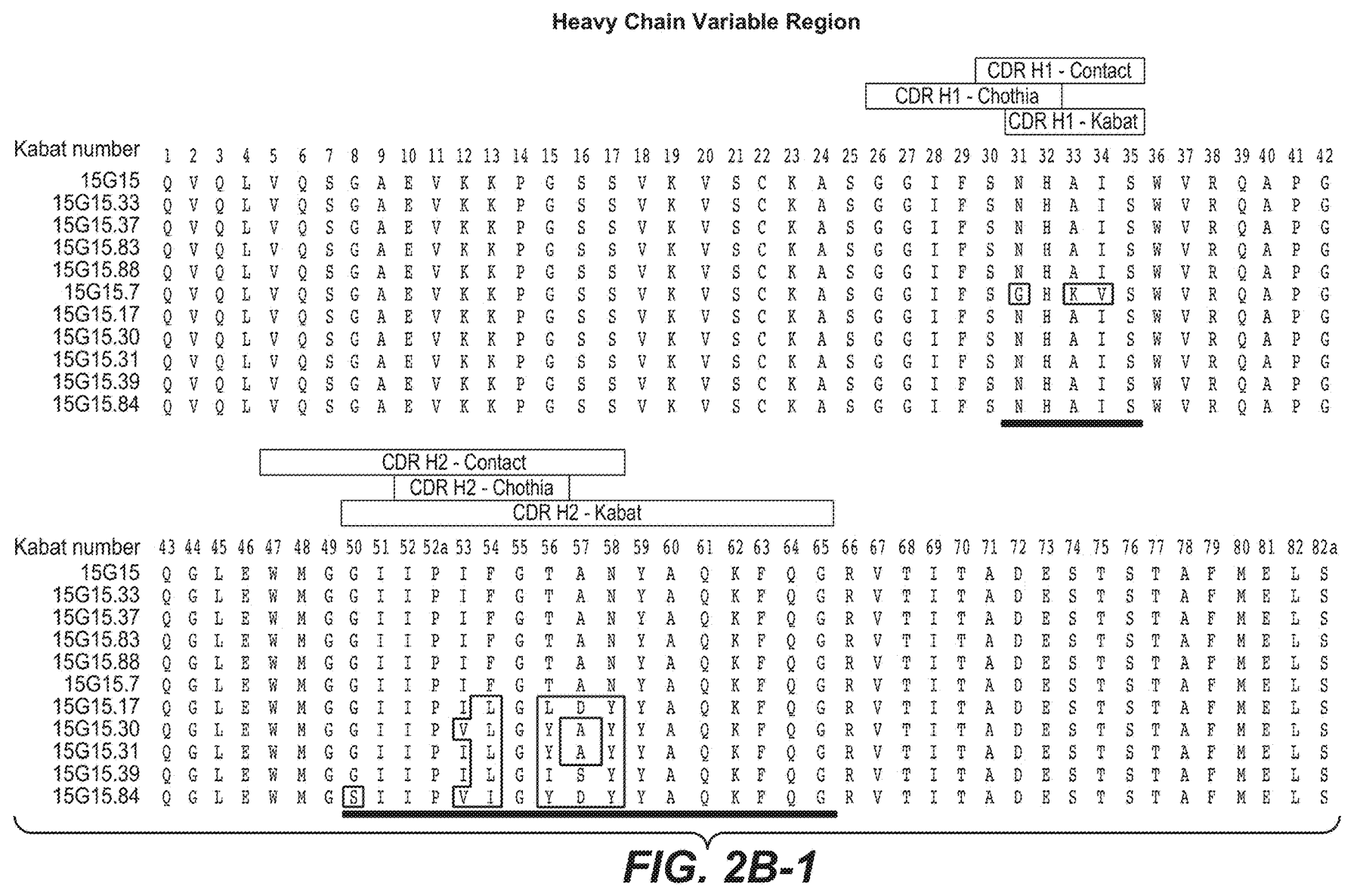

FIG. 2A-1-2B-2 shows alignment of the light chain variable region sequences (SEQ ID NOs: 79, 81, 83, 85, 87, 89, 91, 93, 95, 97, and 99, respectively) (A-1 and A-2) and heavy chain variable region sequences (SEQ ID NOs: 80, 82, 84, 86, 88, 90, 92, 94, 96, 98, and 100, respectively) (B-1 and B-2) of 15G15, 15G15.33, 15G15.37, 15G15.83, 15G15.88, 15G15.7, 15G15.17, 15G15.30, 15G15.31, 15G15.39, and 15G15.84.

FIG. 3A-3B shows alignment of the light chain variable region sequences (SEQ ID NOs: 101, 103, 105, 107, and 109, respectively) (A) and heavy chain variable region sequences (SEQ ID NOs: 102, 104, 106, 108, and 110, respectively) (B) of 23E4, 27C6, 33F3, 33F9, and 33H4.

FIG. 4A-4B shows alignment of the light chain variable region sequences (SEQ ID NOs: 69, 71, 73, and 75, respectively) (A) and heavy chain variable region sequences (SEQ ID NOs: 70, 72, 74, and 76, respectively) (B) of 9C3, 9C3.2, 9C3.3, and 9C3.4.

FIG. 8A-8D shows anti-CD33 antibody epitope binning and comparison to MY9.6 using huCD33 (A-C) and cynoCD33 (D). See e.g., Griffin et al., *LeukRes.* 8:521 (1984) regarding MY9.

FIG. 10A-10C shows anti-CD33 antibody 9C3 does not compete with anti-CD33 antibody 15G15.33 and binds to an epitope distinct from 15G15.33.

FIG. 12A-12D. FIG. 12A shows a schematic of the domain swapped polypeptide used in the Examples. FIG. 12B-12D shows that anti-CD33 antibodies 7A1, 9C2, 10D3 and 15G15 bind to Ig-like V domain of huCD33.

FIG. 13A-13C shows that anti-CD33 antibodies WM53 (A) and 15G15 (B), are capable of binding to huCD33 Ig-like V domain void of N-linked glycosylation. In FIG. 13C, the consensus N-glycosylation site sequences of the Ig-like V domain of huCD33 are boxed, including mutation sites S102A and S115A. (Because only the Ig-like V domain is shown, the numbering shown in the figure is different from the numbering of the full-length CD33.) (huCD33_G69 corresponds to SEQ ID NO: 122, huCD33_R69 corresponds to SEQ ID NO: 123).

FIG. 14A-14C shows the wild-type and single nucleotide polymorphism (SNP) sequences of the R69 and G69 Ig-V domain of CD33 (A), and shows that the binding of the anti-CD33 antibodies, 7A1, 9C2, 10D3, 15G15, 23E4, 27C6, 33F9, and 33H4, was not affected by the SNP (r2455069) (e.g., R69G). (huCD33_G69 corresponds to SEQ ID NO: 122, huCD33_R69 corresponds to SEQ ID NO: 123).

FIG. 15A-15B shows internalization and in vitro potency of anti-CD33 antibodies, 15G15 and 15G15.33 L-D #1.

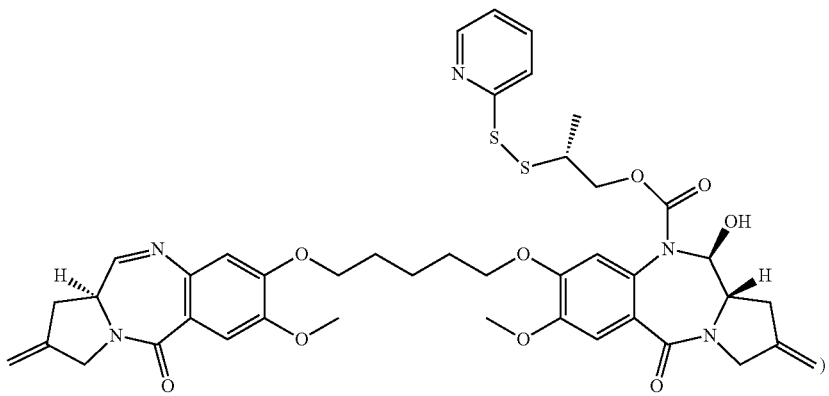

Figure 5A:
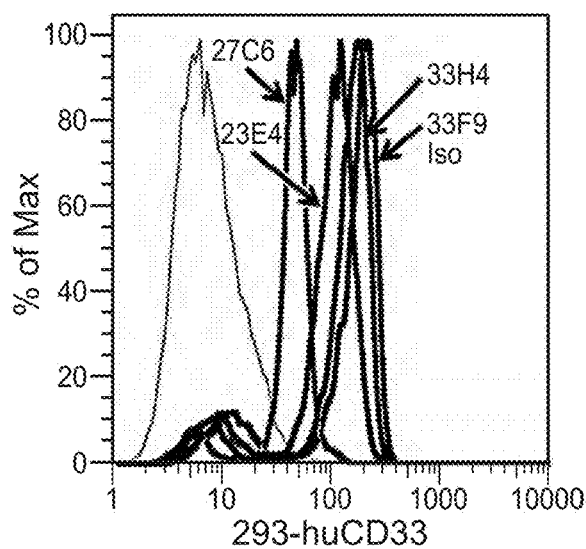
FIG. 5A-5D show species cross-reactivity of anti-CD33 antibodies to recombinant CD33. Anti-CD33 antibody binding to 293 cells expressing recombinant human (hu) CD33 (A, C) and cynomolgus (cyno) CD33 (B, D) is shown.
Figure 5B:
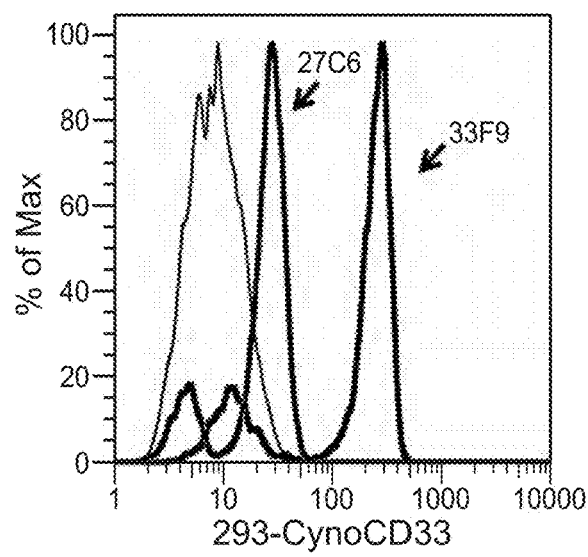
Figure 5C:
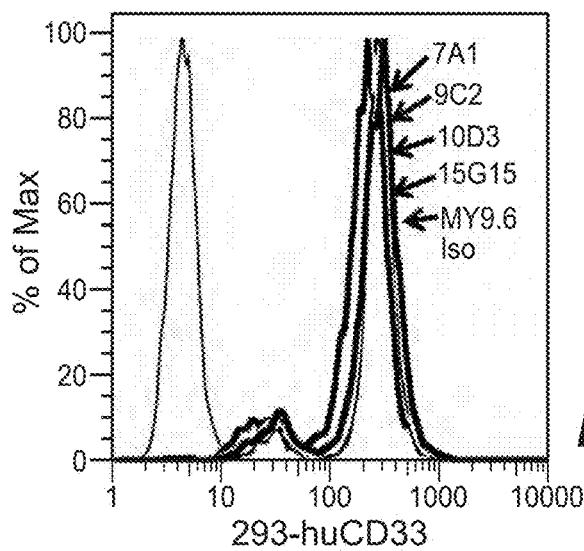
Figure 5D:
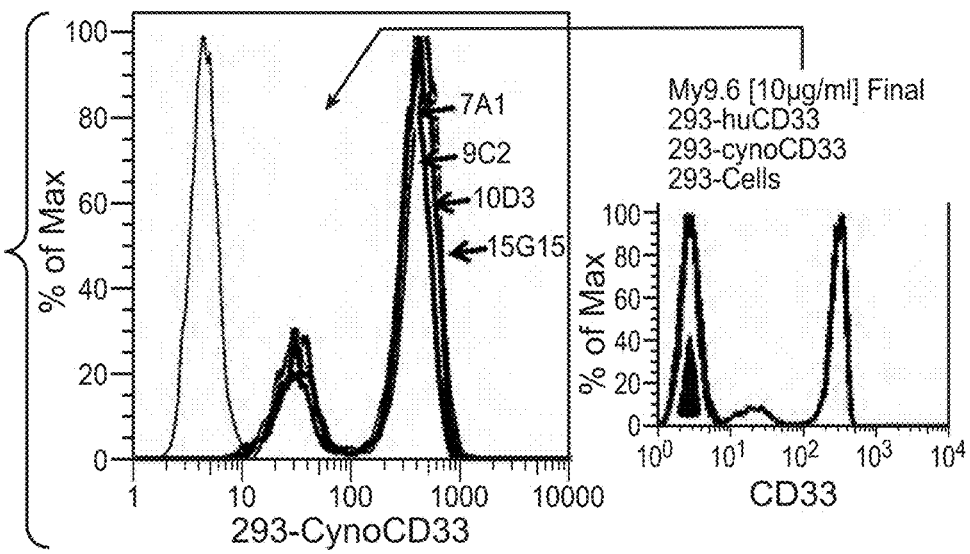
Figure 6A:
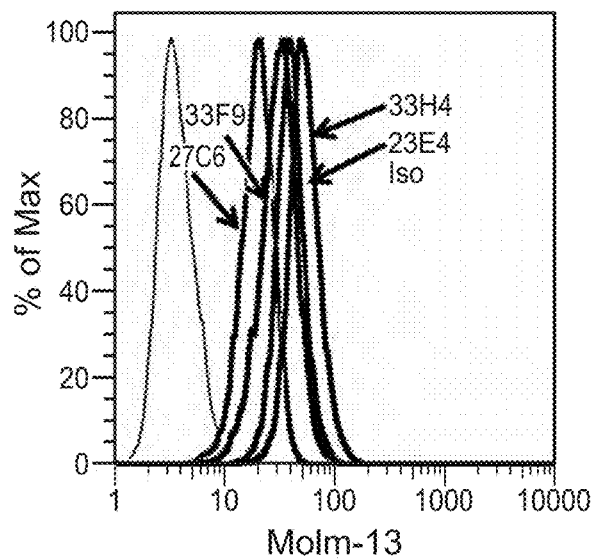
FIG. 6A-6D shows anti-CD33 antibody binding to endogenous huCD33 expressed in Molm-13 (A, C) and AML (B, D) cells.
Figure 6B:
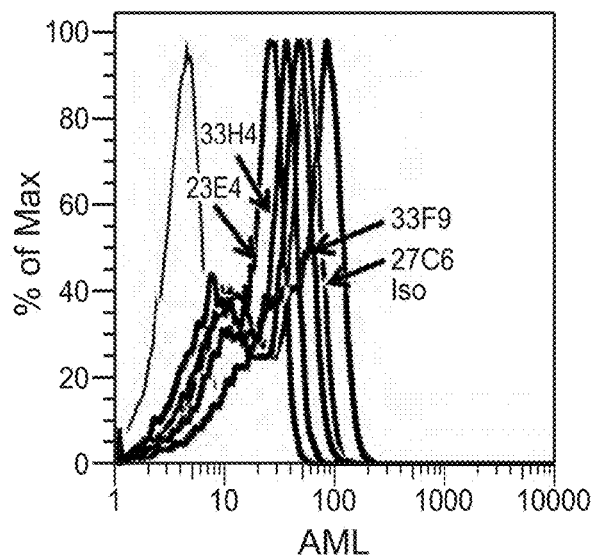
Figure 6C:
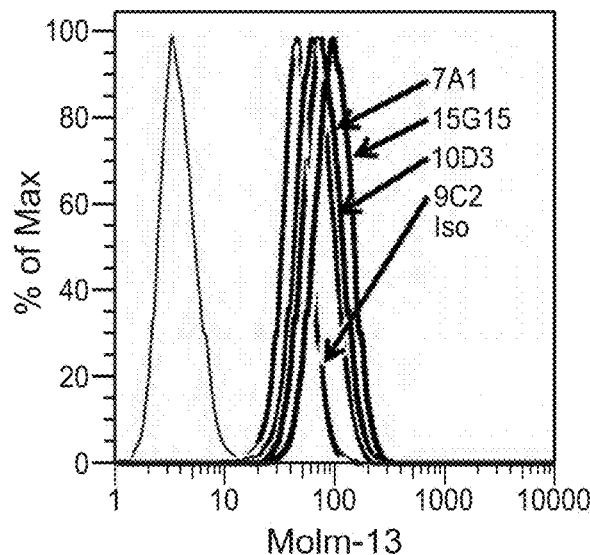
Figure 6D:
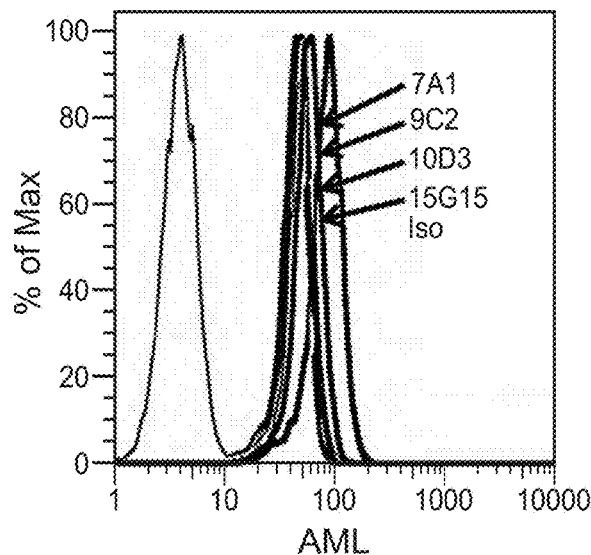
Figure 7A:
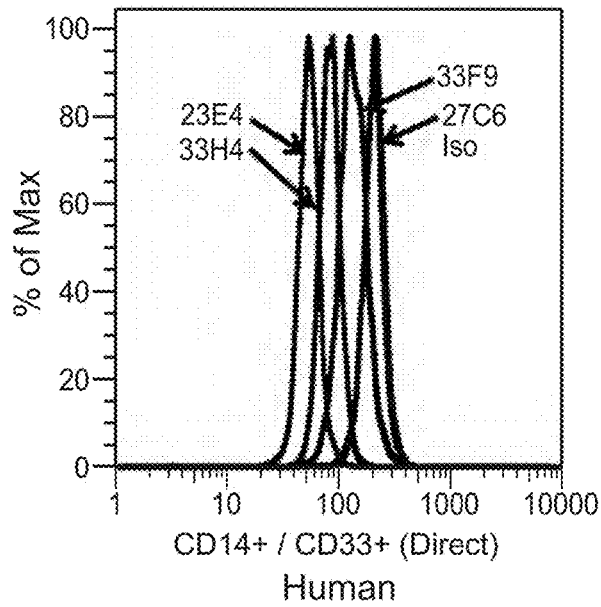
FIG. 7A-7D shows species cross-reactivity of anti-CD33 antibodies to endogenous CD33. Anti-CD33 antibody binding to huCD33+(A, C) and cynoCD33+(B, D) myeloid cells.
Figure 7B:
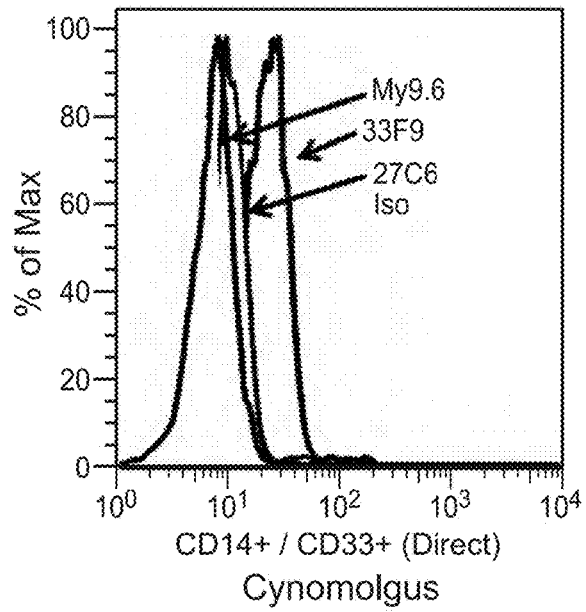
Figure 7C:
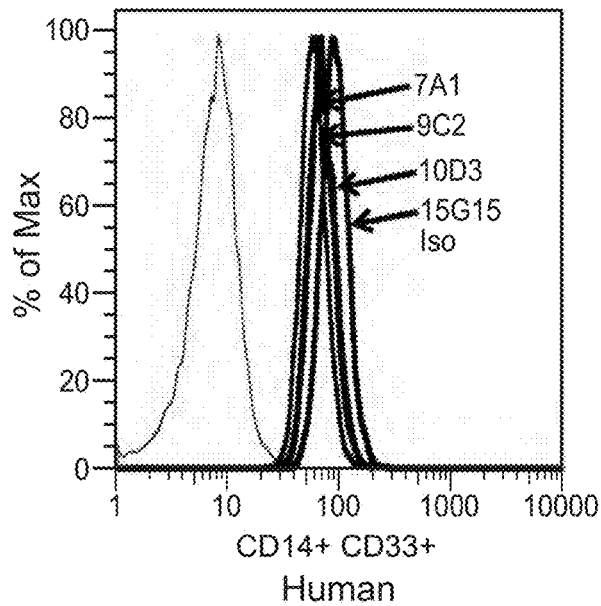
Figure 7D:
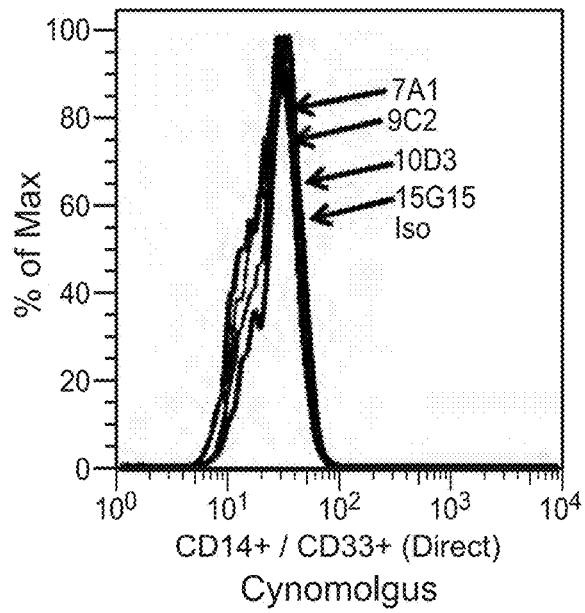

and 15G15.33 Thio-LC V205C L-D #1 at various doses in HL-60 (A) and EOL-1 (B) xenografts.

FIG. 17 shows change in tumor volume (mm³) over time upon treatment with 15G15 Thio-HC A118C L-D #2 (L-D #2 is made by conjugating the linker-drug moiety maleimide with acetal linker-PNU

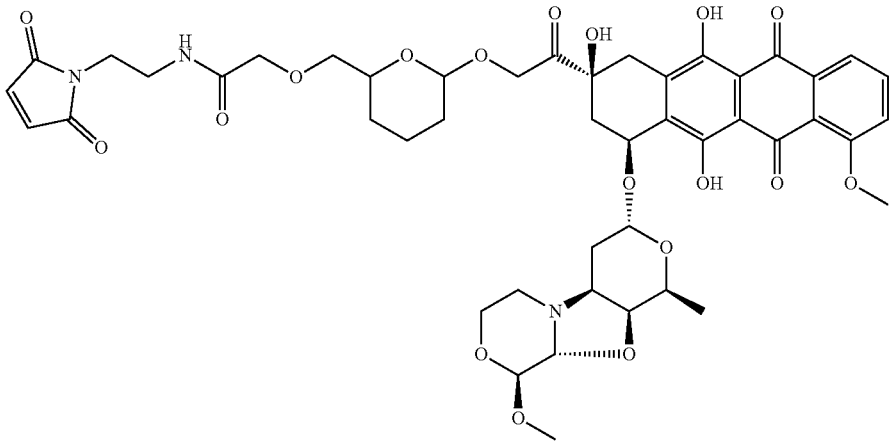 [SMILES: COc1cccc2c1C(=O)c1c(O)c3c(c(O)c1C2=O)C[C@@](O)(C(=O)COC1CCCC(COCC(=O)NCCN2C(=O)C=CC2=O)O1)C[C@@H]3O[C@H]1C[C@H]2[C@H](O[C@@H]3[C@@H](OC)OCCN32)[C@H](C)O1]

DETAILED DESCRIPTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD33 antibody" and "an antibody that binds to CD33" refer to an antibody that is capable of binding CD33 with sufficient affinity such that the antibody is useful as a diagnostic and/or therapeutic agent in targeting CD33. In one embodiment, the extent of binding of an anti-CD33 antibody to an unrelated, non-CD33 protein is less than about 10% of the binding of the antibody to CD33 as measured, e.g., by a radioimmunoassay (RIA). In certain embodiments, an antibody that binds to CD33 has a dissociation constant (Kd) of ≤1 μM, z≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-CD33 antibody binds to an epitope of CD33 that is conserved among CD33 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include acute myeloid leukemia (AML), myelodysplastic syndrome (MDS), chronic myelogenous leukemia (CML), chronic myelomonocytic leukemia, acute promyelocytic leukemia (APL), chronic myeloproliferative disorder, thrombocytic leukemia, precursor B-cell acute lymphoblastic leukemia (pre-B-ALL), precursor T-cell acute lymphoblastic leukemia (preT-ALL), multiple myeloma (MM), mast cell disease, mast cell leukemia, mast cell sarcoma, myeloid sarcomas, lymphoid leukemia, and undifferentiated leukemia. In some embodiments, the cancer is myeloid leukemia. In some embodiments, the cancer is acute myeloid leukemia (AML).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called β, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Res^{88}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of CD33" refers to naturally occurring forms of CD33 that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CD33 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "CD33," as used herein, refers to any native, mature CD33 which results from processing of a CD33 precursor protein in a cell. The term includes CD33 from any vertebrate source, including mammals such as primates (e.g. humans and cynomolgus monkeys) and rodents (e.g., mice and rats), unless otherwise indicated. The term also includes naturally occurring variants of CD33, e.g., splice variants or allelic variants. The amino acid sequence of an exemplary human CD33 precursor protein, with signal sequence (with signal sequence, amino acids 1-17) is shown in SEQ ID NO: 1. The amino acid sequence of an exemplary mature human CD33 is amino acids 18-364 of SEQ ID NO: 1. The amino acid sequence of an exemplary extracellular domain is amino acids 18-259 of SEQ ID NO: 1. The amino acid sequence of an exemplary Ig-like V-type (Ig V) domain is SEQ ID NO:2. The amino acid sequence of an exemplary Ig-like C2 type (Ig C2) domain is SEQ ID NO:3. The amino acid sequence of an exemplary cynomolgus monkey CD33 precursor protein, with signal sequence, is shown in SEQ ID NO:4.

The term "CD33-positive cancer" refers to a cancer comprising cells that express CD33 on their surface. In some embodiments, expression of CD33 on the cell surface is determined, for example, using antibodies to CD33 in a method such as immunohistochemistry, FACS, etc. Alternatively, CD33 mRNA expression is considered to correlate to CD33 expression on the cell surface and can be determined by a method selected from in situ hybridization and RT-PCR (including quantitative RT-PCR).

The term "CD33-positive cell" refers to a cell that expresses CD33 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—OCH$_3$) and ethoxy (—OCH$_2$CH$_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, sp$^2$ double bond. Examples include, but are not limited to: ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$). A "$C_2$-$C_8$ alkenyl" is a hydrocarbon containing 2 to 8 normal, secondary, tertiary or cyclic carbon atoms with at least one site of unsaturation, i.e. a carbon-carbon, sp$^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH$_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

A "$C_1$-$C_{10}$ alkylene" is a straight chain, saturated hydrocarbon group of the formula —(CH$_2$)$_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A $C_5$-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

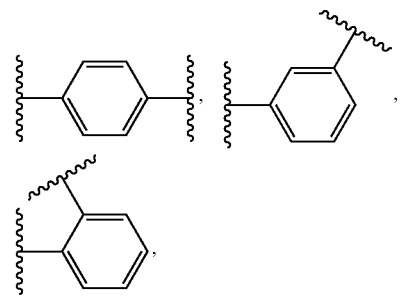

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N₃, —NH₂, —NH(R'), —N(R')₂ and —CN; wherein each R' is independently selected from H, —C₁-C₈ alkyl and aryl.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp³ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, NC(=O)R, —C(=O)R, —C(=O)NR₂, —SO₃⁻, —SO₃H, —S(=O)₂R, —OS(=O)₂OR, —S(=O)₂NR, —S(=O)R, —OP(=O)(OR)₂, —P(=O)(OR)₂, —PO⁻₃, —PO₃H₂, —C(=O)R, —C(=O)X, —C(=S)R, —CO₂R, —CO₂⁻, —C(=S)OR, —C(=O)SR, —C(=S)SR, —C(=O)NR₂, —C(=S)NR₂, —C(=NR)NR₂, where each X is independently a halogen: F, Cl, Br, or I; and each R is independently —H, C₂-C₁₈ alkyl, C₆-C₂₀ aryl, C₃-C₁₄ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "C₃-C₈ heterocycle" refers to an aromatic or non-aromatic C₃-C₈ carbocycle in which one to four of the ring carbon atoms are independently replaced with a heteroatom from the group consisting of O, S and N. Representative examples of a C₃-C₈ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A C₃-C₈ heterocycle can be unsubstituted or substituted with up to seven groups including, but not limited to, —C₁-C₈ alkyl, —O—(C₁-C₈ alkyl), -aryl, —C(O)R', —OC(O)R', —C(O)OR', —C(O)NH₂, —C(O)NHR', —C(O)N(R')₂—NHC(O)R', —S(O)₂R', —S(O)R', —OH, -halogen, —N₃, —NH₂, —NH(R'), —N(R')₂ and —CN; wherein each R' is independently selected from H, —C₁-C₈ alkyl and aryl.

"C₃-C₈ heterocyclo" refers to a C₃-C₈ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_3$-$C_{20}$ heterocycle" refers to an aromatic or non-aromatic $C_3$-$C_8$ carbocycle in which one to four of the ring carbon atoms are independently replaced with a heteroatom from the group consisting of O, S and N. A $C_3$-$C_{20}$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_{20}$ heterocyclo" refers to a $C_3$-$C_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to CD33 and immunoconjugates comprising such antibodies. Antibodies and immunoconjugates of the invention are useful, e.g., for the diagnosis or treatment of CD33-positive cancers.

A. Exemplary Anti-CD33 Antibodies

Provided herein are isolated antibodies that bind to CD33. CD33, a member of the sialic acid binding, immunoglobulinlike lectin family, is a 67-kDa glycosylated Type I transmembrane protein, which is expressed on most myeloid and monocytic leukemia cells in addition to committed myelomonocytic and erythroid progenitor cells An exemplary naturally occurring human CD33 precursor protein sequence, with signal sequence (amino acids 1-17) is provided in SEQ ID NO: 1, and the corresponding mature CD33 protein sequence corresponding to amino acids 18-364 of SEQ ID NO: 1.

In certain embodiments, an anti-CD33 antibody has at least one or more of the following characteristics, in any combination:
- a) binds to recombinant human CD33;
- b) binds to recombinant cynomolgus monkey CD33;
- c) binds to endogenous CD33 on the surface of human peripheral blood mononucleocytes (PBMCs);
- d) binds to endogenous CD33 on the surface of cynomolgus monkey PBMCs;
- e) binds to endogenous CD33 on the surface of a cancer cell;
- f) binds to endogenous CD33 on the surface of an AML cancer cell;
- g) binds to endogenous CD33 on the surface of Molm-13 cells;
- h) binds to CD33 comprising a R69G mutation;
- i) binds to CD33 Ig V domain;
- j) binds to CD33 that is void of N-linked glycosylation at N100;
- k) binds to CD33 that is void of N-linked glycosylation at N113;
- l) binds to CD33 comprising an S102A mutation;
- m) binds to CD33 comprising an S115A mutation;
- n) does not bind CD33 Ig C2 domain;
- o) competes for human CD33 binding with My9.6 antibody;
- p) competes for human CD33 binding with antibody 33H4;
- q) competes for human CD33 binding with antibody 23E4;
- r) binds to endogenous human CD33 with a Kd of less than 15 nM, less than 10 nM, less than 7 nM, less than 5 nM, or less than 3 nM;
- s) binds to recombinant human CD33 with a Kd of less than 10 nM, less than 7 nM, less than 5 nM, or less than 3 nM; and/or
- t) binds to recombinant cynomolgus monkey CD33 with a Kd of less than 10 nM, less than 7 nM, less than 5 nM, or less than 3 nM, less than 2 nM, or less than 1 nM.

In some embodiments, the characteristics of the antibody are determined as described herein in the Examples below. Nonlimiting exemplary such antibodies include 7A1, 9C2, 10D3, and 15G15, and variants thereof, described herein. In some embodiments, an antibody that binds CD33 binds both recombinant and endogenous human and cynomolgus monkey CD33 and competes for human CD33 binding with My9.6, 33H₄, and 23E4. In some embodiments, an antibody that binds CD33 binds both recombinant and endogenous human and cynomolgus monkey CD33 and competes for human CD33 binding with My9.6, but has an overlapping but distinct epitope from My9.6.

In certain embodiments, an anti-CD33 antibody has at least one or more of the following characteristics, in any combination:
- a) binds to recombinant human CD33;
- b) binds to recombinant cynomolgus monkey CD33;
- c) binds to endogenous CD33 on the surface of human peripheral blood mononucleocytes (PBMCs);
- d) binds to recombinant human CD33 with a Kd of less than 10 nM, less than 7 nM, less than 5 nM, less than 3 nM, less than 2 nM, or less than 1 nM; and/or
- e) binds to recombinant cynomolgus monkey CD33 with a Kd of less than 10 nM, less than 7 nM, less than 5 nM, less than 3 nM, less than 2 nM, or less than 1 nM.

In some embodiments, the characteristics of the antibody are determined as described herein in the Examples below. Nonlimiting exemplary such antibodies include 9C3, and variants thereof, described herein.

Antibody 7A1, 9C2, 10D3, 15G15, 15G15.33, 15G15.37, 15G15.83, 15G15.88, 15G15.7, 15G15.17, 15G15.30, 15G15.31, 15G15.39 and Other Embodiments In some embodiments, the invention provides an anti-CD33 antibody comprising at least one, two, three, four, five, or six HVRs selected from (a) HVR-H1 comprising the amino acid sequence of SEQ ID NO:8, SEQ ID NO: 11, SEQ ID NO:20, SEQ ID NO:23, and/or SEQ ID NO:30; (b) HVR-H2 comprising the amino acid sequence of SEQ ID NO:9, SEQ ID NO:12, SEQ ID NO:21, SEQ ID NO:24, SEQ ID NO:31, SEQ ID NO:32, SEQ ID NO:33, SEQ ID NO:34, or SEQ ID NO:35; (c) HVR-H3 comprising the amino acid sequence of SEQ ID NO:10, SEQ ID NO:13, SEQ ID NO:22, or SEQ ID NO:25; (d) HVR-L1 comprising the amino acid sequence of SEQ ID NO:5; (e) HVR-L2 comprising the amino acid sequence of SEQ ID NO:6, SEQ ID NO:26, SEQ ID NO:27, SEQ ID NO:28, or SEQ ID NO:29; and (f) HVR-L3 comprising the amino acid sequence of SEQ ID NO:7.

In one aspect, the invention provides an antibody comprising at least one, at least two, or all three VH HVR sequences selected from (a) HVR-H1 comprising the amino acid sequence of SEQ ID NO:8, SEQ ID NO:11, SEQ ID NO:20, SEQ ID NO:23, or SEQ ID NO:30; (b) HVR-H2 comprising the amino acid sequence of SEQ ID NO:9, SEQ ID NO:12, SEQ ID NO:21, SEQ ID NO:24, SEQ ID NO:9, SEQ ID NO:12, SEQ ID NO:21, SEQ ID NO:24, SEQ ID NO:31, SEQ ID NO:32, SEQ ID NO:33, SEQ ID NO:34, or SEQ ID NO:35; and (c) HVR-H3 comprising the amino acid sequence of SEQ ID NO:10, SEQ ID NO:13, SEQ ID NO:22, or SEQ ID NO:25. In one embodiment, the antibody comprises HVR-H3 comprising the amino acid sequence of SEQ ID NO:10, SEQ ID NO:13, SEQ ID NO:22, or SEQ ID NO:25. In another embodiment, the antibody comprises HVR-H3 comprising the amino acid sequence of SEQ ID NO:10, SEQ ID NO:13, SEQ ID NO:22, or SEQ ID NO:25 and HVR-L3 comprising the amino acid sequence of SEQ ID NO:7. In a further embodiment, the antibody comprises HVR-H3 comprising the amino acid sequence of SEQ ID NO:10, SEQ ID NO:13, SEQ ID NO:22, or SEQ ID NO:25, HVR-L3 comprising the amino acid sequence of SEQ ID NO:7, and HVR-H2 comprising the amino acid sequence of SEQ ID NO:9, SEQ ID NO: 12, SEQ ID NO:21, SEQ ID NO:24, SEQ ID NO:9, SEQ ID NO: 12, SEQ ID NO:21, SEQ ID NO:24, SEQ ID NO:31, SEQ ID NO:32, SEQ ID NO:33, SEQ ID NO:34, or SEQ ID NO:35. In a further embodiment, the antibody comprises (a) HVR-H1 comprising the amino acid sequence of SEQ ID NO:8, SEQ ID NO:11, SEQ ID NO:20, SEQ ID NO:23, or SEQ ID NO:30; (b) HVR-H2 comprising the amino acid sequence of SEQ ID NO:9, SEQ ID NO:12, SEQ ID NO:21, SEQ ID NO:24, SEQ ID NO:9, SEQ ID NO:12, SEQ ID NO:21, SEQ ID NO:24, SEQ ID NO:31, SEQ ID NO:32, SEQ ID NO:33, SEQ ID NO:34, or SEQ ID NO:35; and (c) HVR-H3 comprising the amino acid sequence of SEQ ID NO:10, SEQ ID NO:13, SEQ ID NO:22, or SEQ ID NO:25.

In another aspect, the invention provides an antibody comprising at least one, at least two, or all three VL HVR sequences selected from (a) HVR-L1 comprising the amino acid sequence of SEQ ID NO:5; (b) HVR-L2 comprising the amino acid sequence of SEQ ID NO:6, SEQ ID NO:26, SEQ ID NO:27, SEQ ID NO:28, or SEQ ID NO:29; and (c) HVR-L3 comprising the amino acid sequence of SEQ ID NO:7. In one embodiment, the antibody comprises (a) HVR-L1 comprising the amino acid sequence of SEQ ID NO:5; (b) HVR-L2 comprising the amino acid sequence of SEQ ID NO:6, SEQ ID NO:26, SEQ ID NO:27, SEQ ID NO:28, or SEQ ID NO:29; and (c) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:8, SEQ ID NO: 11, SEQ ID NO:20, SEQ ID NO:23, or SEQ ID NO:30, (ii) HVR-H$_2$ comprising the amino acid sequence of SEQ ID NO:9, SEQ ID NO:12, SEQ ID NO:21, SEQ ID NO:24, SEQ ID NO:9, SEQ ID NO:12, SEQ ID NO:21, SEQ ID NO:24, SEQ ID NO:31, SEQ ID NO:32, SEQ ID NO:33, SEQ ID NO:34, or SEQ ID NO:35; and (iii) HVR-H3 comprising an amino acid sequence selected from SEQ ID NO:10, SEQ ID NO:13, SEQ ID NO:22, or SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, SEQ ID NO:26, SEQ ID NO:27, SEQ ID NO:28, or SEQ ID NO:29, and (c) HVR-L3 comprising the amino acid sequence of SEQ ID NO:7.

In another aspect, the invention provides an antibody comprising (a) HVR-H1 comprising the amino acid sequence of SEQ ID NO:8, SEQ ID NO:11, SEQ ID NO:20, SEQ ID NO:23, and/or SEQ ID NO:30; (b) HVR-H2 comprising the amino acid sequence of SEQ ID NO:9, SEQ ID NO: 12, SEQ ID NO:21, and/or SEQ ID NO:24; (c) HVR-H3 comprising the amino acid sequence of SEQ ID NO: 10, SEQ ID NO:13, SEQ ID NO:22, SEQ ID NO:25, SEQ ID NO:31, SEQ ID NO:32, SEQ ID NO:33, SEQ ID NO:34, and/or SEQ ID NO:35; (d) HVR-L1 comprising the amino acid sequence of SEQ ID NO:5; (e) HVR-L2 comprising the amino acid sequence of SEQ ID NO:6, SEQ ID NO:26, SEQ ID NO:27, SEQ ID NO:28, and/or SEQ ID NO:29; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:112, (ii) HVR-H2 comprising the amino acid sequence of SEQ ID NO:113, and (iii) HVR-H3 comprising an amino acid sequence selected from SEQ ID NO: 114; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO: 111, and (c) HVR-L3 comprising the amino acid sequence of SEQ ID NO:7.

In another aspect, the invention provides an antibody comprising (a) HVR-H1 comprising the amino acid sequence of SEQ ID NO: 112; (b) HVR-H2 comprising the amino acid sequence of SEQ ID NO: 113; (c) HVR-H3 comprising the amino acid sequence of SEQ ID NO: 114; (d) HVR-L1 comprising the amino acid sequence of SEQ ID NO:5; (e) HVR-L2 comprising the amino acid sequence of SEQ ID NO: 111; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:115, (ii) HVR-H2 comprising the amino acid sequence of SEQ ID NO:116, and (iii) HVR-H3 comprising an amino acid sequence selected from SEQ ID NO: 117; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:118, (ii) HVR-H2 comprising the amino acid sequence of SEQ ID NO:119, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO: 111, and (c) HVR-L3 comprising the amino acid sequence of SEQ ID NO:7.

In another aspect, the invention provides an antibody comprising (a) HVR-H1 comprising the amino acid sequence of SEQ ID NO: 118; (b) HVR-H2 comprising the amino acid sequence of SEQ ID NO: 119; (c) HVR-H3 comprising the amino acid sequence of SEQ ID NO:25; (d) HVR-L1 comprising the amino acid sequence of SEQ ID NO: 5; (e) HVR-L2 comprising the amino acid sequence of SEQ ID NO: 111; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:8, (ii) HVR-H2 comprising the amino acid sequence of SEQ ID NO:9, and (iii) HVR-H3 comprising an amino acid sequence selected from SEQ ID NO: 10; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:8; (b) HVR-H2 comprising the amino acid sequence of SEQ ID NO:9; (c) HVR-H3 comprising the amino acid sequence of SEQ ID NO: 10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO: 11, (ii) HVR-H2 comprising the amino acid sequence of SEQ ID NO: 12, and (iii) HVR-H3 comprising an amino acid sequence selected from SEQ ID NO: 13; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO: 11; (b) HVR-H2 comprising the amino acid sequence of SEQ ID NO: 12; (c) HVR-H3 comprising the amino acid sequence of SEQ ID NO: 13; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:20, (ii) HVR-H2 comprising the amino acid sequence of SEQ ID NO:21, and (iii) HVR-H3 comprising an amino acid sequence selected from SEQ ID NO:22; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:20; (b) HVR-H2 comprising the amino acid sequence of SEQ ID NO:21; (c) HVR-H3 comprising the amino acid sequence of SEQ ID NO:22; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:24, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:24, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:26, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:26; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:24, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:27, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:27; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:24, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:28, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:28; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:24, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:29, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:29; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:30, (ii) HVR-H2 comprising the amino acid sequence of SEQ ID NO:24, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:30; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:31, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:31; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:32, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:32; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:33, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:33; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:34, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:34; (c) HVR-H3 comprising the amino acid sequence of SEQ ID NO:25; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:35, and (iii) HVR-H3 comprising an amino acid sequence selected from SEQ ID NO:25; and (b) a VL domain comprising at least one, at least two, or all three VL HVR sequences selected from (i) HVR-L1 comprising the amino acid sequence of SEQ ID NO: 5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:23; (b) HVR-H2 comprising the amino acid sequence of SEQ ID NO:35; (c) HVR-H3 comprising the amino acid sequence of SEQ ID NO:25; (d) HVR-L1 comprising the amino acid sequence of SEQ ID NO: 5; (e) HVR-L2 comprising the amino acid sequence of SEQ ID NO: 6; and (f) HVR-L3 comprising the amino acid sequence of SEQ ID NO:7.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:66, SEQ ID NO:68, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, or SEQ ID NO:100. In certain embodiments, a VH sequence having at least 90%, 91%, 92%, 93%, 94%, 95%, 96%, 97%, 98%, or 99% identity to the amino acid sequence of SEQ ID NO:66, SEQ ID NO:68, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, and/or SEQ ID NO:100 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:66, SEQ ID NO:68, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, and/or SEQ ID NO: 100. In certain embodiments, a total of 1 to 5 amino acids have been substituted, inserted and/or deleted in SEQ ID NO:66, SEQ ID NO:68, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, and/or SEQ ID NO:100. In certain embodiments, substitutions, insertions, or deletions occur in regions outside the HVRs (i.e., in the FRs). Optionally, the anti-CD33 antibody comprises the VH sequence of SEQ ID NO:66, SEQ ID NO:68, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, or SEQ ID NO: 100, including post-translational modifications of that sequence. In a particular embodiment, the VH comprises one, two or three HVRs selected from: (a) HVR-H1 comprising the amino acid sequence of SEQ ID NO:8, SEQ ID NO: 11, SEQ ID NO:20, SEQ ID NO:23, or SEQ ID NO:30; (b) HVR-H2 comprising the amino acid sequence of SEQ ID NO:9, SEQ ID NO:12, SEQ ID NO:21, SEQ ID NO:24, SEQ ID NO:31, SEQ ID NO:32, SEQ ID NO:33, SEQ ID NO:34, or SEQ ID NO:35; and (c) HVR-H3 comprising the amino acid sequence of SEQ ID NO:10, SEQ ID NO:13, SEQ ID NO:22, or SEQ ID NO:25.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:65, SEQ ID NO:67, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, and/or SEQ ID NO:99. In certain embodiments, a VL sequence having at least 90%, 91%, 92%, 93%, 94%, 95%, 96%, 97%, 98%, or 99% identity to the amino acid sequence of SEQ ID NO:65, SEQ ID NO:67, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, or SEQ ID NO:99 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:65, SEQ ID NO:67, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, and/or SEQ ID NO:99. In certain embodiments, a total of 1 to 5 amino acids have been substituted, inserted and/or deleted in SEQ ID NO:65, SEQ ID NO:67, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, and/or SEQ ID NO:99. In certain embodiments, the substitutions, insertions, or deletions occur in regions outside the HVRs (i.e., in the FRs). Optionally, the anti-CD33 antibody comprises the VL sequence of SEQ ID NO:65, SEQ ID NO:67, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, or SEQ ID NO:99, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6, SEQ ID NO:26, SEQ ID NO:27, SEQ ID NO:28, or SEQ ID NO:29; and (c) HVR-L3 comprising the amino acid sequence of SEQ ID NO:7.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO:66 and SEQ ID NO:65, respectively, including post-translational modifications of those sequences. In one embodiment, the antibody comprises the VH and VL sequences in SEQ ID NO:68 and SEQ ID NO:67, respectively, including post-translational modifications of those sequences. In one embodiment, the antibody comprises the VH and VL sequences in SEQ ID NO:78 and SEQ ID NO:77, respectively, including post-translational modifications of those sequences. In one embodiment, the antibody comprises the VH and VL sequences in SEQ ID NO:80 and SEQ ID NO:79, respectively, including post-translational modifications of those sequences. In one embodiment, the antibody comprises the VH and VL sequences in SEQ ID NO:82 and SEQ ID NO:81, respectively, including post-translational modifications of those sequences. In one embodiment, the antibody comprises the VH and VL sequences in SEQ ID NO:84 and SEQ ID NO:83, respectively, including post-translational modifications of those sequences. In one embodiment, the antibody comprises the VH and VL sequences in SEQ ID NO:86 and SEQ ID NO:85, respectively, including post-translational modifications of those sequences. In one embodiment, the antibody comprises the VH and VL sequences in SEQ ID NO:88 and SEQ ID NO:87, respectively, including post-translational modifications of those sequences. In one embodiment, the antibody comprises the VH and VL sequences in SEQ ID NO:90 and SEQ ID NO:89, respectively, including post-translational modifications of those sequences. In one embodiment, the antibody comprises the VH and VL sequences in SEQ ID NO:92 and SEQ ID NO:91, respectively, including post-translational modifications of those sequences. In one embodiment, the antibody comprises the VH and VL sequences in SEQ ID NO:94 and SEQ ID NO:93, respectively, including post-translational modifications of those sequences. In one embodiment, the antibody comprises the VH and VL sequences in SEQ ID NO:96 and SEQ ID NO:95, respectively, including post-translational modifications of those sequences. In one embodiment, the antibody comprises the VH and VL sequences in SEQ ID NO:98 and SEQ ID NO:97, respectively, including post-translational modifications of those sequences. In one embodiment, the antibody comprises the VH and VL sequences in SEQ ID NO: 100 and SEQ ID NO:99, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO:66, SEQ ID NO:68, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, or SEQ ID NO: 100 and a VL sequence of SEQ ID NO:65, SEQ ID NO:67, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, or SEQ ID NO:99, respectively.

Provided herein are antibodies comprising a light chain variable domain comprising the HVR1-LC, HVR2-LC and HVR3-LC sequence according to Kabat numbering as depicted in FIGS. 1A and/or 2A and a heavy chain variable domain comprising the HVR1-HC, HVR2-HC and HVR3-HC sequence according to Kabat numbering as depicted in FIGS. 1B and/or 2B. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIGS. 1A and/or 2A. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIGS. 1B and/or 2B.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

Antibody 9C3 and Other Embodiments

In some embodiments, the invention provides an anti-CD33 antibody comprising at least one, two, three, four, five, or six HVRs selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19; (d) HVR-L1 comprising the amino acid sequence of SEQ ID NO: 14; (e) HVR-L2 comprising the amino acid sequence of SEQ ID NO: 15; and (f) HVR-L3 comprising the amino acid sequence of SEQ ID NO:16.

In one aspect, the invention provides an antibody comprising at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 19. In one embodiment, the antibody comprises HVR-H3 comprising the amino acid sequence of SEQ ID NO: 19. In another embodiment, the antibody comprises HVR-H3 comprising the amino acid sequence of SEQ ID NO: 19 and HVR-L3 comprising the amino acid sequence of SEQ ID NO: 16. In a further embodiment, the antibody comprises HVR-H3 comprising the amino acid sequence of SEQ ID NO: 19, HVR-L3 comprising the amino acid sequence of SEQ ID NO: 16, and HVR-H2 comprising the amino acid sequence of SEQ ID NO: 18. In a further embodiment, the antibody comprises (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO:19.

In another aspect, the invention provides an antibody comprising at least one, at least two, or all three VL HVR sequences selected from (a) HVR-L1 comprising the amino acid sequence of SEQ ID NO: 14; (b) HVR-L2 comprising the amino acid sequence of SEQ ID NO: 15; and (c) HVR-L3 comprising the amino acid sequence of SEQ ID NO: 16. In one embodiment, the antibody comprises (a) HVR-L1 comprising the amino acid sequence of SEQ ID NO: 14; (b) HVR-L2 comprising the amino acid sequence of SEQ ID NO:15; and (c) HVR-L3 comprising the amino acid sequence of SEQ ID NO:16.

In another aspect, an antibody of the invention comprises (a) a VH domain comprising at least one, at least two, or all three VH HVR sequences selected from (i) HVR-H1 comprising the amino acid sequence of SEQ ID NO: 17, (ii)

HVR-H2 comprising the amino acid sequence of SEQ ID NO: 18, and (iii) HVR-H3 comprising an amino acid sequence selected from SEQ ID NO: 19; and (b) a VL domain comprising at least one, at least two, or all three VL HVR sequences selected from (i) HVR-L1 comprising the amino acid sequence of SEQ ID NO: 14, (ii) HVR-L2 comprising the amino acid sequence of SEQ ID NO: 15, and (c) HVR-L3 comprising the amino acid sequence of SEQ ID NO: 16.

In another aspect, the invention provides an antibody comprising (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19; (d) HVR-L1 comprising the amino acid sequence of SEQ ID NO: 14; (e) HVR-L2 comprising the amino acid sequence of SEQ ID NO: 15; and (f) HVR-L3 comprising the amino acid sequence of SEQ ID NO: 16.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:70, SEQ ID NO:72, SEQ ID NO:74, and/or SEQ ID NO:76. In certain embodiments, a VH sequence having at least 90%, 91%, 92%, 93%, 94%, 95%, 96%, 97%, 98%, or 99% identity to the amino acid sequence of SEQ ID NO:70, SEQ ID NO:72, SEQ ID NO:74, and/or SEQ ID NO:76 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:70, SEQ ID NO:72, SEQ ID NO:74, and/or SEQ ID NO:76. In certain embodiments, a total of 1 to 5 amino acids have been substituted, inserted and/or deleted in SEQ ID NO:70, SEQ ID NO:72, SEQ ID NO:74, and/or SEQ ID NO:76. In certain embodiments, substitutions, insertions, or deletions occur in regions outside the HVRs (i.e., in the FRs). Optionally, the anti-CD33 antibody comprises the VH sequence of SEQ ID NO:70, SEQ ID NO:72, SEQ ID NO:74, or SEQ ID NO:76, including post-translational modifications of that sequence. In a particular embodiment, the VH comprises one, two or three HVRs selected from: (a) HVR-H1 comprising the amino acid sequence of SEQ ID NO: 17, (b) HVR-H2 comprising the amino acid sequence of SEQ ID NO: 18, and (c) HVR-H3 comprising the amino acid sequence of SEQ ID NO:19.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:69, SEQ ID NO:71, SEQ ID NO:73, and/or SEQ ID NO:75. In certain embodiments, a VL sequence having at least 90%, 91%, 92%, 93%, 94%, 95%, 96%, 97%, 98%, or 99% identity to the amino acid sequence of SEQ ID NO:69, SEQ ID NO:71, SEQ ID NO:73, and/or SEQ ID NO:75 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:69, SEQ ID NO:71, SEQ ID NO:73, and/or SEQ ID NO:75. In certain embodiments, a total of 1 to 5 amino acids have been substituted, inserted and/or deleted in SEQ ID NO:69, SEQ ID NO:71, SEQ ID NO:73, and/or SEQ ID NO:75. In certain embodiments, the substitutions, insertions, or deletions occur in regions outside the HVRs (i.e., in the FRs). Optionally, the anti-CD33 antibody comprises the VL sequence of SEQ ID NO:69, SEQ ID NO:71, SEQ ID NO:73, or SEQ ID NO:75, including post-translational modifications of that sequence. In a particular embodiment, the VL comprises one, two or three HVRs selected from (a) HVR-L1 comprising the amino acid sequence of SEQ ID NO: 14; (b) HVR-L2 comprising the amino acid sequence of SEQ ID NO: 15; and (c) HVR-L3 comprising the amino acid sequence of SEQ ID NO: 16.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO:70 and SEQ ID NO:69, respectively, including post-translational modifications of those sequences. In one embodiment, the antibody comprises the VH and VL sequences in SEQ ID NO:72 and SEQ ID NO:71, respectively, including post-translational modifications of those sequences. In one embodiment, the antibody comprises the VH and VL sequences in SEQ ID NO:74 and SEQ ID NO:73, respectively, including post-translational modifications of those sequences. In one embodiment, the antibody comprises the VH and VL sequences in SEQ ID NO:76 and SEQ ID NO:75, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO:70, SEQ ID NO:72, SEQ ID NO:74, and SEQ ID NO:76 and a VL sequence of SEQ ID NO:69, SEQ ID NO:71, SEQ ID NO:73, and SEQ ID NO:75, respectively.

Provided herein are antibodies comprising a light chain variable domain comprising the HVR1-LC, HVR2-LC and HVR3-LC sequence according to Kabat numbering as depicted in FIG. 4A and a heavy chain variable domain comprising the HVR1-HC, HVR2-HC and HVR3-HC sequence according to Kabat numbering as depicted in FIG. 4B. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 4A. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 4B.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

Antibody 23E4 and Other Embodiments

In some embodiments, the invention provides an anti-CD33 antibody comprising at least one, two, three, four, five, or six HVRs selected from (a) HVR-H1 comprising the amino acid sequence of SEQ ID NO:39; (b) HVR-H2 comprising the amino acid sequence of SEQ ID NO:40; (c) HVR-H3 comprising the amino acid sequence of SEQ ID NO:41; (d) HVR-L1 comprising the amino acid sequence of SEQ ID NO:36; (e) HVR-L2 comprising the amino acid sequence of SEQ ID NO:37; and (f) HVR-L3 comprising the amino acid sequence of SEQ ID NO:38.

In one aspect, the invention provides an antibody comprising at least one, at least two, or all three VH HVR sequences selected from (a) HVR-H1 comprising the amino acid sequence of SEQ ID NO:39; (b) HVR-H2 comprising the amino acid sequence of SEQ ID NO:40; and (c) HVR-H3 comprising the amino acid sequence of SEQ ID NO:41. In one embodiment, the antibody comprises HVR-H3 comprising the amino acid sequence of SEQ ID NO:41. In another embodiment, the antibody comprises HVR-H3 comprising the amino acid sequence of SEQ ID NO:41 and HVR-L3 comprising the amino acid sequence of SEQ ID NO:38. In a further embodiment, the antibody comprises HVR-H3 comprising the amino acid sequence of SEQ ID NO:41, HVR-L3 comprising the amino acid sequence of SEQ ID NO:38, and HVR-H2 comprising the amino acid sequence of SEQ ID NO:40. In a further embodiment, the antibody comprises (a) HVR-H1 comprising the amino acid sequence of SEQ ID NO:39; (b) HVR-H2 comprising the amino acid sequence of SEQ ID NO:40; and (c) HVR-H3 comprising the amino acid sequence of SEQ ID NO:41.

In another aspect, the invention provides an antibody comprising at least one, at least two, or all three VL HVR sequences selected from (a) HVR-L1 comprising the amino acid sequence of SEQ ID NO:36; (b) HVR-L2 comprising the amino acid sequence of SEQ ID NO:37; and (c) HVR-L3 comprising the amino acid sequence of SEQ ID NO:38. In one embodiment, the antibody comprises (a) HVR-L1 comprising the amino acid sequence of SEQ ID NO:36; (b) HVR-L2 comprising the amino acid sequence of SEQ ID NO:37; and (c) HVR-L3 comprising the amino acid sequence of SEQ ID NO:38.

In another aspect, an antibody of the invention comprises (a) a VH domain comprising at least one, at least two, or all three VH HVR sequences selected from (i) HVR-H1 comprising the amino acid sequence of SEQ ID NO:39, (ii) HVR-H2 comprising the amino acid sequence of SEQ ID NO:40, and (iii) HVR-H3 comprising an amino acid sequence selected from SEQ ID NO:41; and (b) a VL domain comprising at least one, at least two, or all three VL HVR sequences selected from (i) HVR-L1 comprising the amino acid sequence of SEQ ID NO:36, (ii) HVR-L2 comprising the amino acid sequence of SEQ ID NO:37, and (c) HVR-L3 comprising the amino acid sequence of SEQ ID NO:38.

In another aspect, the invention provides an antibody comprising (a) HVR-H1 comprising the amino acid sequence of SEQ ID NO:39; (b) HVR-H2 comprising the amino acid sequence of SEQ ID NO:40; (c) HVR-H3 comprising the amino acid sequence of SEQ ID NO:41; (d) HVR-L1 comprising the amino acid sequence of SEQ ID NO:36; (e) HVR-L2 comprising the amino acid sequence of SEQ ID NO:37; and (f) HVR-L3 comprising the amino acid sequence of SEQ ID NO:38.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 102. In certain embodiments, a VH sequence having at least 90%, 91%, 92%, 93%, 94%, 95%, 96%, 97%, 98%, or 99% identity to the amino acid sequence of SEQ ID NO: 102 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 102. In certain embodiments, a total of 1 to 5 amino acids have been substituted, inserted and/or deleted in SEQ ID NO: 102. In certain embodiments, substitutions, insertions, or deletions occur in regions outside the HVRs (i.e., in the FRs). Optionally, the anti-CD33 antibody comprises the VH sequence of SEQ ID NO: 102, including post-translational modifications of that sequence. In a particular embodiment, the VH comprises one, two or three HVRs selected from: (a) HVR-H1 comprising the amino acid sequence of SEQ ID NO:39, (b) HVR-H2 comprising the amino acid sequence of SEQ ID NO:40, and (c) HVR-H3 comprising the amino acid sequence of SEQ ID NO:41.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:101. In certain embodiments, a VL sequence having at least 90%, 91%, 92%, 93%, 94%, 95%, 96%, 97%, 98%, or 99% identity to the amino acid sequence of SEQ ID NO:101 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:101. In certain embodiments, a total of 1 to 5 amino acids have been substituted, inserted and/or deleted in SEQ ID NO:101. In certain embodiments, the substitutions, insertions, or deletions occur in regions outside the HVRs (i.e., in the FRs). Optionally, the anti-CD33 antibody comprises the VL sequence of SEQ ID NO: 101, including post-translational modifications of that sequence. In a particular embodiment, the VL comprises one, two or three HVRs selected from (a) HVR-L1 comprising the amino acid sequence of SEQ ID NO:36; (b) HVR-L2 comprising the amino acid sequence of SEQ ID NO:37; and (c) HVR-L3 comprising the amino acid sequence of SEQ ID NO:38.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO: 102 and SEQ ID NO: 101, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO: 102 and a VL sequence of SEQ ID NO:101.

Figure 3A:
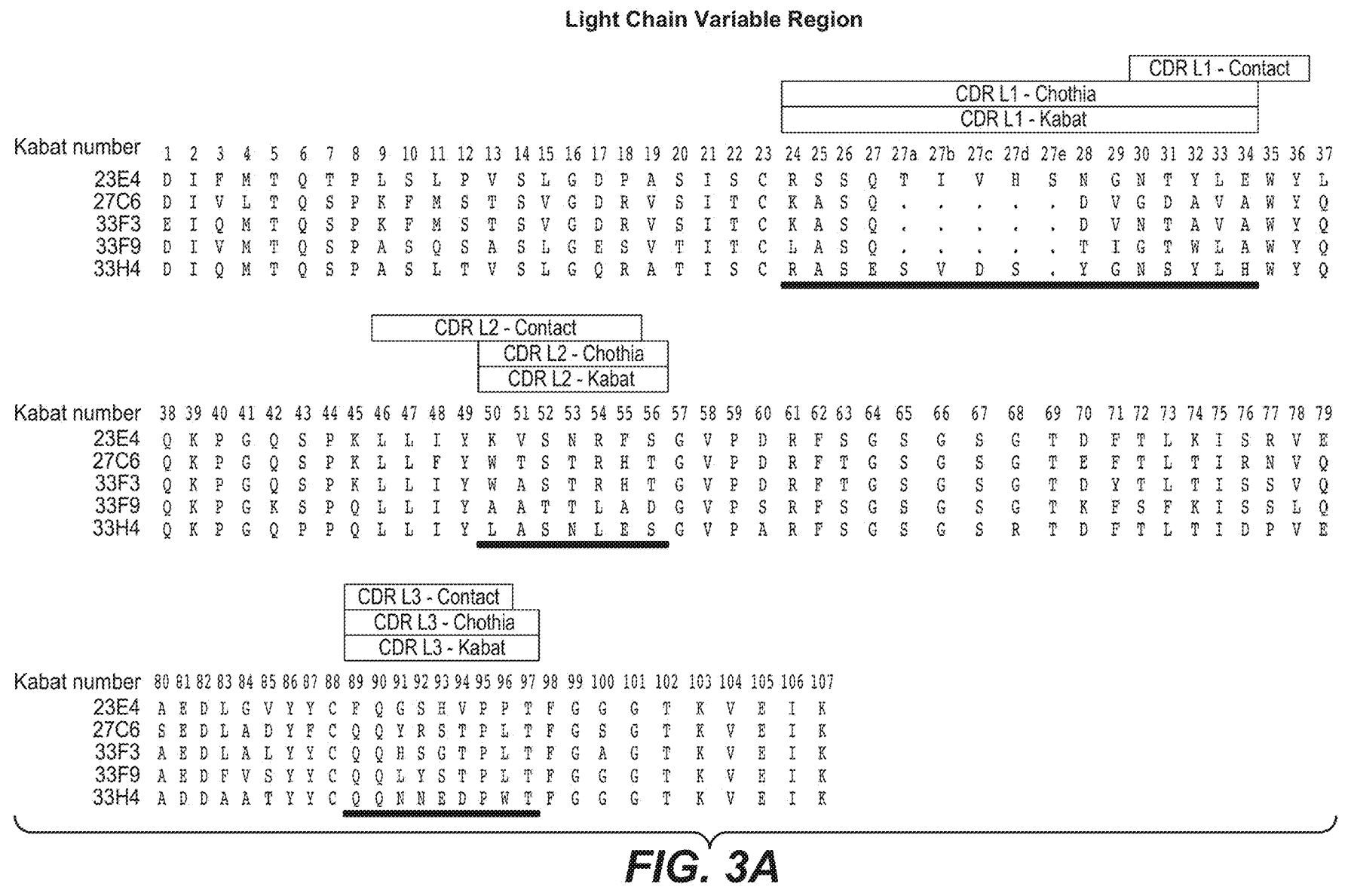

Provided herein are 23E4 antibodies comprising a light chain variable domain comprising the HVR1-LC, HVR2-LC and HVR3-LC sequence according to Kabat numbering as depicted in FIG. 3A and a heavy chain variable domain comprising the HVR1-HC, HVR2-HC and HVR3-HC sequence according to Kabat numbering as depicted in FIG. 3B. In some embodiments, the 23E4 antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 3A. In some embodiments, the 23E4 antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 3B.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

Antibody 27C6 and Other Embodiments

In some embodiments, the invention provides an anti-CD33 antibody comprising at least one, two, three, four, five, or six HVRs selected from (a) HVR-H1 comprising the amino acid sequence of SEQ ID NO:45; (b) HVR-H2 comprising the amino acid sequence of SEQ ID NO:46; (c) HVR-H3 comprising the amino acid sequence of SEQ ID NO:47; (d) HVR-L1 comprising the amino acid sequence of SEQ ID NO:42; (e) HVR-L2 comprising the amino acid sequence of SEQ ID NO:43; and (f) HVR-L3 comprising the amino acid sequence of SEQ ID NO:44.

In one aspect, the invention provides an antibody comprising at least one, at least two, or all three VH HVR sequences selected from (a) HVR-H1 comprising the amino acid sequence of SEQ ID NO:45; (b) HVR-H2 comprising the amino acid sequence of SEQ ID NO:46; and (c) HVR-H3 comprising the amino acid sequence of SEQ ID NO:47. In one embodiment, the antibody comprises HVR-H3 comprising the amino acid sequence of SEQ ID NO:47. In another embodiment, the antibody comprises HVR-H3 comprising the amino acid sequence of SEQ ID NO:47 and HVR-L3 comprising the amino acid sequence of SEQ ID NO:44. In a further embodiment, the antibody comprises HVR-H3 comprising the amino acid sequence of SEQ ID NO:47, HVR-L3 comprising the amino acid sequence of SEQ ID NO:44, and HVR-H2 comprising the amino acid sequence of SEQ ID NO:46. In a further embodiment, the antibody comprises (a) HVR-H1 comprising the amino acid sequence of SEQ ID NO:45; (b) HVR-H2 comprising the amino acid sequence of SEQ ID NO:46; and (c) HVR-H3 comprising the amino acid sequence of SEQ ID NO:47.

In another aspect, the invention provides an antibody comprising at least one, at least two, or all three VL HVR sequences selected from (a) HVR-L1 comprising the amino acid sequence of SEQ ID NO:42; (b) HVR-L2 comprising the amino acid sequence of SEQ ID NO:43; and (c) HVR-L3 comprising the amino acid sequence of SEQ ID NO:44. In one embodiment, the antibody comprises (a) HVR-L1 comprising the amino acid sequence of SEQ ID NO:42; (b) HVR-L2 comprising the amino acid sequence of SEQ ID NO:43; and (c) HVR-L3 comprising the amino acid sequence of SEQ ID NO:44.

In another aspect, an antibody of the invention comprises (a) a VH domain comprising at least one, at least two, or all three VH HVR sequences selected from (i) HVR-H1 comprising the amino acid sequence of SEQ ID NO:45, (ii) HVR-H2 comprising the amino acid sequence of SEQ ID NO:46, and (iii) HVR-H3 comprising an amino acid sequence selected from SEQ ID NO:47; and (b) a VL domain comprising at least one, at least two, or all three VL HVR sequences selected from (i) HVR-L1 comprising the amino acid sequence of SEQ ID NO:42, (ii) HVR-L2 comprising the amino acid sequence of SEQ ID NO:43, and (c) HVR-L3 comprising the amino acid sequence of SEQ ID NO:44.

In another aspect, the invention provides an antibody comprising (a) HVR-H1 comprising the amino acid sequence of SEQ ID NO:45; (b) HVR-H2 comprising the amino acid sequence of SEQ ID NO:46; (c) HVR-H3 comprising the amino acid sequence of SEQ ID NO:47; (d) HVR-L1 comprising the amino acid sequence of SEQ ID NO:42; (e) HVR-L2 comprising the amino acid sequence of SEQ ID NO:43; and (f) HVR-L3 comprising the amino acid sequence of SEQ ID NO:44.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus (VL$_{KI}$) framework and/or the VH framework VH$_1$. In certain embodiments, the human acceptor framework is the human VL kappa I consensus (VL$_{KI}$) framework and/or the VH framework VH$_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 104. In certain embodiments, a VH sequence having at least 90%, 91%, 92%, 93%, 94%, 95%, 96%, 97%, 98%, or 99% identity to the amino acid sequence of SEQ ID NO: 104 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 104. In certain embodiments, a total of 1 to 5 amino acids have been substituted, inserted and/or deleted in SEQ ID NO: 104. In certain embodiments, substitutions, insertions, or deletions occur in regions outside the HVRs (i.e., in the FRs). Optionally, the anti-CD33 antibody comprises the VH sequence of SEQ ID NO: 104, including post-translational modifications of that sequence. In a particular embodiment, the VH comprises one, two or three HVRs selected from: (a) HVR-H1 comprising the amino acid sequence of SEQ ID NO:45, (b) HVR-H2 comprising the amino acid sequence of SEQ ID NO:46, and (c) HVR-H3 comprising the amino acid sequence of SEQ ID NO:47.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 103. In certain embodiments, a VL sequence having at least 90%, 91%, 92%, 93%, 94%, 95%, 96%, 97%, 98%, or 99% identity to the amino acid sequence of SEQ ID NO: 103 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 103. In certain embodiments, a total of 1 to 5 amino acids have been substituted, inserted and/or deleted in SEQ ID NO: 103. In certain embodiments, the substitutions, insertions, or deletions occur in regions outside the HVRs (i.e., in the FRs). Optionally, the anti-CD33 antibody comprises the VL sequence of SEQ ID NO: 103, including post-translational modifications of that sequence. In a particular embodiment, the VL comprises one, two or three HVRs selected from (a) HVR-L1 comprising the amino acid sequence of SEQ ID NO:42; (b) HVR-L2 comprising the amino acid sequence of SEQ ID NO:43; and (c) HVR-L3 comprising the amino acid sequence of SEQ ID NO:44.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO: 104 and SEQ ID NO: 103, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO: 104 and a VL sequence of SEQ ID NO:103.

Provided herein are 27C6 antibodies comprising a light chain variable domain comprising the HVR1-LC, HVR2-LC and HVR3-LC sequence according to Kabat numbering as depicted in FIG. 3A and a heavy chain variable domain comprising the HVR1-HC, HVR2-HC and HVR3-HC sequence according to Kabat numbering as depicted in FIG. 3B. In some embodiments, the 27C6 antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 3A. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 3B.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

Antibody 33F3 and Other Embodiments

In some embodiments, the invention provides an anti-CD33 antibody comprising at least one, two, three, four, five, or six HVRs selected from (a) HVR-H1 comprising the amino acid sequence of SEQ ID NO:45; (b) HVR-H2 comprising the amino acid sequence of SEQ ID NO:51; (c) HVR-H3 comprising the amino acid sequence of SEQ ID NO:52; (d) HVR-L1 comprising the amino acid sequence of SEQ ID NO:48; (e) HVR-L2 comprising the amino acid sequence of SEQ ID NO:49; and (f) HVR-L3 comprising the amino acid sequence of SEQ ID NO:50.

In one aspect, the invention provides an antibody comprising at least one, at least two, or all three VH HVR sequences selected from (a) HVR-H1 comprising the amino acid sequence of SEQ ID NO:45; (b) HVR-H2 comprising the amino acid sequence of SEQ ID NO:51; and (c) HVR-H3 comprising the amino acid sequence of SEQ ID NO:52. In one embodiment, the antibody comprises HVR-H3 comprising the amino acid sequence of SEQ ID NO:52. In another embodiment, the antibody comprises HVR-H3 comprising the amino acid sequence of SEQ ID NO:52 and HVR-L3 comprising the amino acid sequence of SEQ ID NO:50. In a further embodiment, the antibody comprises HVR-H3 comprising the amino acid sequence of SEQ ID NO:52, HVR-L3 comprising the amino acid sequence of SEQ ID NO:50, and HVR-H2 comprising the amino acid sequence of SEQ ID NO: 51. In a further embodiment, the antibody comprises (a) HVR-H1 comprising the amino acid sequence of SEQ ID NO:45; (b) HVR-H2 comprising the amino acid sequence of SEQ ID NO:51; and (c) HVR-H3 comprising the amino acid sequence of SEQ ID NO:52.

In another aspect, the invention provides an antibody comprising at least one, at least two, or all three VL HVR sequences selected from (a) HVR-L1 comprising the amino acid sequence of SEQ ID NO:48; (b) HVR-L2 comprising the amino acid sequence of SEQ ID NO:49; and (c) HVR-L3 comprising the amino acid sequence of SEQ ID NO:50. In one embodiment, the antibody comprises (a) HVR-L1 comprising the amino acid sequence of SEQ ID NO:48; (b) HVR-L2 comprising the amino acid sequence of SEQ ID NO:49; and (c) HVR-L3 comprising the amino acid sequence of SEQ ID NO:50.

In another aspect, an antibody of the invention comprises (a) a VH domain comprising at least one, at least two, or all three VH HVR sequences selected from (i) HVR-H1 comprising the amino acid sequence of SEQ ID NO:45, (ii) HVR-H2 comprising the amino acid sequence of SEQ ID NO:51, and (iii) HVR-H3 comprising an amino acid sequence selected from SEQ ID NO: 52; and (b) a VL domain comprising at least one, at least two, or all three VL HVR sequences selected from (i) HVR-L1 comprising the amino acid sequence of SEQ ID NO:48, (ii) HVR-L2 comprising the amino acid sequence of SEQ ID NO:49, and (c) HVR-L3 comprising the amino acid sequence of SEQ ID NO:50.

In another aspect, the invention provides an antibody comprising (a) HVR-H1 comprising the amino acid sequence of SEQ ID NO:45; (b) HVR-H2 comprising the amino acid sequence of SEQ ID NO:51; (c) HVR-H3 comprising the amino acid sequence of SEQ ID NO:52; (d) HVR-L1 comprising the amino acid sequence of SEQ ID NO:48; (e) HVR-L2 comprising the amino acid sequence of SEQ ID NO:49; and (f) HVR-L3 comprising the amino acid sequence of SEQ ID NO:50.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus (VL$_{KI}$) framework and/or the VH framework VH$_1$. In certain embodiments, the human acceptor framework is the human VL kappa I consensus (VL$_{KI}$) framework and/or the VH framework VH$_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 106. In certain embodiments, a VH sequence having at least 90%, 91%, 92%, 93%, 94%, 95%, 96%, 97%, 98%, or 99% identity to the amino acid sequence of SEQ ID NO: 106 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 106. In certain embodiments, a total of 1 to 5 amino acids have been substituted, inserted and/or deleted in SEQ ID NO: 106. In certain embodiments, substitutions, insertions, or deletions occur in regions outside the HVRs (i.e., in the FRs). Optionally, the anti-CD33 antibody comprises the VH sequence of SEQ ID NO: 106, including post-translational modifications of that sequence. In a particular embodiment, the VH comprises one, two or three HVRs selected from: (a) HVR-H1 comprising the amino acid sequence of SEQ ID NO:45, (b) HVR-H2 comprising the amino acid sequence of SEQ ID NO:51, and (c) HVR-H3 comprising the amino acid sequence of SEQ ID NO: 52.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 105. In certain embodiments, a VL sequence having at least 90%, 91%, 92%, 93%, 94%, 95%, 96%, 97%, 98%, or 99% identity to the amino acid sequence of SEQ ID NO: 105 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 105. In certain embodiments, a total of 1 to 5 amino acids have been substituted, inserted and/or deleted in SEQ ID NO: 105. In certain embodiments, the substitutions, insertions, or deletions occur in regions outside the HVRs (i.e., in the FRs). Optionally, the anti-CD33 antibody comprises the VL sequence of SEQ ID NO: 105, including post-translational modifications of that sequence. In a particular embodiment, the VL comprises one, two or three HVRs selected from (a) HVR-L1 comprising the amino acid sequence of SEQ ID NO:48; (b) HVR-L2 comprising the amino acid sequence of SEQ ID NO:49; and (c) HVR-L3 comprising the amino acid sequence of SEQ ID NO:50.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO: 106 and SEQ ID NO: 105, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO: 106 and a VL sequence of SEQ ID NO:105.

Provided herein are 33F3 antibodies comprising a light chain variable domain comprising the HVR1-LC, HVR2-LC and HVR3-LC sequence according to Kabat numbering as depicted in FIG. 3A and a heavy chain variable domain comprising the HVR1-HC, HVR2-HC and HVR3-HC sequence according to Kabat numbering as depicted in FIG. 3B. In some embodiments, the 33F3 antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 3A. In some embodiments, the 33F3 antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 3B.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

Antibody 33F9 and Other Embodiments

In some embodiments, the invention provides an anti-CD33 antibody comprising at least one, two, three, four, five, or six HVRs selected from (a) HVR-H1 comprising the amino acid sequence of SEQ ID NO:56; (b) HVR-H2 comprising the amino acid sequence of SEQ ID NO:57; (c) HVR-H3 comprising the amino acid sequence of SEQ ID NO:58; (d) HVR-L1 comprising the amino acid sequence of SEQ ID NO:53; (e) HVR-L2 comprising the amino acid sequence of SEQ ID NO:54; and (f) HVR-L3 comprising the amino acid sequence of SEQ ID NO:55.

In one aspect, the invention provides an antibody comprising at least one, at least two, or all three VH HVR sequences selected from (a) HVR-H1 comprising the amino acid sequence of SEQ ID NO:56; (b) HVR-H2 comprising the amino acid sequence of SEQ ID NO:57; and (c) HVR-H3 comprising the amino acid sequence of SEQ ID NO:58. In one embodiment, the antibody comprises HVR-H3 comprising the amino acid sequence of SEQ ID NO:58. In another embodiment, the antibody comprises HVR-H3 comprising the amino acid sequence of SEQ ID NO:58 and HVR-L3 comprising the amino acid sequence of SEQ ID NO:55. In a further embodiment, the antibody comprises HVR-H3 comprising the amino acid sequence of SEQ ID NO:58, HVR-L3 comprising the amino acid sequence of SEQ ID NO:55, and HVR-H2 comprising the amino acid sequence of SEQ ID NO:57. In a further embodiment, the antibody comprises (a) HVR-H1 comprising the amino acid sequence of SEQ ID NO:56; (b) HVR-H2 comprising the amino acid sequence of SEQ ID NO:57; and (c) HVR-H3 comprising the amino acid sequence of SEQ ID NO:58.

In another aspect, the invention provides an antibody comprising at least one, at least two, or all three VL HVR sequences selected from (a) HVR-L1 comprising the amino acid sequence of SEQ ID NO:53; (b) HVR-L2 comprising the amino acid sequence of SEQ ID NO:54; and (c) HVR-L3 comprising the amino acid sequence of SEQ ID NO:55. In one embodiment, the antibody comprises (a) HVR-L1 comprising the amino acid sequence of SEQ ID NO:53; (b) HVR-L2 comprising the amino acid sequence of SEQ ID NO:54; and (c) HVR-L3 comprising the amino acid sequence of SEQ ID NO:55.

In another aspect, an antibody of the invention comprises (a) a VH domain comprising at least one, at least two, or all three VH HVR sequences selected from (i) HVR-H1 comprising the amino acid sequence of SEQ ID NO: 56, (ii) HVR-H2 comprising the amino acid sequence of SEQ ID NO: 57, and (iii) HVR-H3 comprising an amino acid sequence selected from SEQ ID NO:58; and (b) a VL domain comprising at least one, at least two, or all three VL HVR sequences selected from (i) HVR-L1 comprising the amino acid sequence of SEQ ID NO:53, (ii) HVR-L2 comprising the amino acid sequence of SEQ ID NO:54, and (c) HVR-L3 comprising the amino acid sequence of SEQ ID NO:55.

In another aspect, the invention provides an antibody comprising (a) HVR-H1 comprising the amino acid sequence of SEQ ID NO:56; (b) HVR-H2 comprising the amino acid sequence of SEQ ID NO:57; (c) HVR-H3 comprising the amino acid sequence of SEQ ID NO:58; (d) HVR-L1 comprising the amino acid sequence of SEQ ID NO:53; (e) HVR-L2 comprising the amino acid sequence of SEQ ID NO:54; and (f) HVR-L3 comprising the amino acid sequence of SEQ ID NO:55.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 108. In certain embodiments, a VH sequence having at least 90%, 91%, 92%, 93%, 94%, 95%, 96%, 97%, 98%, or 99% identity to the amino acid sequence of SEQ ID NO: 108 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 108. In certain embodiments, a total of 1 to 5 amino acids have been substituted, inserted and/or deleted in SEQ ID NO: 108. In certain embodiments, substitutions, insertions, or deletions occur in regions outside the HVRs (i.e., in the FRs). Optionally, the anti-CD33 antibody comprises the VH sequence of SEQ ID NO: 108, including post-translational modifications of that sequence. In a particular embodiment, the VH comprises one, two or three HVRs selected from: (a) HVR-H1 comprising the amino acid sequence of SEQ ID NO:56, (b) HVR-H2 comprising the amino acid sequence of SEQ ID NO:57, and (c) HVR-H3 comprising the amino acid sequence of SEQ ID NO:58.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 107. In certain embodiments, a VL sequence having at least 90%, 91%, 92%, 93%, 94%, 95%, 96%, 97%, 98%, or 99% identity to the amino acid sequence of SEQ ID NO: 107 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 107. In certain embodiments, a total of 1 to 5 amino acids have been substituted, inserted and/or deleted in SEQ ID NO: 107. In certain embodiments, the substitutions, insertions, or deletions occur in regions outside the HVRs (i.e., in the FRs). Optionally, the anti-CD33 antibody comprises the VL sequence of SEQ ID NO: 107, including post-translational modifications of that sequence. In a particular embodiment, the VL comprises one, two or three HVRs selected from (a) HVR-L1 comprising the amino acid sequence of SEQ ID NO:53; (b) HVR-L2 comprising the amino acid sequence of SEQ ID NO:54; and (c) HVR-L3 comprising the amino acid sequence of SEQ ID NO:55.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO: 108 and SEQ ID NO: 107, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO: 108 and a VL sequence of SEQ ID NO:107.

Provided herein are 33F9 antibodies comprising a light chain variable domain comprising the HVR1-LC, HVR2-LC and HVR3-LC sequence according to Kabat numbering as depicted in FIG. 3A and a heavy chain variable domain comprising the HVR1-HC, HVR2-HC and HVR3-HC sequence according to Kabat numbering as depicted in FIG. 3B. In some embodiments, the 33F9 antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 3A. In some embodiments, the 33F9 antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 3B.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

Antibody 33H4 and Other Embodiments

In some embodiments, the invention provides an anti-CD33 antibody comprising at least one, two, three, four, five, or six HVRs selected from (a) HVR-H1 comprising the amino acid sequence of SEQ ID NO:62; (b) HVR-H2 comprising the amino acid sequence of SEQ ID NO:63; (c) HVR-H3 comprising the amino acid sequence of SEQ ID NO:64; (d) HVR-L1 comprising the amino acid sequence of SEQ ID NO:59; (e) HVR-L2 comprising the amino acid sequence of SEQ ID NO:60; and (f) HVR-L3 comprising the amino acid sequence of SEQ ID NO:61.

In one aspect, the invention provides an antibody comprising at least one, at least two, or all three VH HVR sequences selected from (a) HVR-H1 comprising the amino acid sequence of SEQ ID NO:62; (b) HVR-H2 comprising the amino acid sequence of SEQ ID NO:63; and (c) HVR-H3 comprising the amino acid sequence of SEQ ID NO:64. In one embodiment, the antibody comprises HVR-H3 comprising the amino acid sequence of SEQ ID NO:64. In another embodiment, the antibody comprises HVR-H3 comprising the amino acid sequence of SEQ ID NO:64 and HVR-L3 comprising the amino acid sequence of SEQ ID NO:61. In a further embodiment, the antibody comprises HVR-H3 comprising the amino acid sequence of SEQ ID NO:64, HVR-L3 comprising the amino acid sequence of SEQ ID NO:61, and HVR-H2 comprising the amino acid sequence of SEQ ID NO:63. In a further embodiment, the antibody comprises (a) HVR-H1 comprising the amino acid sequence of SEQ ID NO:62; (b) HVR-H2 comprising the amino acid sequence of SEQ ID NO:63; and (c) HVR-H3 comprising the amino acid sequence of SEQ ID NO:64.

In another aspect, the invention provides an antibody comprising at least one, at least two, or all three VL HVR sequences selected from (a) HVR-L1 comprising the amino acid sequence of SEQ ID NO:59; (b) HVR-L2 comprising the amino acid sequence of SEQ ID NO:60; and (c) HVR-L3 comprising the amino acid sequence of SEQ ID NO:61. In one embodiment, the antibody comprises (a) HVR-L1 comprising the amino acid sequence of SEQ ID NO:59; (b) HVR-L2 comprising the amino acid sequence of SEQ ID NO:60; and (c) HVR-L3 comprising the amino acid sequence of SEQ ID NO:61.

In another aspect, an antibody of the invention comprises (a) a VH domain comprising at least one, at least two, or all three VH HVR sequences selected from (i) HVR-H1 comprising the amino acid sequence of SEQ ID NO:62, (ii) HVR-H2 comprising the amino acid sequence of SEQ ID NO:63, and (iii) HVR-H3 comprising an amino acid sequence selected from SEQ ID NO:64; and (b) a VL domain comprising at least one, at least two, or all three VL HVR sequences selected from (i) HVR-L1 comprising the amino acid sequence of SEQ ID NO:59, (ii) HVR-L2 comprising the amino acid sequence of SEQ ID NO:60, and (c) HVR-L3 comprising the amino acid sequence of SEQ ID NO:61.

In another aspect, the invention provides an antibody comprising (a) HVR-H1 comprising the amino acid sequence of SEQ ID NO:62; (b) HVR-H2 comprising the amino acid sequence of SEQ ID NO:63; (c) HVR-H3 comprising the amino acid sequence of SEQ ID NO:64; (d) HVR-L1 comprising the amino acid sequence of SEQ ID NO:59; (e) HVR-L2 comprising the amino acid sequence of SEQ ID NO:60; and (f) HVR-L3 comprising the amino acid sequence of SEQ ID NO:61.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 110. In certain embodiments, a VH sequence having at least 90%, 91%, 92%, 93%, 94%, 95%, 96%, 97%, 98%, or 99% identity to the amino acid sequence of SEQ ID NO: 110 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 110. In certain embodiments, a total of 1 to 5 amino acids have been substituted, inserted and/or deleted in SEQ ID NO: 110. In certain embodiments, substitutions, insertions, or deletions occur in regions outside the HVRs (i.e., in the FRs). Optionally, the anti-CD33 antibody comprises the VH sequence of SEQ ID NO: 110, including post-translational modifications of that sequence. In a particular embodiment, the VH comprises one, two or three HVRs selected from: (a) HVR-H1 comprising the amino acid sequence of SEQ ID NO:62, (b) HVR-H2 comprising the amino acid sequence of SEQ ID NO:63, and (c) HVR-H3 comprising the amino acid sequence of SEQ ID NO:64.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 109. In certain embodiments, a VL sequence having at least 90%, 91%, 92%, 93%, 94%, 95%, 96%, 97%, 98%, or 99% identity to the amino acid sequence of SEQ ID NO: 109 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO: 109. In certain embodiments, a total of 1 to 5 amino acids have been substituted, inserted and/or deleted in SEQ ID NO: 109. In certain embodiments, the substitutions, insertions, or deletions occur in regions outside the HVRs (i.e., in the FRs). Optionally, the anti-CD33 antibody comprises the VL sequence of SEQ ID NO: 109, including post-translational modifications of that sequence. In a particular embodiment, the VL comprises one, two or three HVRs selected from (a) HVR-L1 comprising the amino acid sequence of SEQ ID NO:59; (b) HVR-L2 comprising the amino acid sequence of SEQ ID NO:60; and (c) HVR-L3 comprising the amino acid sequence of SEQ ID NO:61.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO: 110 and SEQ ID NO: 109, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO: 110 and a VL sequence of SEQ ID NO:109.

Provided herein are 33H4 antibodies comprising a light chain variable domain comprising the HVR1-LC, HVR2-LC and HVR3-LC sequence according to Kabat numbering as depicted in FIG. 3A and a heavy chain variable domain comprising the HVR1-HC, HVR2-HC and HVR3-HC sequence according to Kabat numbering as depicted in FIG. 3B. In some embodiments, the 33H4 antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 3A. In some embodiments, the 33H4 antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 3B.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

1. Antibody Affinity

In certain embodiments, an antibody provided herein has a dissociation constant (Kd) of ≤1 NM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$J]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 pd/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO M spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthin, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for CD33 and the other is for any other antigen. In certain embodiments, one of the binding specificities is for CD33 and the other is for CD3. See, e.g., U.S. Pat. No. 5,821,337. In certain embodiments, bispecific antibodies may bind to two different epitopes of CD33. Bispecific antibodies may also be used to localize cytotoxic agents to cells which express CD33. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to CD33 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-CD33 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CD33 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD33 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B.K.C. Lo, ed., Humana Press, Totowa, N.J.), pp. 255-268 (2003).

C. Assays

Anti-CD33 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to CD33. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized CD33 is incubated in a solution comprising a first labeled antibody that binds to CD33 (e.g., any of the antibodies described herein) and a second unlabeled antibody that is being tested for its ability to compete with the first antibody for binding to CD33. The second antibody may be present in a hybridoma supernatant. As a control, immobilized CD33 is incubated in a solution comprising the first labeled antibody but not the second unlabeled antibody. After incubation under conditions permissive for binding of the first antibody to CD33, excess unbound antibody is removed, and the amount of label associated with immobilized CD33 is measured. If the amount of label associated with immobilized CD33 is substantially reduced in the test sample relative to the control sample, then that indicates that the second antibody is competing with the first antibody for binding to CD33. See Harlow and Lane (1988) *Antibodies: A Laboratory Manual* ch. 14 (Cold Spring Harbor Laboratory, Cold Spring Harbor, N.Y.).

D. Immunoconjugates

The invention also provides immunoconjugates comprising an anti-CD33 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

$$Ab\text{-}(L\text{-}D)_p \qquad\qquad I$$

where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

$$-A_a-W_w-Y_y \qquad \text{II}$$

wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

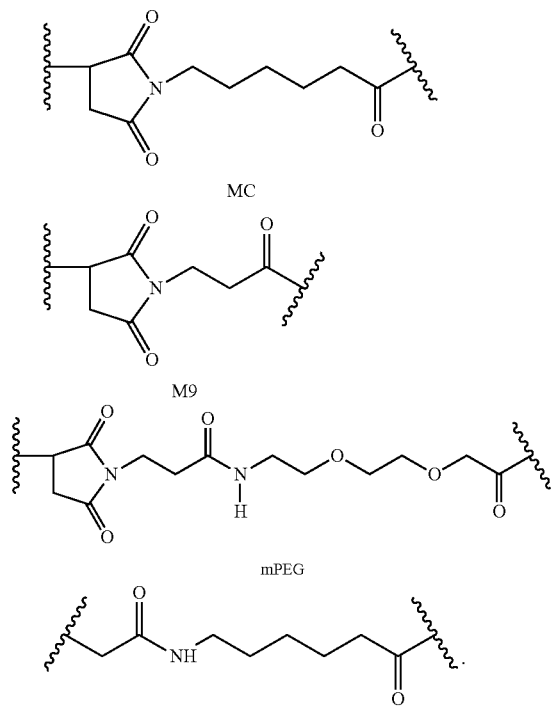

MC

M9 mPEG

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methylvaline-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the spacer unit is p-aminobenzyloxycarbonyl (PAB). In some embodiments, an ADC comprising a self-immolative linker has the structure:

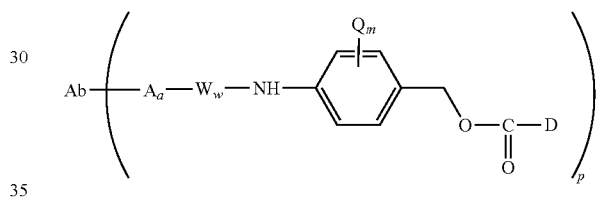

wherein Q is —$C_1$-$C_8$ alkyl, —O—($C_1$-$C_8$ alkyl), -halogen, -nitro, or -cyno; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

In some embodiments, linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

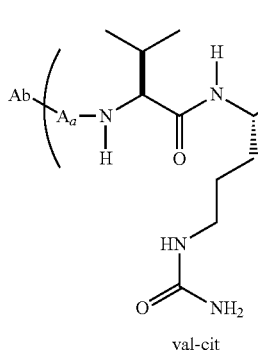
val-cit

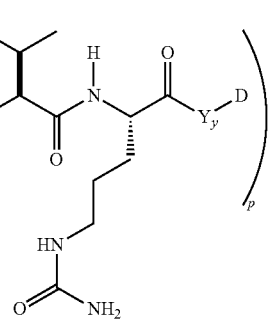
MC-val-cit

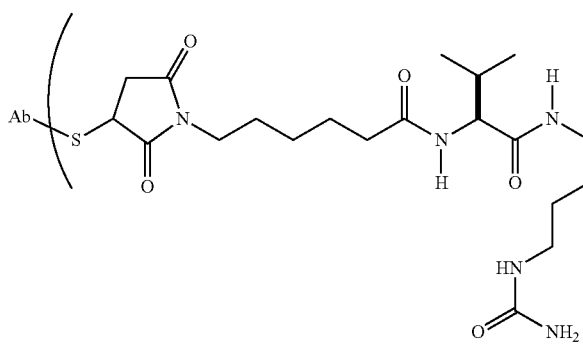
MC-val-cit-PAB

Further nonlimiting exemplary ADCs include the structures:

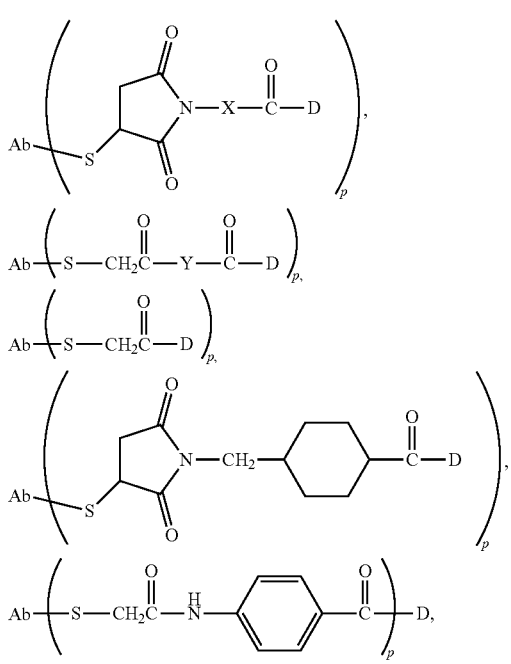

where X is:

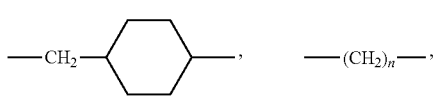

—(CH₂CH₂O)$_n$—,

—CH₂—⟨cyclohexyl⟩—C(O)—N(R)—(CH₂)$_n$—,

⟨phenyl⟩, ⟨phenyl⟩—(CH₂)$_n$—, or

—(CH₂)$_n$—C(O)—N(R)—(CH₂)$_n$—;

Y is:

—N(R)—⟨phenyl⟩— or —N(R)—(CH₂)$_n$—;

each R is independently H or $C_1$-$C_6$ alkyl; and n is 1 to 12.

Typically, peptide-type linkers can be prepared by forming a peptide bond between two or more amino acids and/or peptide fragments. Such peptide bonds can be prepared, for example, according to a liquid phase synthesis method (e.g., E. Schroder and K. Liibke (1965) "The Peptides", volume 1, pp 76-136, Academic Press).

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion) a substituents, such that more than one drug is coupled to the antibody in the ADC of Formula I.

The compounds of the invention expressly contemplate, but are not limited to, ADC prepared with the following linker reagents: bi s-maleimido-trioxyethy lene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

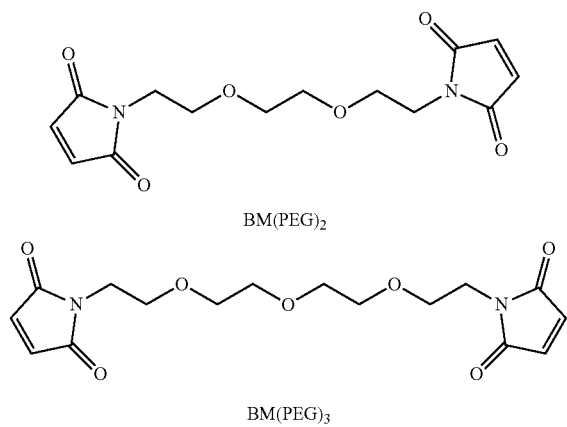

BM(PEG)$_2$

BM(PEG)$_3$

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995) *J. Org. Chem.* 60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties (1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) *PNAS* 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl) +/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424, 219) (prepared, for example, by the reaction of maytansinol with H$_2$S or P2S5); C-14-alkoxymethyl(demethoxy/ CH$_2$OR)(U.S. Pat. No. 4,331,598); C-14-hydroxymethyl or acyloxymethyl (CH$_2$OH or CH$_2$OAc) (U.S. Pat. No. 4,450, 254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315, 929) (for example, isolated from *Trewia nudlflora*); C-18-

N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

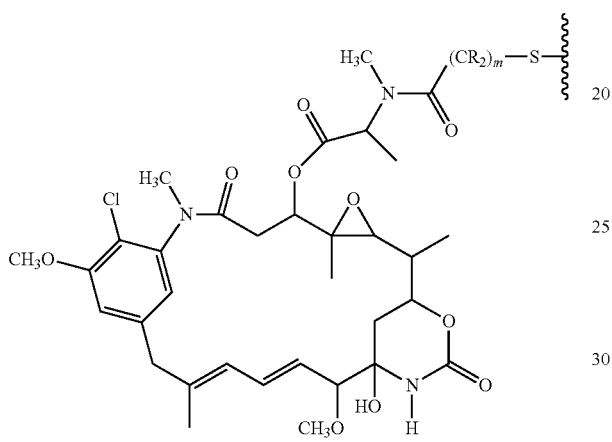

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; U.S. Pat. No. 633,410 (RE39151); U.S. Pat. No. 5,208,020; Widdison et al (2006) *J. Med. Chem.* 49:4392-4408, which are incorporated by reference in their entirety). In some embodiments, the maytansinoid drug moiety has the following stereochemistry:

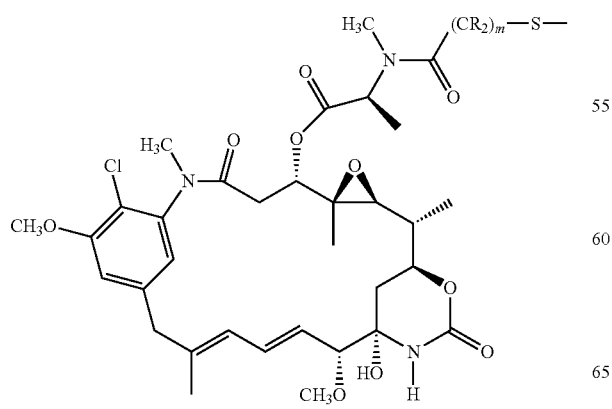

Exemplary embodiments of maytansinoid drug moieties include, but are not limited to, DM1; DM3; and DM4, having the structures:

DM1

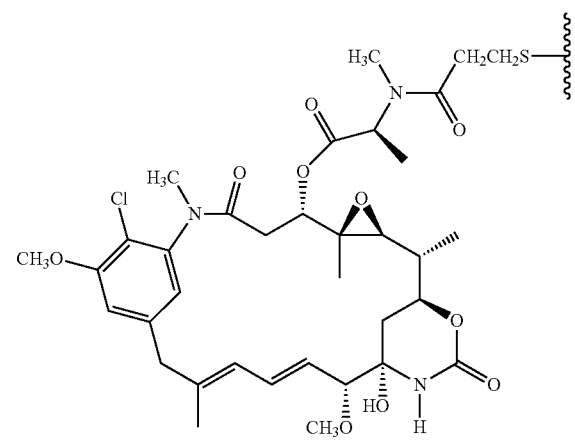

DM3

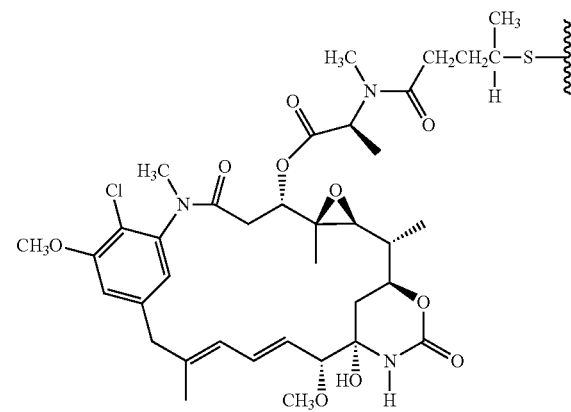

DM4

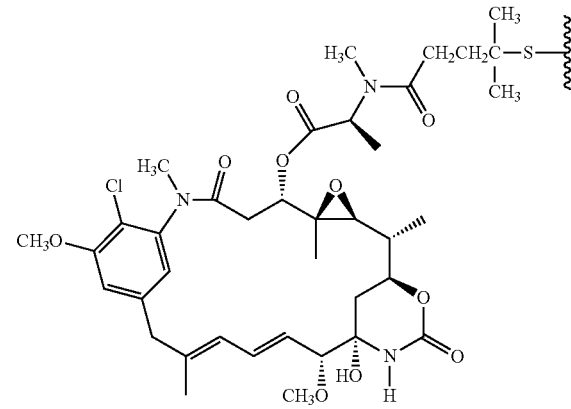

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

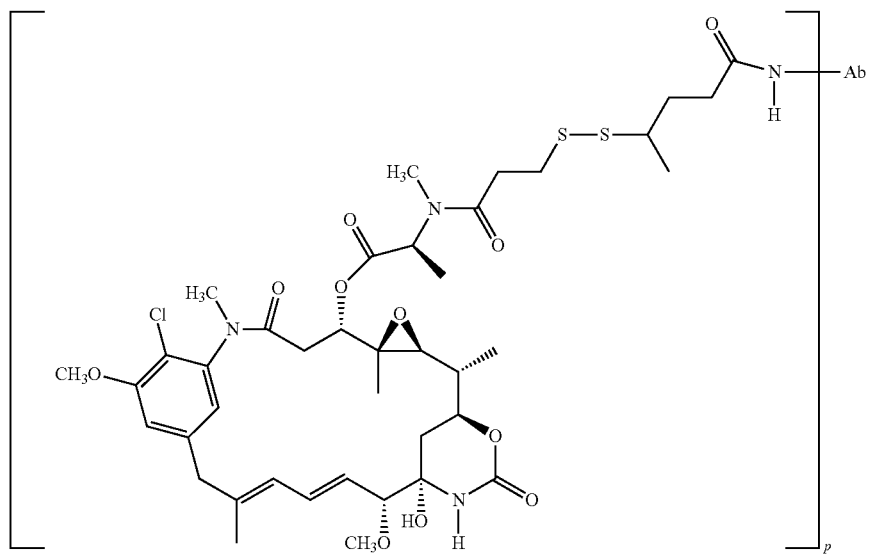
Ab-SPP-DM1
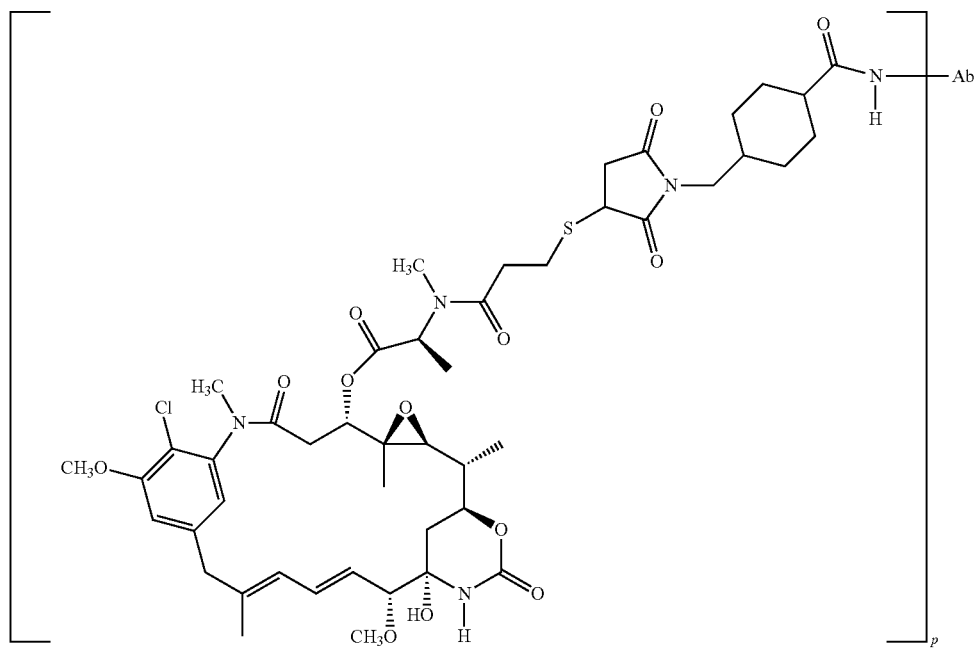
Ab-SMCC-DM1
Exemplary antibody-drug conjugates where DM1 is linked through a BMPEO linker to a thiol group of the antibody have the structure and abbreviation:

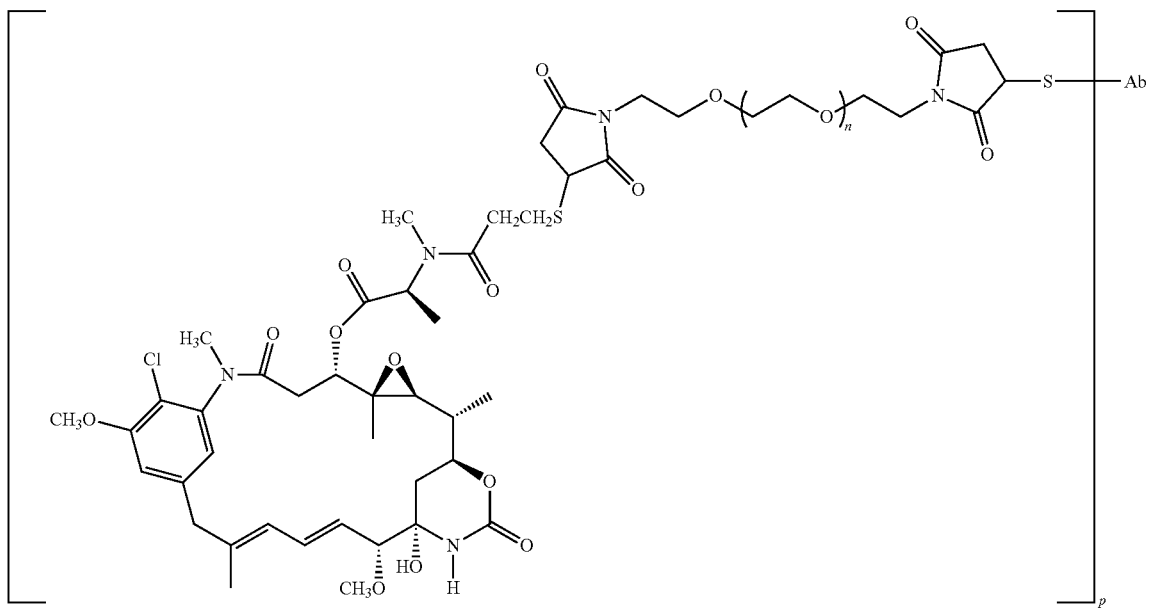

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4): 1458-1465).

Exemplary auristatin embodiments include the N-terminus linked monomethylauristatin drug moieties $D_E$ and $D_F$, disclosed in U.S. Pat. Nos. 7,498,298 and 7,659,241, the disclosures of which are expressly incorporated by reference in their entirety:

$D_E$

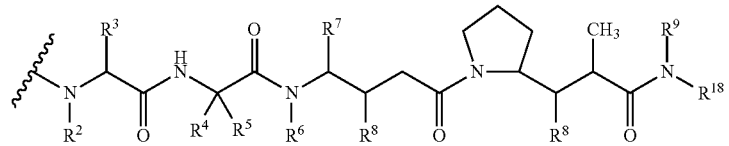

$D_F$

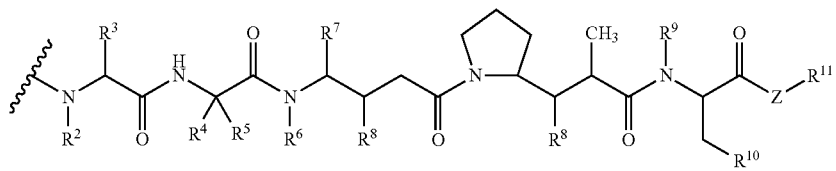

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, C3-C carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$; m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl.

In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

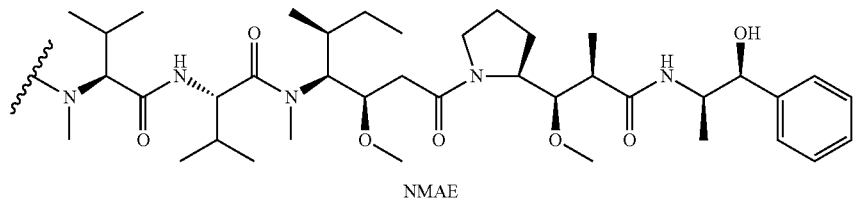 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

NMAE

An exemplary auristatin embodiment of formula $D_F$ is MMAF, wherein the wavy line indicates the covalent attachment to a linker (L) of an antibody-drug conjugate:

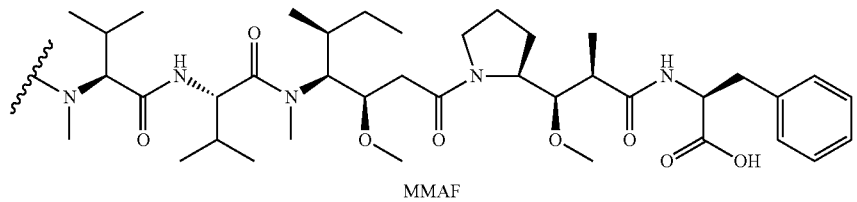

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

pared, for example, according to a liquid phase synthesis method (see, e.g., E. Schroder and K. Liibke, "The Peptides", volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis*, 1996, 719-725; Pettit et al (1996) *J. Chem. Soc. Perkin Trans.* 15:859-863; and Doronina (2003) Nat. *Biotechnol.* 21(7):778-784.

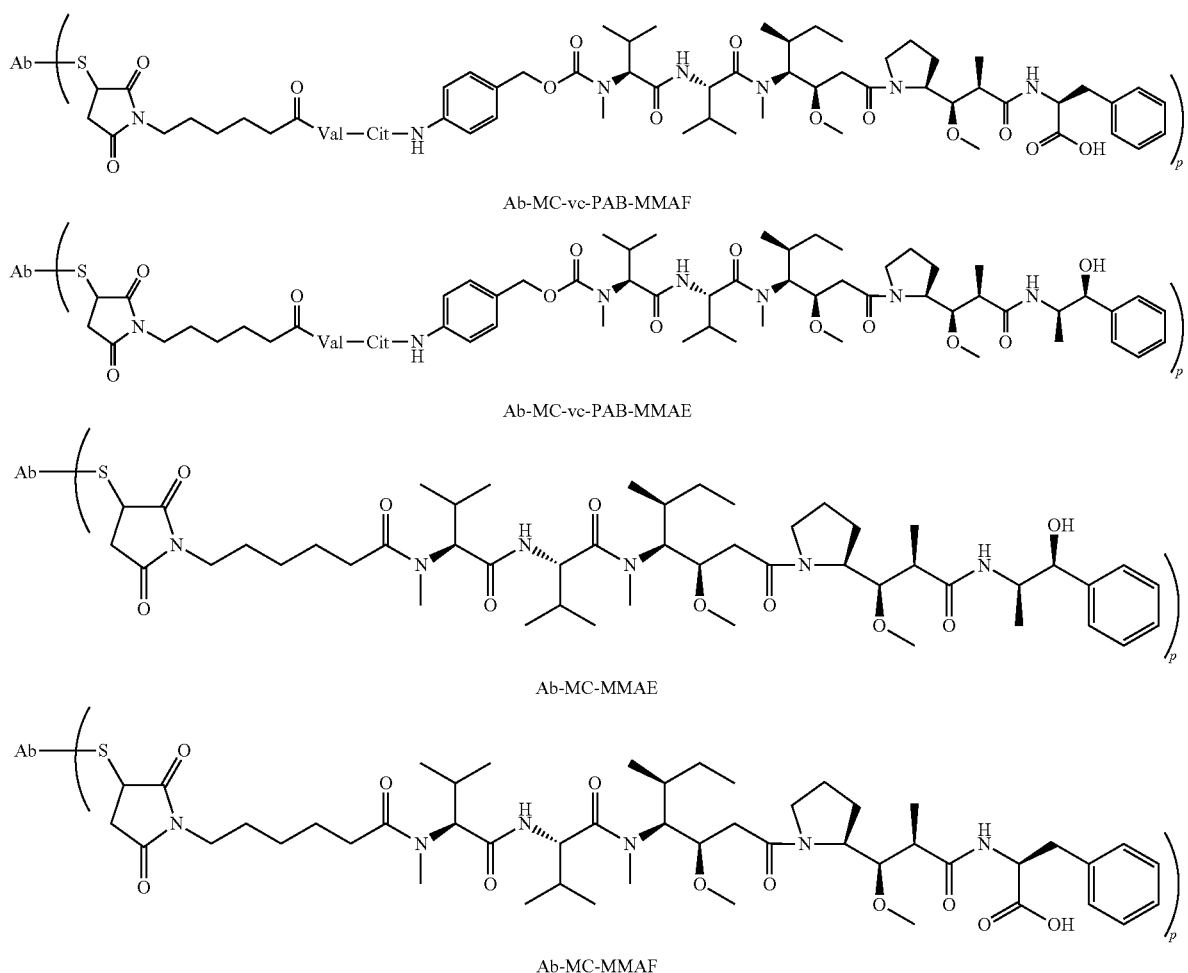

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) *Bioconjugate Chem.* 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be pre- In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J. Am. Chem. Soc.,* 87:5793-5795; Leimgruber, et al., (1965) *J. Am. Chem. Soc.,* 87:5791-5793). Since then, a number of PBDs, both naturally-occurring and analogues, have been reported (Thurston, et al., (1994) *Chem. Rev.* 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.,* 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

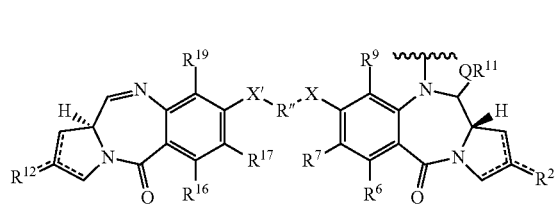

A and salts and solvates thereof, wherein:
the wavy line indicates the covalent attachment site to the linker;
the dotted lines indicate the optional presence of a double bond between C1 and C2 or C2 and C3;
$R^2$ is independently selected from H, OH, =O, =$CH_2$, CN, R, OR, =CH—$R^D$, =C($R^D$)$_2$, O—$SO_2$—R, $CO_2R$ and COR, and optionally further selected from halo or dihalo, wherein $R^D$ is independently selected from R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Q is independently selected from O, S and NH;
$R^{11}$ is either H, or R or, where Q is O, $SO_3M$, where M is a metal cation;

R and R' are each independently selected from optionally substituted $C_{1-8}$ alkyl, $C_{1-12}$ alkyl, $C_{3-8}$ heterocyclyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted $C_{1-12}$ alkyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.
In some embodiments, $R^6$ and $R^{16}$ are H.
In some embodiments, $R^7$ are $R^{17}$ are both $OR^{7A}$, where $R^{7A}$ is optionally substituted $C_{1-4}$ alkyl. In some embodiments, $R^{7A}$ is Me. In some embodiments, $R^{7A}$ is is $Ch_2Ph$, where Ph is a phenyl group.

In some embodiments, X is O.
In some embodiments, $R^{11}$ is H.
In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted $C_{5-20}$ aryl or $C_{5-7}$ aryl or $C_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =$CH_2$, =CH—$R^D$, and =C($R^D$)$_2$. In some embodiments, $R^2$ and $R^{12}$ are each =$CH_2$. In some embodiments, $R^2$ and $R^{12}$ are each H. In some embodiments, $R^2$ and $R^{12}$ are each =O.

In some embodiments, $R^2$ and $R^{12}$ are each =$CF_2$. In some embodiments, $R^2$ and/or $R^{12}$ are independently =C($R^D$)$_2$. In some embodiments, $R^2$ and/or $R^{12}$ are independently =CH—$R^D$.

In some embodiments, when $R^2$ and/or $R^{12}$ is =CH—$R^D$, each group may independently have either configuration shown below:

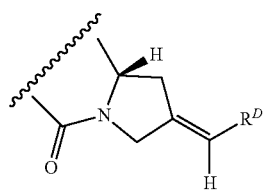

(I)

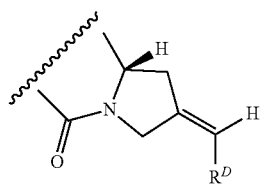
(II)

In some embodiments, a =CH—$R^D$ is in configuration (I).

In some embodiments, $R^{11}$ is a C3 alkylene group or a C5 alkylene group.

In some embodiments, an exemplary PBD dimer component of an ADC has the structure of Formula A(I):

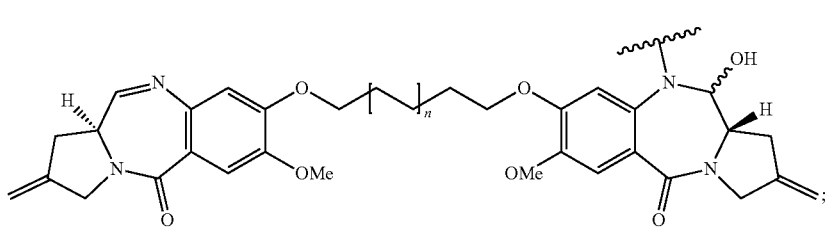
A(I)

wherein n is 0 or 1.

In some embodiments, an exemplary PBD dimer component of an ADC has the structure of Formula A(II):

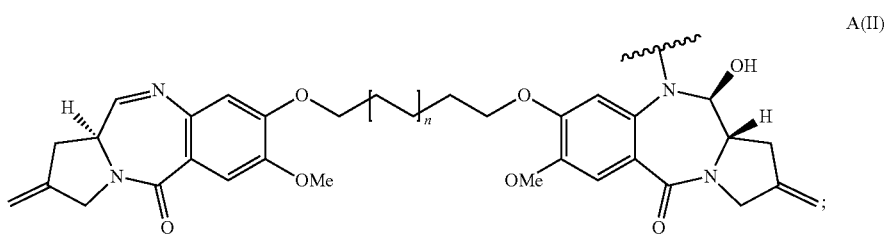
A(II)

wherein n is 0 or 1.

In some embodiments, an exemplary PBD dimer component of an ADC has the structure of Formula A(III):

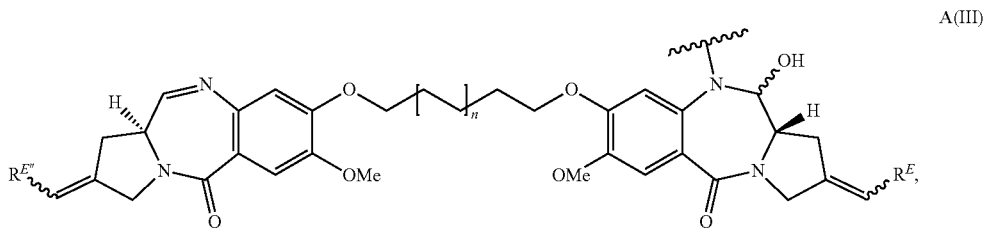
A(III)

wherein $R^E$ and $R^{E''}$ are each independently selected from H or $R^D$, wherein $R^D$ is defined as above; and wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

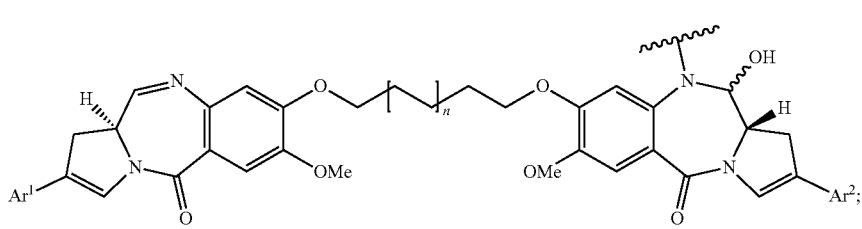

A(IV)

wherein Ar¹ and Ar² are each independently optionally substituted $C_{5-20}$ aryl; wherein Ar¹ and Ar² may be the same or different; and
wherein n is 0 or 1.

In some embodiments, an exemplary PBD dimer component of an ADC has the structure of Formula A(V):

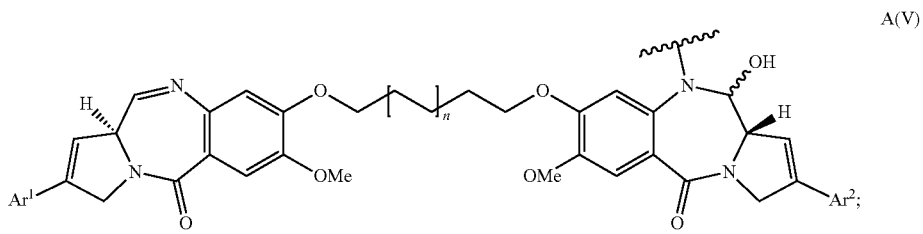

A(V)

wherein Ar¹ and Ar² are each independently optionally substituted $C_{5-20}$ aryl; wherein Ar¹ and Ar² may be the same or different; and
wherein n is 0 or 1.

In some embodiments, Ar¹ and Ar² are each independently selected from optionally substituted phenyl, furanyl, thiophenyl and pyridyl. In some embodiments, Ar¹ and Ar² are each independently optionally substituted phenyl. In some embodiments, Ar¹ and Ar² are each independently optionally substituted thien-2-yl or thien-3-yl. In some embodiments, Ar¹ and Ar² are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

and salts and solvates thereof, wherein:

the wavy line indicates the covalent attachment site to the linker;

the wavy line connected to the OH indicates the S or R configuration;

$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

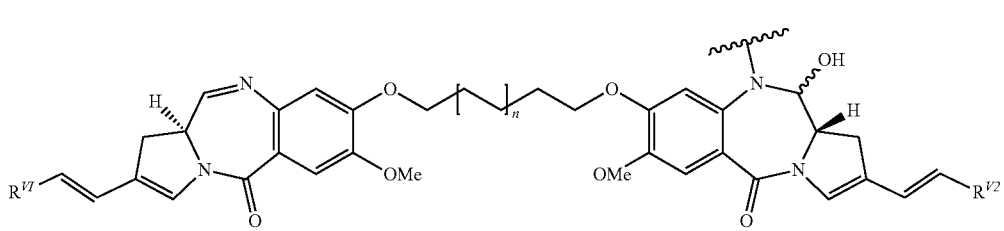

B

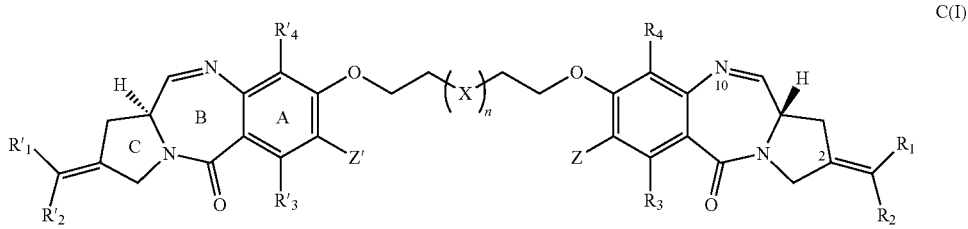

C(I)

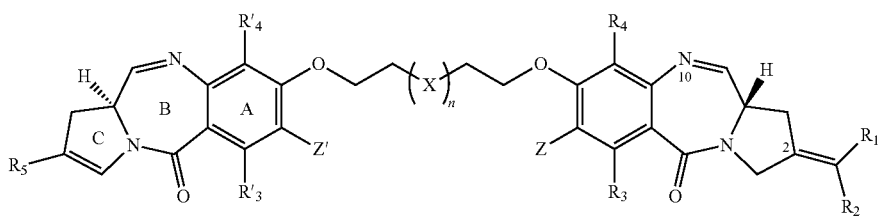

C(II)

Formulas C(I) and C(II) are shown in their N10-C11 imine form. Exemplary PBD drug moieties also include the carbinolamine and protected carbinolamine forms as well, as shown in the table below:

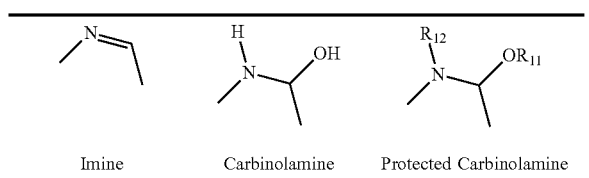

| Imine | Carbinolamine | Protected Carbinolamine | wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;

$R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is is H, $C_1$-$C_8$ alkyl, or a protecting group;

wherein a hydrogen of one of $R_1$, $R'_1$, $R_2$, $R'_2$, $R_5$, or $R_{12}$ or a hydrogen of the —$OCH_2CH_2(X)_nCH_2CH_2O$— spacer between the A rings is replaced with a bond connected to the linker of the ADC.

Exemplary PDB dimer portions of ADC include, but are not limited to (the wavy line indicates the site of covalent attachment to the linker):

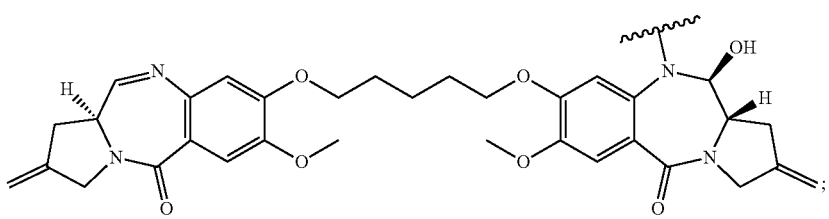

PBD dimer

Nonlimiting exemplary embodiments of ADCs comprising PBD dimers have the following structures:

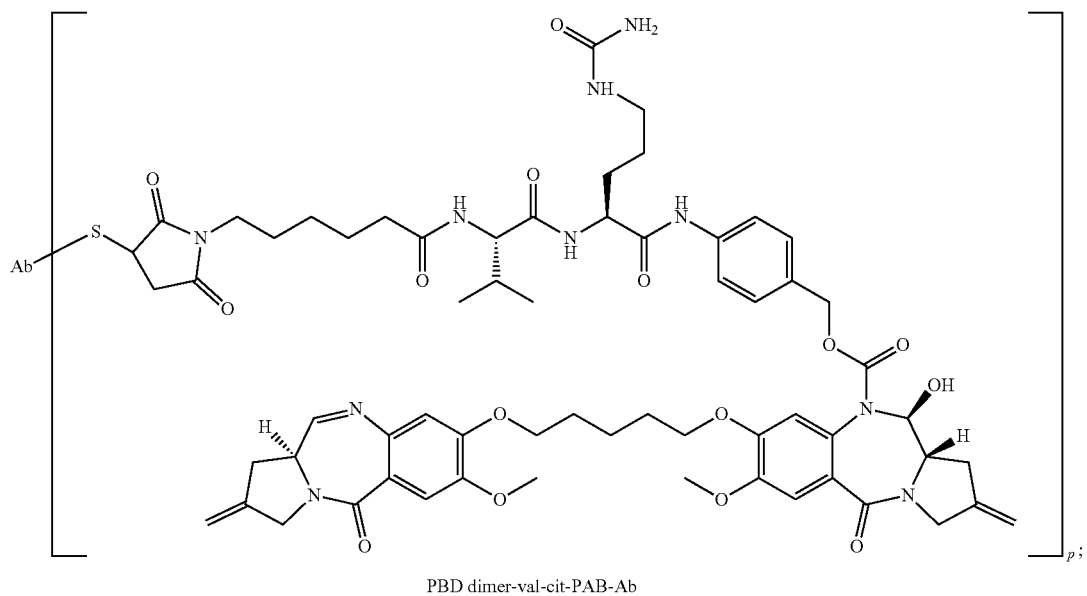

PBD dimer-val-cit-PAB-Ab

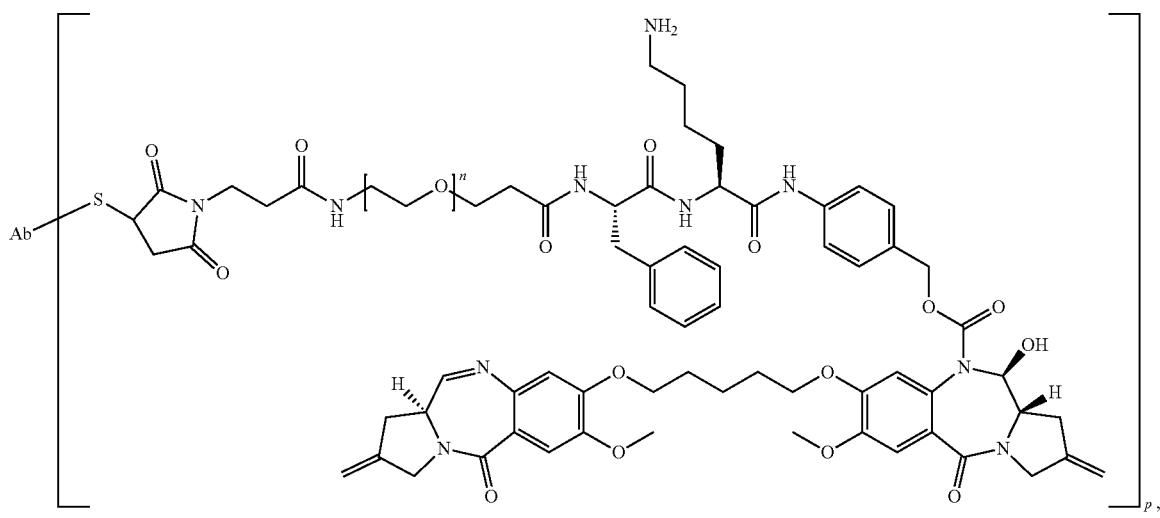

PBD dimer-Phe-Lys-PAB-Ab wherein:

n is 0 to 12. In some embodiments, n is 2 to 10. In some embodiments, n is 4 to 8. In some embodiments, n is selected from 4, 5, 6, 7, and 8.

A further non-limiting exemplary ADC comprising a PBD dimer may be made by conjugating a monomethyl pyridyl disulfide, N10-linked PBD (shown below) to an antibody:

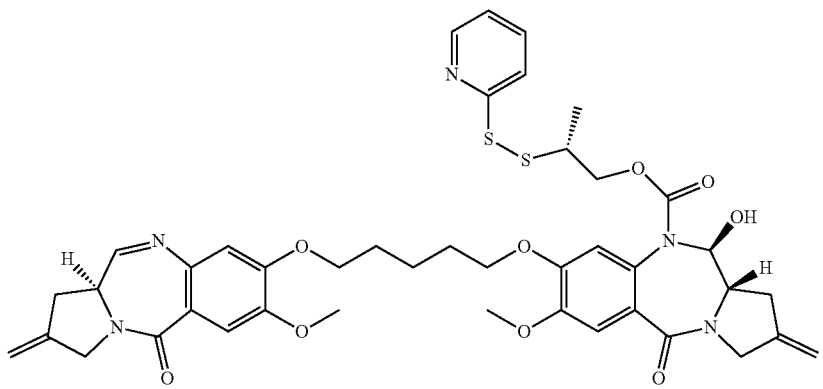

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598.

(5) Anthracyclines

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4): 1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703;), including phase II/III trials for hepatocellular carcinoma (Sun et al (2003) Proceedings of the American Society for Clinical Oncology 22, Abs1448; Quintieri (2003) *Proceedings of the American Association of Cancer Research*, 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

(Ia)

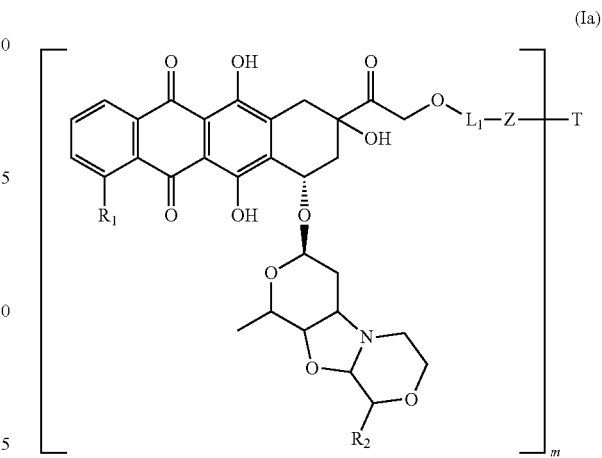

wherein $R_1$ is hydrogen atom, hydroxy or methoxy group and R2 is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

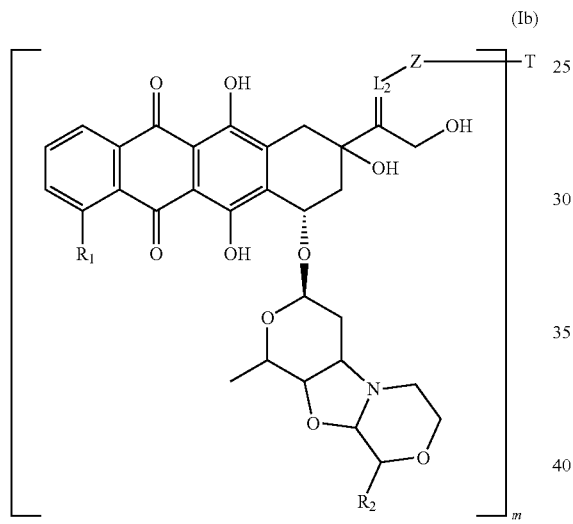

(Ib)

wherein $R_1$ is hydrogen atom, hydroxy or methoxy group and $R_2$ is a $C_1$-$C_5$ alkoxy group, or a pharmaceutically acceptable salt thereof;

L2 and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and R2 are both methoxy (—OMe).

In some embodiments, the nemorubicin component of a nemorubicin-containing ADC is PNU-159682. In some such embodiments, the drug portion of the ADC may have one of the following structures:

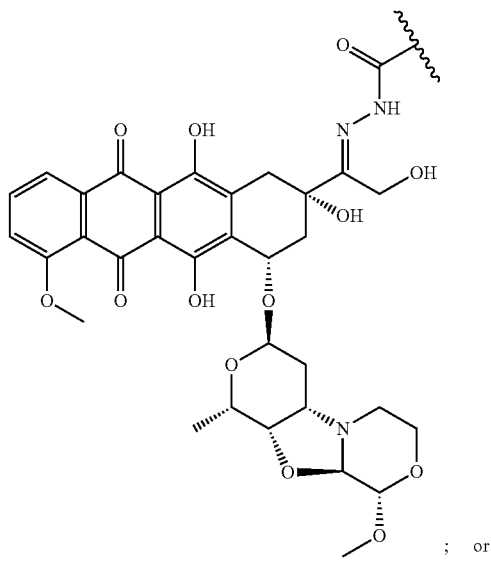

; or wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

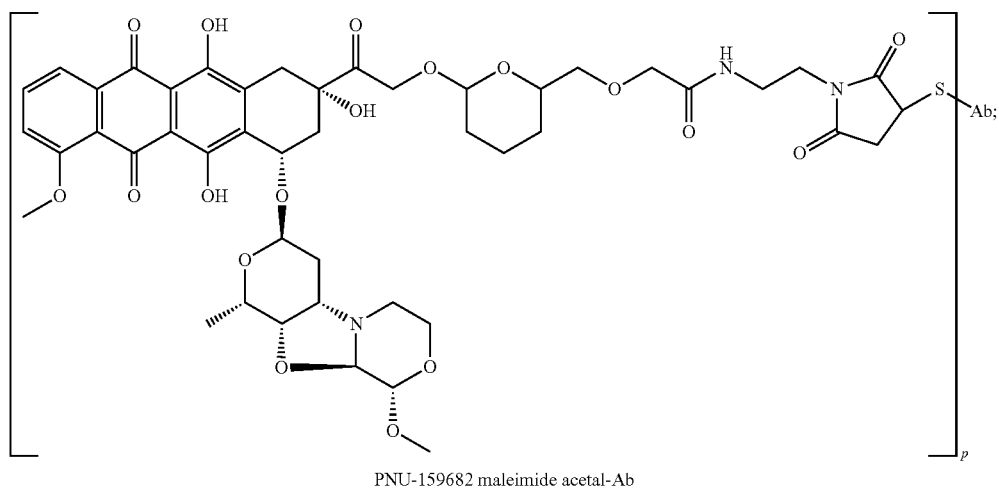
PNU-159682 maleimide acetal-Ab
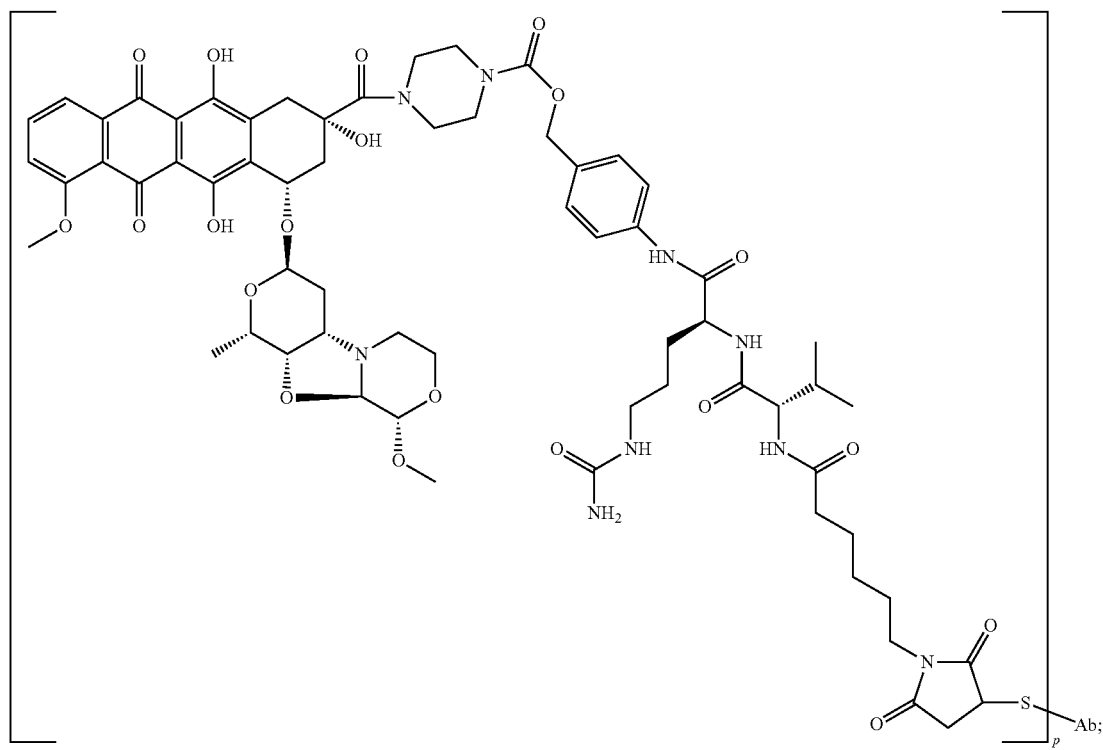
PNU-159682-val-cit-PAB-Ab
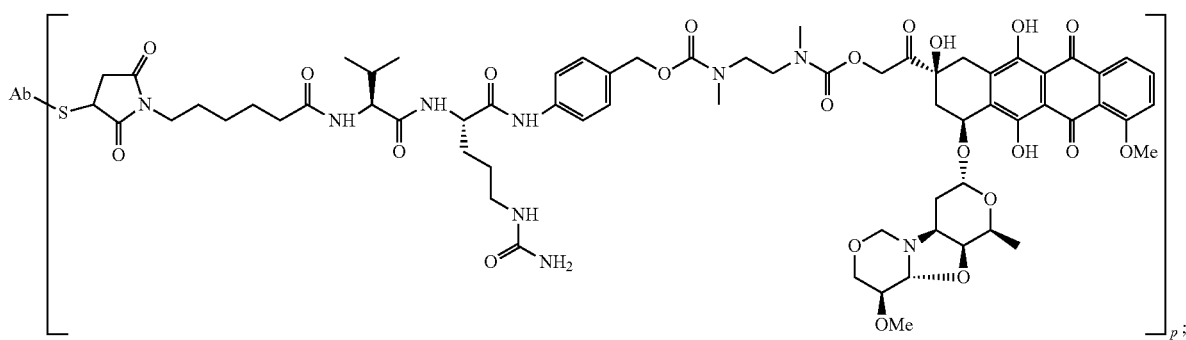
PNU-159682-val-cit-PAB-spacer-Ab

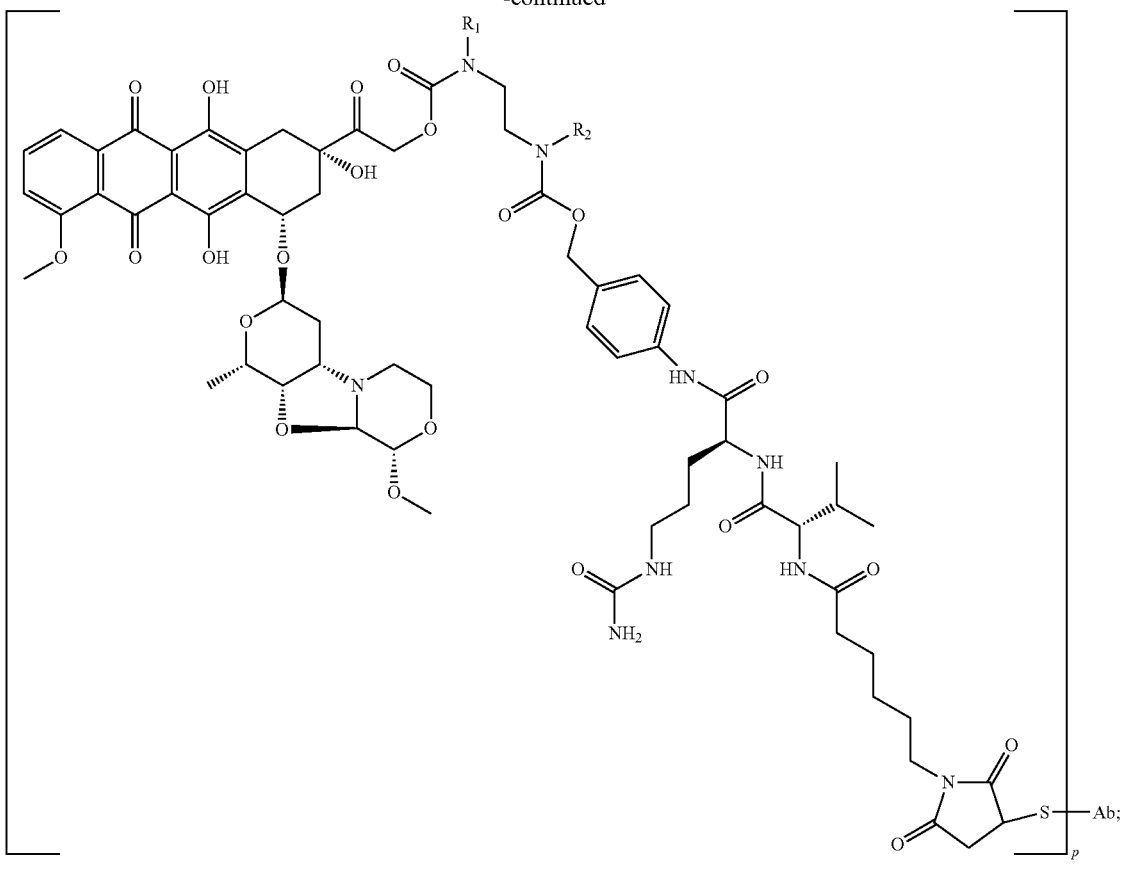

PNU-159682-val-cit-PAB-spacer($R^1R^2$)-Ab wherein:

$R_1$ and R2 are independently selected from H and $C_1$-$C_6$ alkyl; and

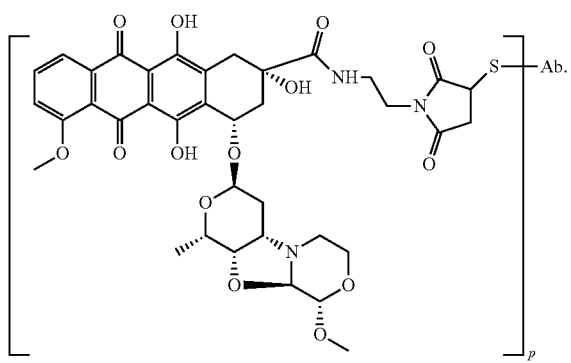

PNU-159682-maleimide-Ab

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

(6) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $^{125}I$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups on the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Methods and Compositions for Diagnostics and Detection

In certain embodiments, any of the anti-CD33 antibodies provided herein is useful for detecting the presence of CD33 in a biological sample. The term "detecting" as used herein encompasses quantitative or qualitative detection. A "biological sample" comprises, e.g., a cell or tissue (e.g., biopsy material, including cancerous or potentially cancerous lymphoid tissue, such as lymphocytes, lymphoblasts, monocytes, myelomonocytes, and mixtures thereof).

In one embodiment, an anti-CD33 antibody for use in a method of diagnosis or detection is provided. In a further aspect, a method of detecting the presence of CD33 in a biological sample is provided. In certain embodiments, the method comprises contacting the biological sample with an anti-CD33 antibody as described herein under conditions permissive for binding of the anti-CD33 antibody to CD33, and detecting whether a complex is formed between the anti-CD33 antibody and CD33 in the biological sample. Such method may be an in vitro or in vivo method. In one embodiment, an anti-CD33 antibody is used to select subjects eligible for therapy with an anti-CD33 antibody, e.g. where CD33 is a biomarker for selection of patients. In a further embodiment, the biological sample is a cell or tissue.

In a further embodiment, an anti-CD33 antibody is used in vivo to detect, e.g., by in vivo imaging, a CD33-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., The Oncologist 12:1379-1389 (2007) and Verel et al., J. Nucl. Med. 44:1271-1281 (2003). In such embodiments, a method is provided for detecting a CD33-positive cancer in a subject, the method comprising administering a labeled anti-CD33 antibody to a subject having or suspected of having a CD33-positive cancer, and detecting the labeled anti-CD33 antibody in the subject, wherein detection of the labeled anti-CD33 antibody indicates a CD33-positive cancer in the subject. In certain of such embodiments, the labeled anti-CD33 antibody comprises an anti-CD33 antibody conjugated to a positron emitter, such as $^{68}$Ga, $^{18}$F, $^{64}$Cu, 86Y, $^{76}$Br, $^{89}$Zr, and $^{124}$I. In a particular embodiment, the positron emitter is $^{89}$Zr.

In further embodiments, a method of diagnosis or detection comprises contacting a first anti-CD33 antibody immobilized to a substrate with a biological sample to be tested for the presence of CD33, exposing the substrate to a second anti-CD33 antibody, and detecting whether the second anti-CD33 is bound to a complex between the first anti-CD33 antibody and CD33 in the biological sample. A substrate may be any supportive medium, e.g., glass, metal, ceramic, polymeric beads, slides, chips, and other substrates. In certain embodiments, a biological sample comprises a cell or tissue. In certain embodiments, the first or second anti-CD33 antibody is any of the antibodies described herein.

Exemplary disorders that may be diagnosed or detected according to any of the above embodiments include CD33-positive cancers, such as CD33-positive AML, CD33-positive CML, CD33-positive MDS, CD33-positive chronic myelomonocytic leukemia, CD33-positive APL, CD33-positive chronic myeloproliferative disorder, CD33-positive thrombocytic leukemia, CD33-positive pre-B-ALL, CD33-positive preT-ALL, CD33-positive multiple myeloma, CD33-positive mast cell disease, CD33-positive mast cell leukemia, CD33-positive mast cell sarcoma, CD33-positive myeloid sarcomas, CD33-positive lymphoid leukemia, and CD33-positive undifferentiated leukemia. In some embodiments, a CD33-positive cancer is a cancer that receives an anti-CD33 immunohistochemistry (IHC) or in situ hybridization (ISH) score greater than "0," which corresponds to very weak or no staining in >90% of tumor cells, under the conditions described herein in Example B. In another embodiment, a CD33-positive cancer expresses CD33 at a 1+, 2+ or 3+ level, as defined under the conditions described herein in Example B. In some embodiments, a CD33-positive cancer is a cancer that expresses CD33 according to a reverse-transcriptase PCR (RT-PCR) assay that detects CD33 mRNA. In some embodiments, the RT-PCR is quantitative RT-PCR.

In certain embodiments, labeled anti-CD33 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, -galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}Ga$, $^{18}F$, $^{64}Cu$, $^{86}Y$, $^{76}Br$, $^{89}Zr$, and $^{124}I$. In a particular embodiment, a positron emitter is $^{89}Zr$.

F. Pharmaceutical Formulations

Pharmaceutical formulations of an anti-CD33 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-CD33 antibodies or immunoconjugates provided herein may be used in methods, e.g., therapeutic methods.

In one aspect, an anti-CD33 antibody or immunoconjugate provided herein is used in a method of inhibiting proliferation of a CD33-positive cell, the method comprising exposing the cell to the anti-CD33 antibody or immunoconjugate under conditions permissive for binding of the anti-CD33 antibody or immunoconjugate to CD33 on the surface of the cell, thereby inhibiting the proliferation of the cell. In certain embodiments, the method is an in vitro or an in vivo method. In further embodiments, the cell is a lymphocyte, lymphoblast, monocyte, or myelomonocyte cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *Anti Cancer Drugs* 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-CD33 antibody or immunoconjugate for use as a medicament is provided. In further aspects, an anti-CD33 antibody or immunoconjugate for use in a method of treatment is provided. In certain embodiments, an anti-CD33 antibody or immunoconjugate for use in treating CD33-positive cancer is provided. In certain embodiments, the invention provides an anti-CD33 antibody or immunoconjugate for use in a method of treating an individual having a CD33-positive cancer, the method comprising administering to the individual an effective amount of the anti-CD33 antibody or immunoconjugate. In one such embodiment, the method further comprises administering to the individual an effective amount of at least one additional therapeutic agent, e.g., as described below.

In a further aspect, the invention provides for the use of an anti-CD33 antibody or immunoconjugate in the manufacture or preparation of a medicament. In one embodiment, the medicament is for treatment of CD33-positive cancer. In a further embodiment, the medicament is for use in a method of treating CD33-positive cancer, the method comprising administering to an individual having CD33-positive cancer an effective amount of the medicament. In one such embodiment, the method further comprises administering to the individual an effective amount of at least one additional therapeutic agent, e.g., as described below.

In a further aspect, the invention provides a method for treating CD33-positive cancer. In one embodiment, the method comprises administering to an individual having such CD33-positive cancer an effective amount of an anti-CD33 antibody or immunoconjugate. In one such embodiment, the method further comprises administering to the individual an effective amount of at least one additional therapeutic agent, as described below.

A CD33-positive cancer according to any of the above embodiments may be, e.g., CD33-positive AML, CD33-positive CML, CD33-positive MDS, CD33-positive chronic myelomonocytic leukemia, CD33-positive APL, CD33-positive chronic myeloproliferative disorder, CD33-positive thrombocytic leukemia, CD33-positive pre-B-ALL, CD33-positive preT-ALL, CD33-positive multiple myeloma, CD33-positive mast cell disease, CD33-positive mast cell leukemia, CD33-positive mast cell sarcoma, CD33-positive myeloid sarcomas, CD33-positive lymphoid leukemia, and CD33-positive undifferentiated leukemia. In some embodiments, a CD33-positive cancer is a cancer that receives an anti-CD33 immunohistochemistry (IHC) or in situ hybridization (ISH) score greater than "0," which corresponds to very weak or no staining in >90% of tumor cells, under the conditions described herein in Example B. In another embodiment, a CD33-positive cancer expresses CD33 at a 1+, 2+ or 3+ level, as defined under the conditions described herein in Example B. In some embodiments, a CD33-positive cancer is a cancer that expresses CD33 according to a reverse-transcriptase PCR (RT-PCR) assay that detects CD33 mRNA. In some embodiments, the RT-PCR is quantitative RT-PCR.

An "individual" according to any of the above embodiments may be a human.

In a further aspect, the invention provides pharmaceutical formulations comprising any of the anti-CD33 antibodies or immunoconjugate provided herein, e.g., for use in any of the above therapeutic methods. In one embodiment, a pharmaceutical formulation comprises any of the anti-CD33 antibodies or immunoconjugates provided herein and a pharmaceutically acceptable carrier. In another embodiment, a pharmaceutical formulation comprises any of the anti-CD33 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 jag/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-CD33 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1

A. Monoclonal Antibody Generation

Monoclonal antibodies against human (hu) and cynomolgus (cyno) CD33 were generated using the following procedures by immunizing animals with recombinant hu and cyno CD33 extracellular domain (ECD, amino acids of 1-262 huCD33 and 1-257 cynoCD33) fused to a C-terminal Flag (RADYKDDDDK) (SEQ ID NO: 124) expressed in a mammalian expression system.

Positive clones were expanded and re-screened for binding to huCD33 and cynoCD33 by ELISA and FACS. Nine clones were identified: 33H4, 33F9, 27C6, 2E4, 7A1, 9C2, 9C3, 10D3 and 15G15 that reacted strongly by fluorescent activated cell sorting (FACs) with stable cell lines expressing recombinant human and cynomolgus monkey CD33, and with tumor-derived CD33 expressed on Acute Myeloid Leukemia tumor cell lines. Variants were made of 9C3 and 15G15 including 9C3.2, 9C3.3, 9C3.4, 15G15.33, 15G15.37, 15G15.83, 15G15.88, 15G15.7, 15G15.17, 15G15.30, 15G15.31, 15G15.39, and 15G15.84. In some instances, monovalent binding affinities were determined by Biacore (data not shown).

Sequences of isolated heavy and light chains are found in FIGS. 1-4 and sequence listing below. Residue numbers are according to Kabat et al., *Sequences of proteins of immunological interest,* 5th Ed., Public Health Service, National Institutes of Health, Bethesda, Md. (1991).

B. Species Cross-Reactivity

Monoclonal antibodies were tested to determine if they cross-react with cynoCD33 (which is 86.3% identical to huCD33 protein). HEK293AD cells stably expressing human or cynomolgus monkey CD33 were used to determine species-specificity by FACS. Cells were incubated with antibody clones at 1 jag/ml for 40 minutes at 4° C., washed and detected with either a goat-anti-mIgG (H+L) F(ab')$_2$-488 or goat-anti-hIgG (H+L) F(ab')$_2$-488 secondary antibody. FIG. 5A-D shows that 6 antibodies (7A1, 9C2, 10D3, 15G15, 27C6 and 33F9) recognized both recombinant hu and cynoCD33, while two antibodies (33H4 and 23E4) had similar binding profiles to MY9.6, binding only to human CD33. Further confirmation of cross-reactivity to cynomolgus monkey CD33 was done by FACS analyses of blood from cynomolgus (Mauritian origin). FIG. 7A-D shows 7A1, 9C2, 10D3, 15G15, 33F9 and 27C6 stain cynomolgus CD14+/CD33$^+$ myeloid cells, but 33H4, 23E4 or MY9.6 did not. Antibody binding was also confirmed for human CD14$^+$/CD33$^+$ myeloid cells. Tumor cells have the potential to alter the glycosylation pattern of proteins, for example, to escape from an immune response, so to insure that our antibodies would not be affected by this modification, FACS was done on AML tumor cell lines Molm13, HL-60, EOL-1, THP-1 and U937, and bone marrow from patients with confirmed cases of AML. FIG. 6A-D show a representative example of antibodies binding to Molm-13 or to a positive AML sample. These result suggests that antibody binding to CD33 is not affected by altered glycosylation found in AML tumor cell lines or patient samples.

C. Monoclonal Antibody Epitope Grouping

Epitope binning of anti-CD33 antibodies was performed using the Octet RED384 instrument (ForteBio). Biotinylated CD33 was captured onto Streptavidin biosensors at 10 jag/ml for 60 seconds. Binding of the first antibody to saturation was achieved by adding 50 jag/ml for 600 seconds. The same biosensors were dipped into the competing antibodies at 5 jag/ml and binding was measured for 300 seconds. The failure of the second antibody to bind in the presence of saturating quantities of the first antibody indicates the two antibodies were in the same epitope bin; the success of the second antibody to bind in the presence of the saturating quantities of the first antibody indicates the two antibodies were in different epitope bins. My9.6 was used as the first saturating antibody, followed by competing antibodies 27C6, 23E4, 33H4, 33F9, 9C2, 7A1, 10D3, and 15G15. Subsequent experiments used antibodies 33H4, 27C6, 23E4, 7A1, 33F9, and 15G15 as the saturating antibody to complete and confirm the analysis (data not shown).

Figure 8A:
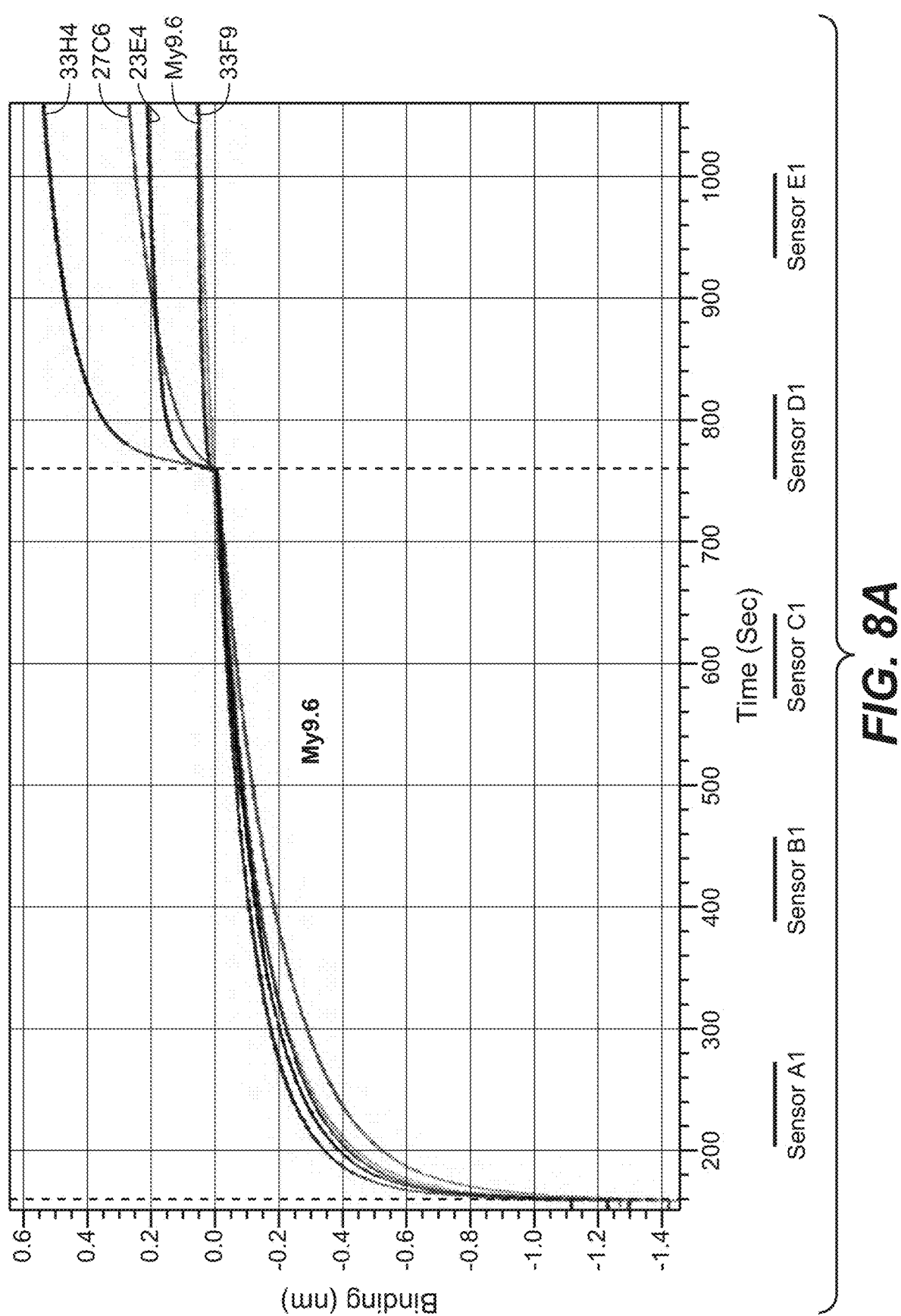
Figure 8B:
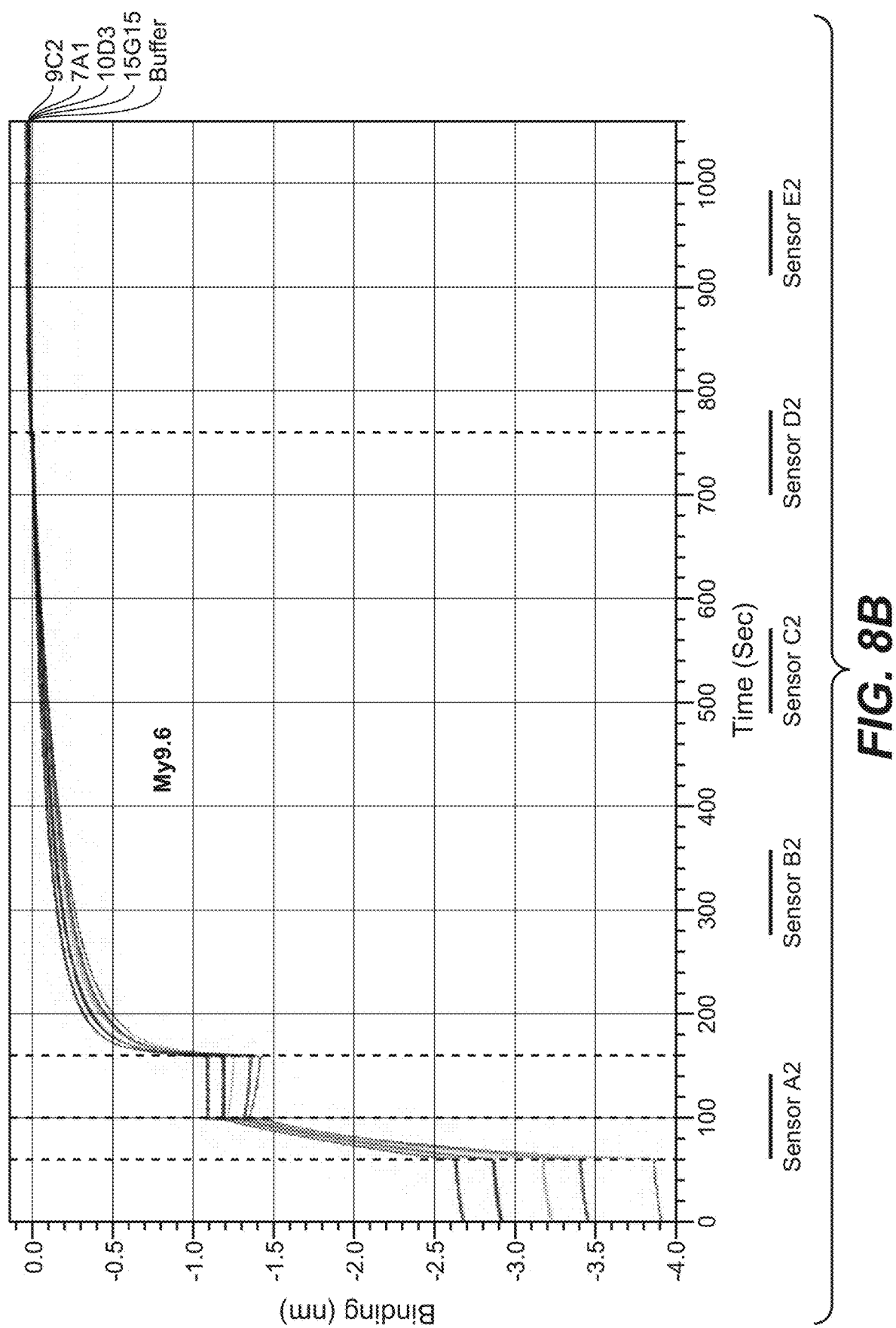

FIG. 8A-C shows epitope binning of the antibodies to CD33, and shows that 33F9, 7A1, 9C2, 10D3 and 15G15 bin with MY9.6, but 27C6, 23E4 and 33H4 do not. It was also determined that 27C6 has a different epitope from all other antibodies, and 23E4 and 33H4 share an overlapping epitope (data not shown). Epitope binning to cyno-CD33 shows that 7A1, 9C2, 10D3, and 15G15 bin together, but this bin does not include 27C6 and 33F9 (FIG. 8D). This suggests 27C6 and 33F9 bind to a different epitope on cyno-CD33. Data also revealed that 27C6 and 33F9 do not bin together (data not shown). Although the human binning showed overlap of MY9.6 with 7A1, 9C2, 10D3, 15G15 and 33F9, FACS data has shown that MY9.6, 23E4 and 33H4 do not bind cyno-CD33, therefore the epitope of MY9.6 to CD33 is probably not identical to 7A1, 9C2, 10D3, 15G15 and 33F9.

Epitope grouping was also determined using a cell-based competition binding FACS assay. HEK293AD cells expressing recombinant human CD33 were simultaneously incubated with a Dylight-650 labeled tracer antibody (0.3-1 jag/ml) and 50-100 fold excess of unlabeled competitor antibody. When the tracer is displaced by unlabeled antibody, competition has occurred indicating that the antibody binds to the same or similar region on CD33—this should occur when the same antibody is used as tracer and competitor. When there is no displacement of tracer by a different unlabeled antibody, the unlabeled antibody is binding to a different region in CD33.

Figure 9:
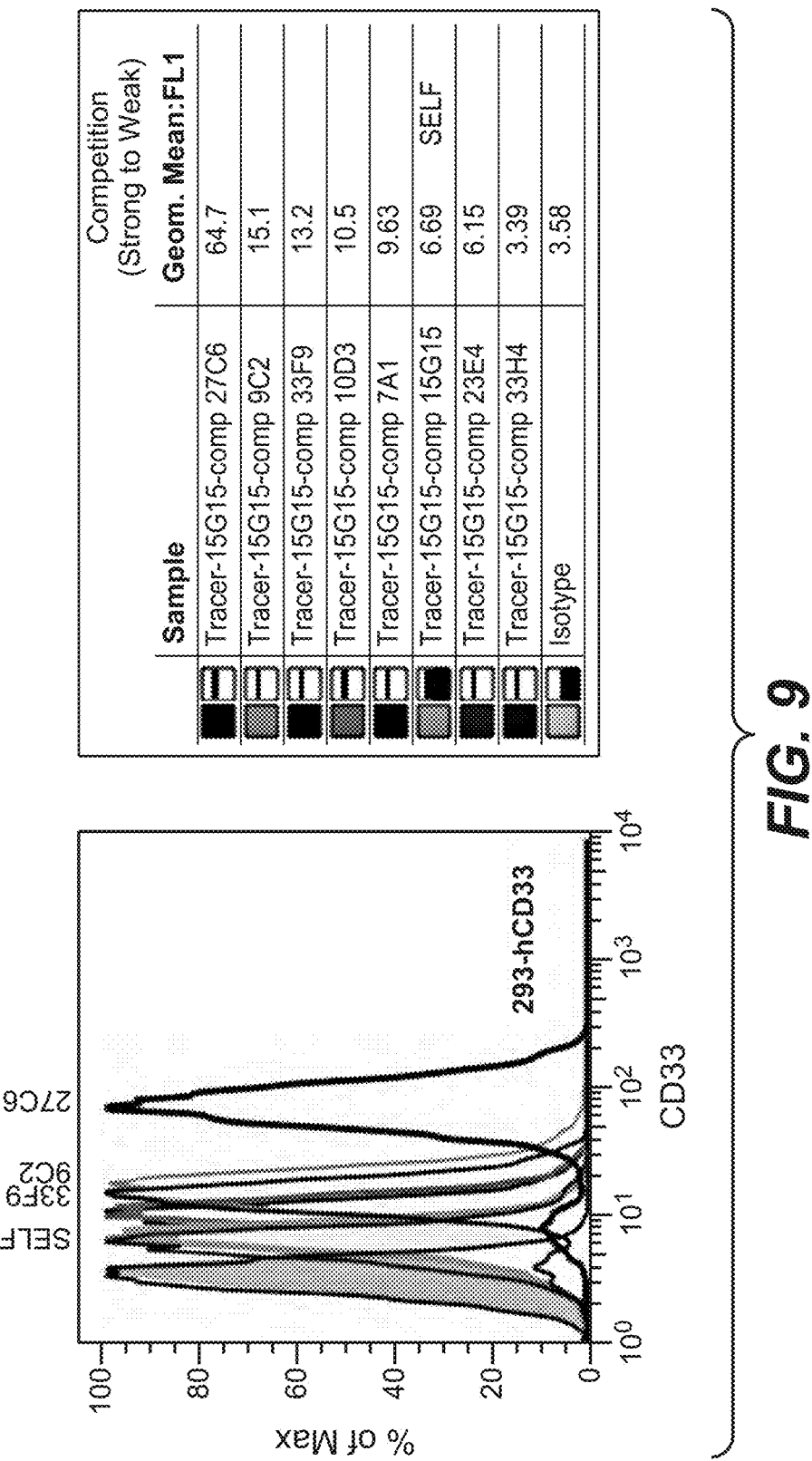
FIG. 9 shows an exemplary antibody competition experiment between anti-CD33 antibody 15G15 and anti-CD33 antibodies 27C6, 9C2, 33F9, 10D3, 7A1, 15G15, 23E4, and 33H4 for human CD33 binding.

FIG. 9 shows a representative example using 15G15 Dylight-650 tracer antibody with unlabeled competitor antibody at 50-fold excess of the tracer. As observed with Octet data, 27C6 did not compete with 15G15. Three other antibodies (9C2, 33F9, and 10D3) showed competition but not to the extent seen with unlabeled 15G15, suggesting that their epitopes may be similar, but not identical.

Figure 11:
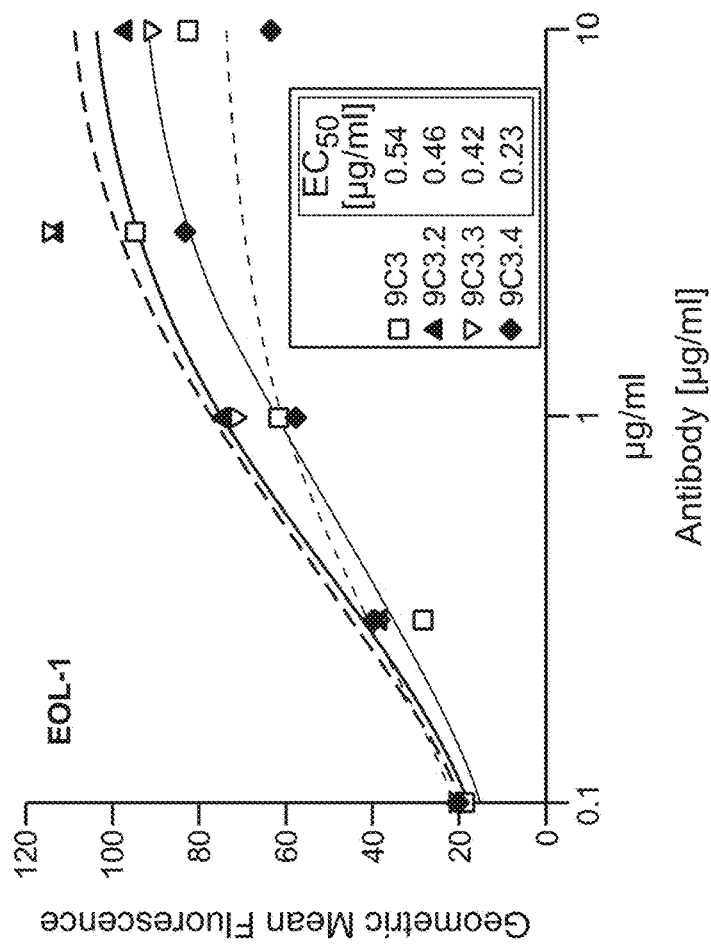
FIG. 11 shows that variants of 9C3 antibody, 9C3.2, 9C3.3, and 9C3.4, have improved binding to huCD33.
Figure 10C:
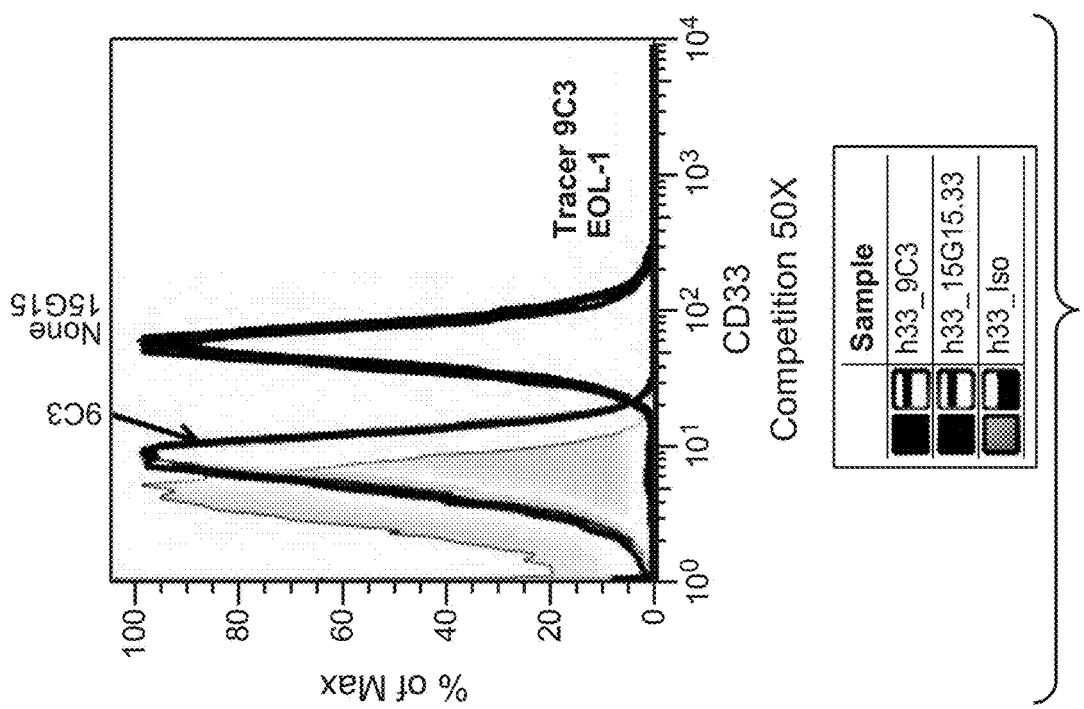

As shown in FIG. 10A-B, 9C3 was shown to bind to hu and cynoCD33. However the competitor antibody, 15G15, failed to displace the 9C3 labeled tracer antibody suggesting it binds to a different region on huCD33 (FIG. 10C). Physical characterization of 9C3 identified an atypical N-linked glycosylation site in the heavy chain between CDR2 and CDR3 at position 69 (kabat #). Site-directed mutagenesis was used to remove the site and FIG. 11 shows an improvement in binding to CD33 by FACS and Scatchard Analysis (Table 2).

To determine whether the CD33 antibodies bind to either the Ig-like V or Ig-like C domain of CD33, chimeric Ig-like domain membrane proteins were engineered that contain either a CD33 Ig-like V (M17-V136 including spacer H137-H143) linked to an irrelevant Ig-like C (including TM/CD; construct-88B) or an irrelevant Ig-like V linked to a CD33 Ig-like C (R144-Q228 including TM/CD L229) (construct-88) using standard molecular cloning methods. See FIG. 12A. N-terminal or cytoplasmic tags were attached to confirm that 293 cells transfected with these constructs express protein on the cell membrane (data not shown). Briefly, 293 cells were transiently transfected with constructs 88 & 88B using polyfect. After 48 hours, the cells were stained with 1-10 g/ml of Dylight-650 labeled 7A1, 9C2, 10D3 or 15G15 for 30-40 minutes at 4° C., washed and analyzed on a BD FACS calibur.

Figure 12D:
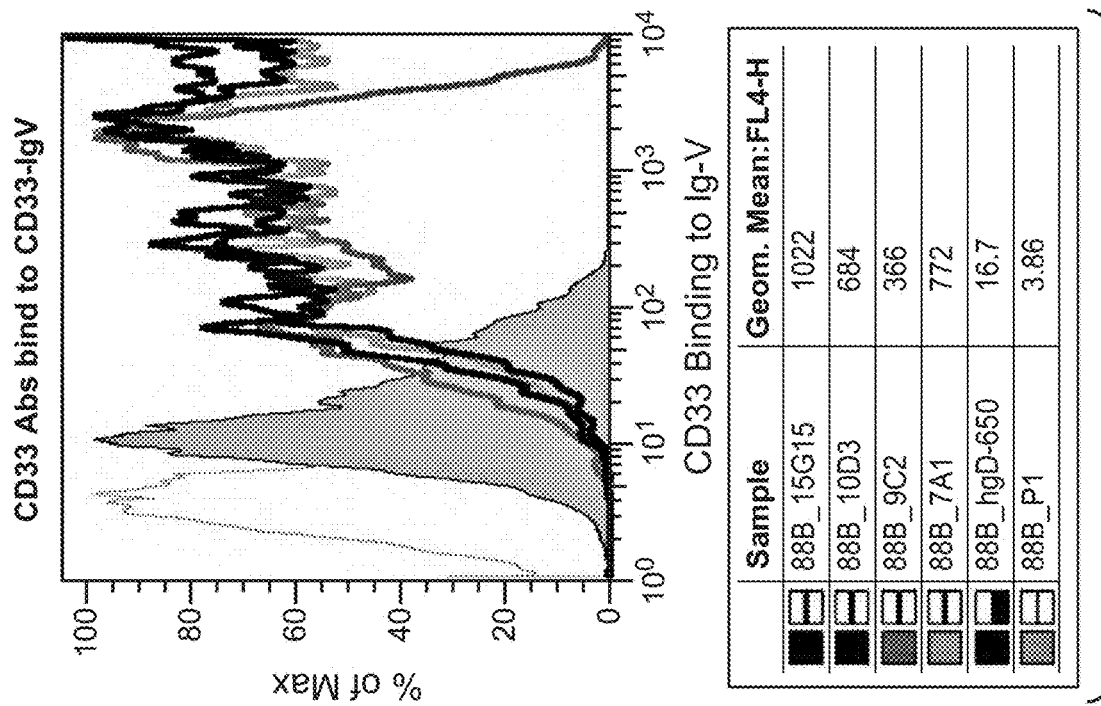
Figure 12C:
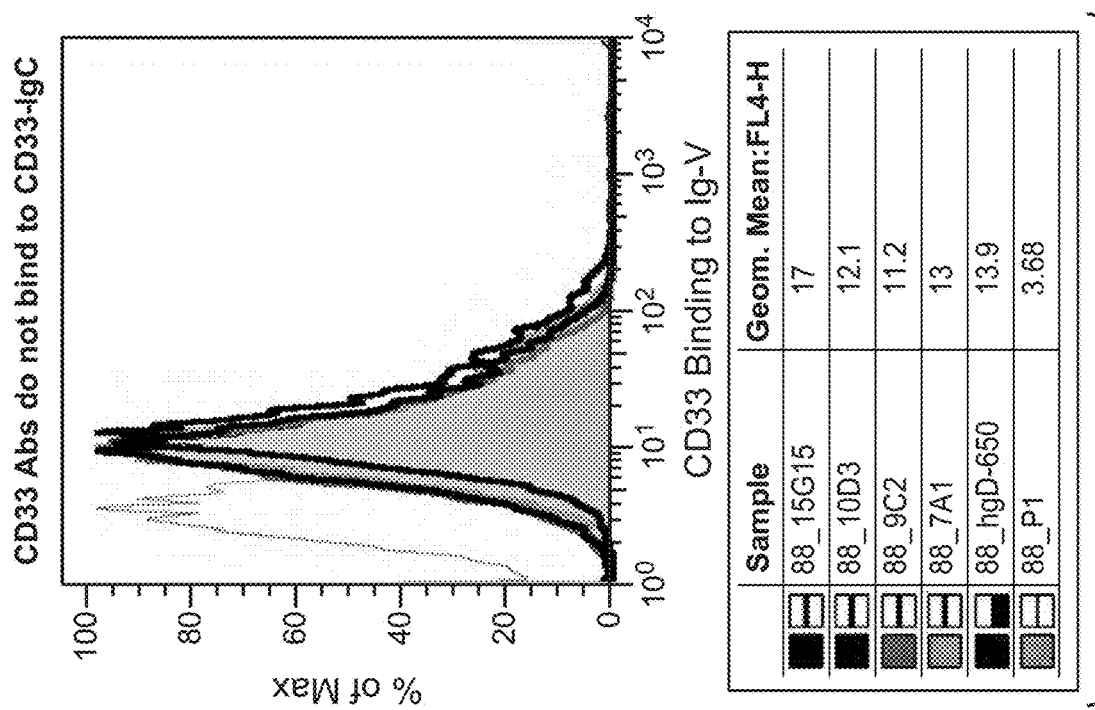

In FIG. 12D, antibodies 7A1, 9C2, 10D3 and 15G5 showed significant binding to the CD33 Ig-like V in construct 88B—at least 100 fold more compared to the isotype control. However, there was no binding to the CD33 Ig-like C in construct 88 (FIG. 12C)—in fact binding was equivalent to mock transfected cells (FIG. 12B). A positive signal was detected in construct 88 by an antibody to the irrelevant Ig-like V domain confirming that the construct was expressed on the cell surface (data not shown).

Figure 13B:
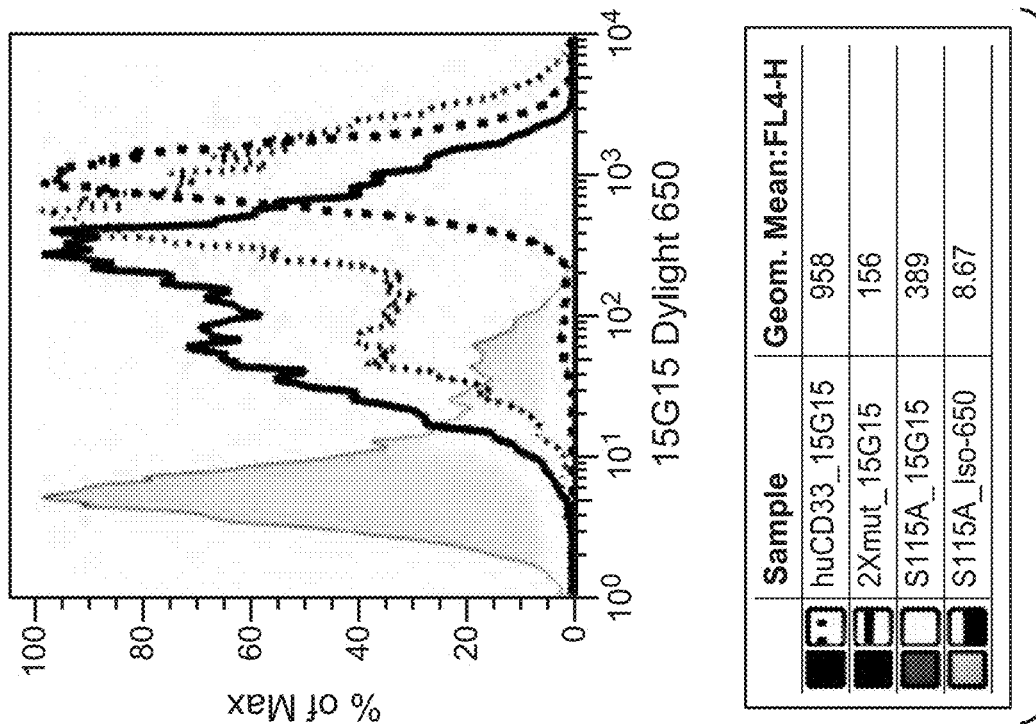
Figure 13A:
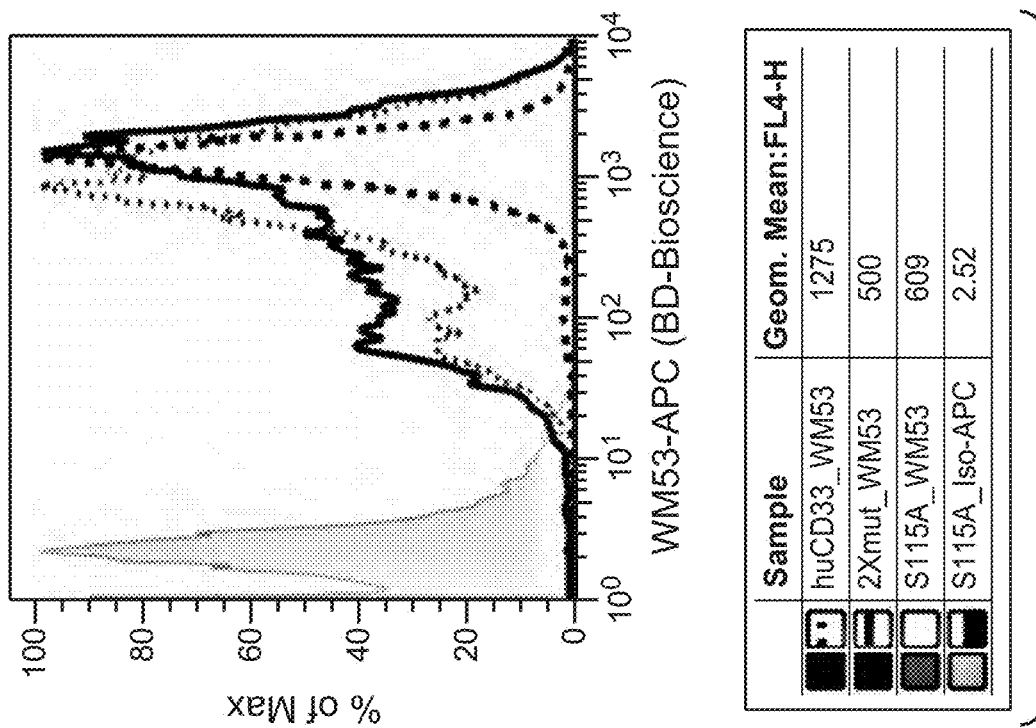

The Ig-like V domain of CD33 contains two N-linked glycosylation sites (NXS/T) and a SNP at position 69 of CD33 (R69G; r2455069) that may affect binding of an antibody to CD33. To test the effects of the two N-linked glycosylation sites, the serine residues at position S102 and S115 were substituted with alanine using standard site-specific mutagenesis (QuikChange II, Agilent Technologies) to reduce or abolish N-linked glycosylation at positions N100 and N113, respectively, in the Ig-like V domain of a full-length huCD33 membrane construct. Constructs contained either a single mutation (S115A) or a double mutation (S102A/S115A) and were expressed in 293AD cells by transient transfection using Polyfect (Promega) (FIG. 13A). FACS using 1 µg/ml of antibody conjugated to Dylight-650 was done 48 hours later. FIG. 13B shows the results of a representative example, clone 15G15, which exhibited significant binding to transiently transfected cells expressing either the partially or fully deglycosylated Ig-like V forms of huCD33—as shown by the 18-44 fold higher fluorescence compared to the isotype control. The experiment demonstrates that binding of the antibodies is independent of N-linked glycosylation in the Ig-like V domain. (HEK 293AD stably expressing high levels of rhCD33 was used as a positive control stain and is not suitable as reference for quantitation of expression by the transiently transfected cell.)

The influence of SNP (R69G) on antibody binding to the Ig-like V domain was investigated by the effect of glycine and arginine at amino acid position number 69 in huCD33 using standard site-specific mutagenesis and expressing the R69G variant in 293AD cells as described above (FIG. 14A).

Figure 14C:
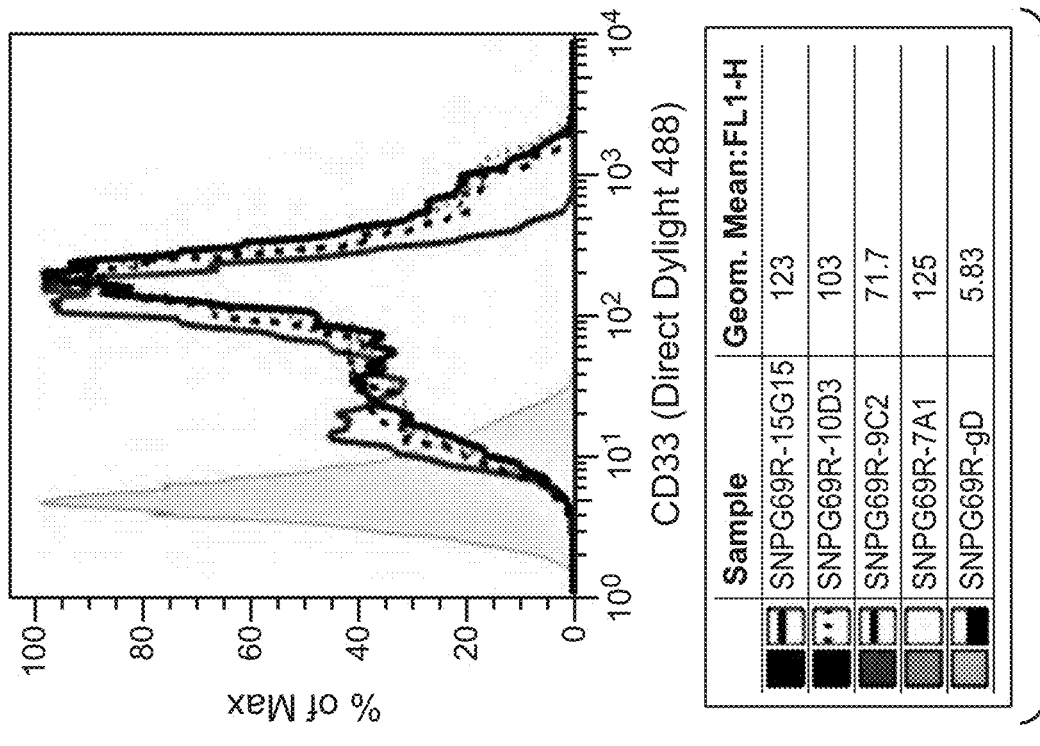
Figure 14B:
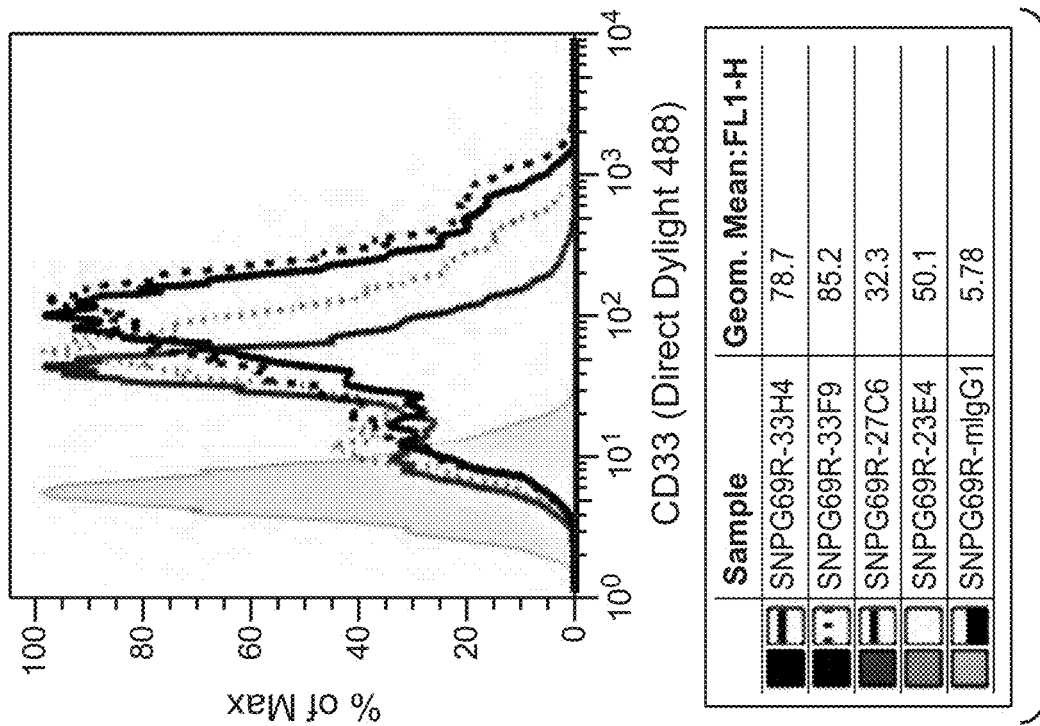

FIG. 14B-C shows that the antibodies tested bound to the R69 CD33 and G69 CD33, and that binding was similar between the two forms of huCD33 (data not shown).

D. Antibody Affinities

Scatchard analysis was performed following standard procedures (Holmes et al., *Science* 256:1205-1210 (1992)) to determine the relative binding affinities of the antibodies including 33H4, 33F9, 27C6, 2E4, 7A1, 9C2, 9C3, 9C3.2, 9C3.3, 9C3.4, 10D3, 15G15, 15G15.33, 15G15.83, and 15G15.88.

Anti-CD33 antibodies were [$I^{125}$] labeled using the indirect Iodogen method. The [$I^{125}$] labeled anti-CD33 antibodies were purified from free $^{125}$I-Na by gel filtration using a NAP-5 column (GE Healthcare); the purified iodinated anti-CD33 antibodies had a range of specific activities of 8-10 μCi/μg. Competition assay mixtures of 50 μL volume containing a fixed concentration of [$I^{125}$] labeled antibody and decreasing concentrations of serially diluted, unlabeled antibody were placed into 96-well plates. HEK293AD cells stably expressing recombinant hu or cynoCD33 or Molm-13 tumor cells expressing endogenous CD33 were cultured in growth media at 37° C. in 5% $CO_2$. Cells were detached from the flask using Sigma Cell Dissociation Solution and were washed with binding buffer, which consisted of Dulbecco's Modified Eagle Medium (DMEM) with 1% bovine serum albumin (BSA), 300 mM human IgG and 0.1% sodium azide. The washed cells were added to the 96 well plates at a density of 100,000 cells in 0.2 mL of binding buffer. The final concentration of the [$I^{125}$] labeled antibody in each well was -250 μM. The final concentration of the unlabeled antibody in the competition assay ranged from 1000 nM through ten 2-fold dilution steps to a 0 nM buffer-only assay. Competition assays were carried out in triplicate. Competition assays were incubated for 2 hours at room temperature. After the 2-hour incubation, the competition assays were transferred to a Millipore Multiscreen filter plate (Billerica, Mass.) and washed 4 times with binding buffer to separate the free from bound [$I^{125}$] labeled antibody. The filters were counted on a Wallac Wizard 1470 gamma counter (PerkinElmer Life and Analytical Sciences Inc.; Wellesley, Mass.). The binding data was evaluated using NewLigand software (Genentech), which uses the fitting algorithm of Munson and Robard to determine the binding affinity of the antibody (Munson and Robard 1980).

Table 2 shows the affinity (kD range of 0.2-23 nM) to recombinant hu and cynoCD33 expressed by HEK293AD CD33 stable cells and to Molm-13 cells.

TABLE 2

Antibody Affinity [kD = nM] to CD33 (Scatchard Analysis)

| AB ID | 293-huCD33 | 293-cynCD33 | Molm-13 |
|---|---|---|---|
| 2E3 | 2.5 | X | 3.0 |
| 33H4 | 2.4 | X | 0.6 |
| 27C6 | 13.4 | 4.5 | 23 |
| 33F9 | 8.7 | 0.92 | 92 |
| 7A1 | 3.0 | 0.54 | 6.3 |
| 9C2 | 6.5 | 0.7 | 10.3 |
| 9C3 | 0.8 | 0.6 | 5.8 |
| 9C3.2 | ND | ND | 2.0 |
| 9C3.3 | ND | ND | 2.2 |
| 9C3.4 | ND | ND | 2.7 |
| 10D3 | 3.3 | 0.7 | 2.6 |
| 15G15 | 1.3 | 0.3 | 4.8 |
| 15G15.33 | 0.7 | 0.3 | 0.9 |
| 15G15.83 | 0.5 | 0.2 | 0.5 |
| 15G15.88 | 0.7 | 0.2 | 0.8 |

E. Internalization of Anti-CD33 Antibody

One desirable attribute of an ADC target is the ability to internalize the antibody into a degradative compartment in the cell. To determine whether anti-CD33 antibody gets internalized upon binding, HL-60 or Molm-13 cells were pre-incubated for 2 hours at 37° C. with 0.3 mg/ml hIgG in RPMI medium to reduce non-specific binding to FcR before seeding in cell culture treated 4-well chamber slides (Nalge Nunc International). Antibody directly conjugated to Dylight 488 at a final concentration of 1 μg/mL was incubated with hIgG-blocked cells on ice for 30 minutes in the dark. The cells were immediately imaged to show membrane staining (T0) and followed with time-lapsed photography over a 10 hour period at 37° C. with a Leica SP5 confocal microscope. As shown in FIG. 15A, a representative example, 15G15, is rapidly internalized within 30 minutes by HL-60 cells. Localization of 15G15 to the lysosome was confirmed using an in vitro cell-based assay measuring the ability of an antibody drug conjugate to kill target cells. Briefly, Molm-13 or EOL-1 cells were pre-incubated with RPMI containing 0.3 mg/ml low endotoxin hIgG for 2 hours at 37° C. to reduce non-specific binding to FcR, and plated at a density of 8,000-16,000 cells/well in a 96-plate. The test articles, isotype-L-D #1 or 15G15.33 L-D #1, were added to the cells with a final concentration range of 0-1000 ng/ml in 3-fold steps and incubated for ~60 hours at 37° C. with 5% $CO_2$. Cell viability was determined using CellTiter-Glo (Promega, Inc) and an Envision 2012 Multilabel Reader (Perkin Elmer). FIG. 15B shows specific killing and complete ablation of target cells with 15G15.33-L-D #1 ADC compared to the isotype ADC ($EC_{50}$ of 6 and 63 ng/ml respectively), thus confirming ADC trafficking and processing in the lysosome. Both ADC's had a similar drug load.

F. Production of Anti-CD33 Antibody Drug Conjugates

For larger scale antibody production, antibodies were produced in CHO cells. Vectors coding for VL and VH were transfected into CHO cells and IgG was purified from cell culture media by protein A affinity chromatography.

Anti-CD33 antibody-drug conjugates (ADCs) were produced by conjugating 15G15 with a heavy chain A118C mutation (15G15 thio-HC A118C) and 15G15.33 with a heavy chain A118C mutation (15G15.33 thio-HC A118C) or a light chain V205C mutation (15G15.33 thio-LC V205C) to the drug-linker moiety monomethyl-pyridyl disulfide, N10-linked pyrrolobenzodiazepine (see FIG. 16; L-D #1) or maleimide with acetal linker-PNU (see FIG. 17; L-D #2). As initially isolated, the engineered cysteine residues in antibodies 15G15 and 15G15.33 exist as mixed disulfides with cellular thiols (e.g., glutathione) and are thus unavailable for conjugation. Partial reduction of these antibodies (e.g., with DTT), purification, and reoxidation with dehydroascorbic acid (DHAA) gives antibodies with free cysteine sulfhydryl groups available for conjugation, as previously described, e.g., in Junutula et al. (2008) Nat. *Biotechnol.* 26:925-932 and US 2011/0301334. Briefly, the antibodies were combined with the drug-linker moiety to allow conjugation of the drug-linker moiety to the free cysteine residues of the antibody. After several hours, the ADCs were purified. The drug load (average number of drug moieties per antibody) for each ADC was determined and was between 1.4-1.6 for the PBD conjugates and 1.3 for the PNU conjugates.

G. Efficacy of Anti-CD33 Antibody Drug Conjugates in HL-60 and EOL-1 Human Acute Myeloid Leukemia Cell Line Xenograft Models The efficacy of the anti-CD33 ADCs was investigated using human Acute Myeloid Leukemia xenograft models, HL-60 (AML subtype M2) and EOL-1 (AML subtype M4a). Both are associated with intermediate to poor prognosis as a result of their genetics and molecular aberrations. Female C.B-17 SCID mice (Charles River Laboratories; Hollister, Calif.) were each inoculated subcutaneously in the flank area with five million cells of HL-60 or EOL-1. When the xenograft tumors reached an average tumor volume of 100-300 mm³ (referred to as Day 0), animals were randomized into groups of 7-10 mice each and received a single intravenous injection of the ADCs. Approximately 4 hours prior to administration of ADCs, animals were dosed intraperitoneally with excess amount (30 mg/kg) of anti-gD control antibody to block possible nonspecific antibody binding sites on the tumor cells. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration. The presence of the antibodies was confirmed by PK bleeds at 1, 7 and 14 days post injection.

Figure 16A:
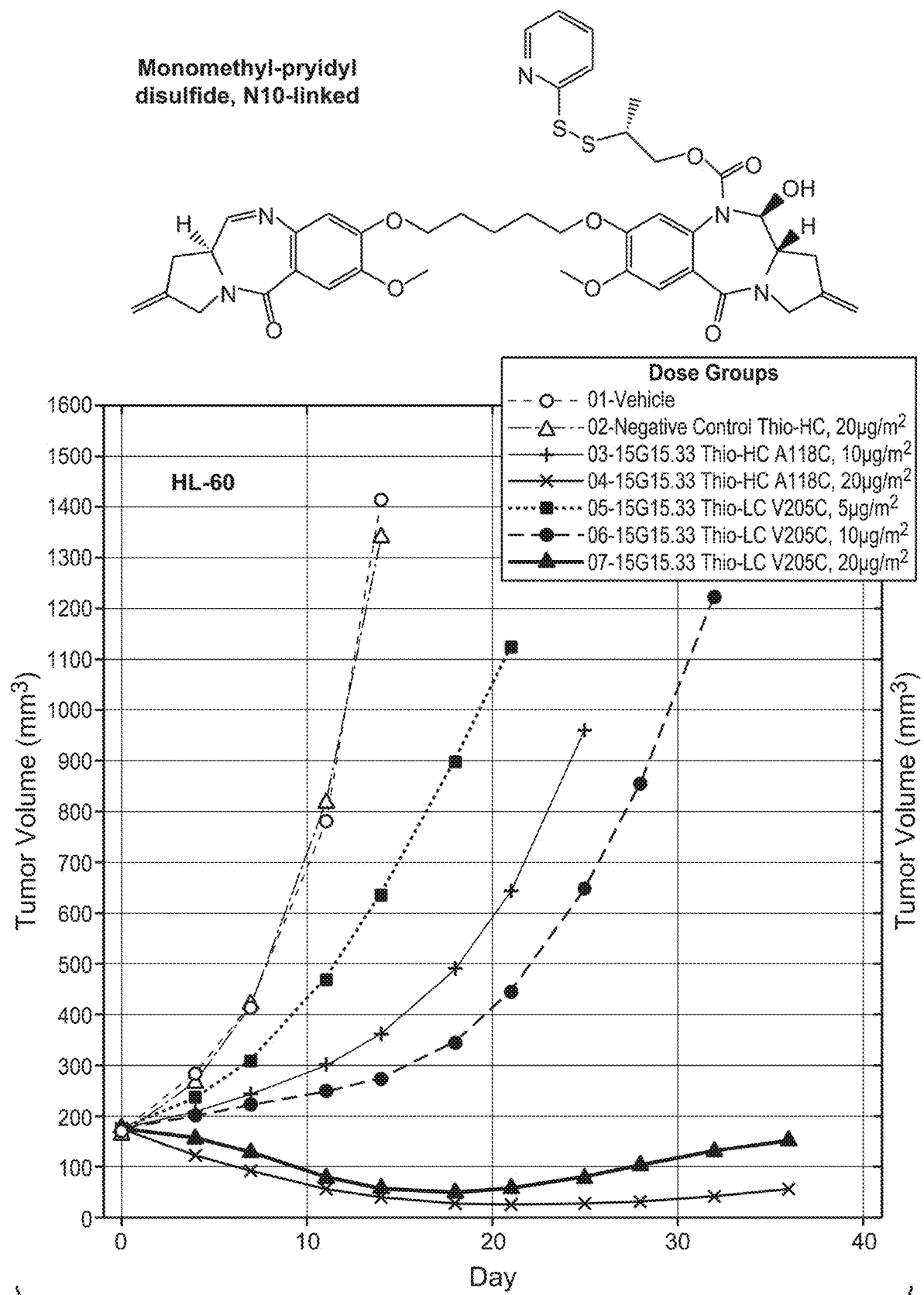
FIG. 16A-16B shows change in tumor volume (mm³) over time upon treatment with 15G15.33 Thio-HC A118C L-D #1 (L-D #1 is made by conjugating the linker-drug moiety monomethyl-pyridyl disulfide, N10-linked pyrrolobenzodiazepine
Figure 16B:
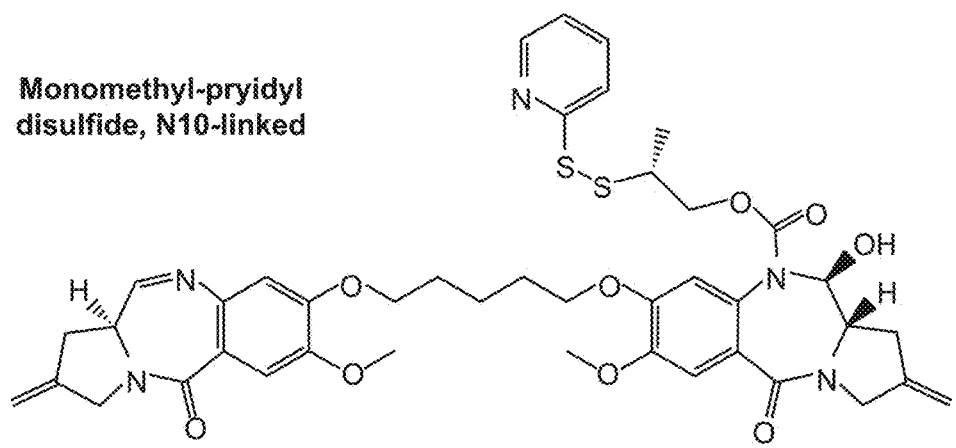

As shown in FIG. 16A-B, substantial tumor growth inhibition was achieved in both the HL-60 and EOL-1 models at the 1 mg/kg or 20 μg/m² dose of 15G15.33-L-D #1, while lower doses resulted in retarded tumor growth compared to the negative control antibody-drug conjugate. As shown in FIG. 17, a single 11.9 mg/kg dose of 15G15 L-D #2 was found to retard tumor growth in the HL-60 model.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

| NAME | SEQUENCE | SEQ ID NO |
|---|---|---|
| Human CD33 (UniProt No. 20138) | MPLLLLLPLL WAGALAMDPN FWLQVQESVT VQEGLCVLVP CTFFHPIPYY DKNSPVHGYW FREGAIISRD SPVATNKLDQ EVQEETQGRF RLLGDPSRNN CSLSIVDARR RDNGSYFFRM ERGSTKYSYK SPQLSVHVTD LTHRPKILIP GTLEPGHSKN LTCSVSWACE QGTPPIFSWL SAAPTSLGPR TTHSSVLIIT PRPQDHGTNL TCQVKFAGAG VTTERTIQLN VTYVPQNPTT GIFPGDGSGK QETRAGVVHG AIGGAGVTAL LALCLCLIFF IVKTHRRKAA RTAVGRNDTH PTTGSASPKH QKKSKLHGPT ETSSCSGAAP TVEMDEELHY ASLNFHGMNP SKDTSTEYSE VRTQ | 1 |
| Ig-like V-type domain (amino acids 19-135 of full length CD33) | PNFWLQVQES VTVQEGLCVL VPCTFFHPIP YYDKNSPVHG YWFREGAIIS RDSPVATNKL DQEVQEETQG RFRLLGDPSR NNCSLSIVDA RRRDNGSYFF RMERGSTKYS YKSPQLS | 2 |
| Ig-like C-type domain (amino acids 145-228 of full length CD33) | PKILIPGTLE PGHSKNLTCS VSWACEQGTP PIFSWLSAAP TSLGPRTTHS SVLIITPRPQ DHGTNLTCQV KFAGAGVTTE RTIQ | 3 |
| Cyno CD33 | MPLLLLPLLWAGALAMDPRVRLEVQESVTVQEGLCVLVPCTFFHPVPYHTRNSPVH GYWFREGAIVSLDSPVATNKLDQEVQEETQGRFRLLGDPSRNNCSLSIVDARRRDN GSYFFRMEKGSTKYSYKSTQLSVHVTDLTHRPQILIPGALDPDHSKNLTCSVPWAC EQGTPPIFSWMSAAPTSLGLRTTHSSVLIITPRPQDHGTNLTCQVKFPGAGVTTER TIQLNVSYASQNPRTDIFLGDGSGKQGVVQGAIGGAGVTVLLALCLCLIFFTVKTH RRKAARTAVGRIDTHPATGPTSSKHQKKSKLHGATETSGCSGTTLTVEMDEELHYA SLNFHGMNPSEDTSTEYSEVRTQ | 4 |
| 7A1, 9C2, 10D3, 15G15, 15G15.33, 15G15.37, 15G15.83, 15G15.88, 15G15.7, 15G15.17, 15G15.30, 15G15.31, 15G15.39, 15G15.84-HVR L1 | RSSQSLLHSNGYNYLD | 5 |
| 7A1, 9C2, 10D3, 15G15, 15G15.7, 15G15.17, 15G15.30, 15G15.31, 15G15.39, 15G15.84-HVR L2 | LGSNRAS | 6 |
| 7A1, 9C2, 10D3, 15G15, | MQALQTPWT | 7 |

-continued

Table of Sequences

| NAME | SEQUENCE | SEQ ID NO |
|---|---|---|
| 15G15.33, 15G15.37, 15G15.83, 15G15.88, 15G15.7, 15G15.17, 15G15.30, 15G15.31, 15G15.39, 15G15.84-HVR L3 | | |
| 7A1-HVR H1 | SYAVS | 8 |
| 7A1-HVR H2 | GIIPIFGTADYAQKFQG | 9 |
| 7A1-HVR H3 | ELADVFDI | 10 |
| 9C2-HVR H1 | SYSIS | 11 |
| 9C2-HVR H2 | EIIPIFGTADYAQKFQG | 12 |
| 9C2-HVR H3 | TWADAFDI | 13 |
| 9C3-HVR L1 | RASQGIRNDLG | 14 |
| 9C3-HVR L2 | AASSLQS | 15 |
| 9C3-HVR L3 | LQHNSYPWT | 16 |
| 9C3-HVR H1 | GNYMS | 17 |
| 9C3-HVR H2 | LIYSGDSTYYADSVKG | 18 |
| 9C3-HVR H3 | DGYYVSDMVV | 19 |
| 10D3-HVR H1 | SHAIS | 20 |
| 10D3-HVR H2 | GIIPIFGSANYAQKFQG | 21 |
| 10D3-HVR H3 | ELLDVFDI | 22 |
| 15G15, 15G15.33, 15G15.37, 15G15.83, 15G15.88, 15G15.17, 15G15.30, 15G15.31, 15G15.39, 15G15.84-HVR H1 | NHAIS | 23 |
| 15G15, 15G15.33, 15G15.37, 15G15.83, 15G15.88, 15G15.7, 15G15.17-HVR H2 | GIIPIFGTANYAQKFQG | 24 |
| 15G15, 15G15.33, 15G15.37, 15G15.83, 15G15.88, 15G15.7, 15G15.17, 15G15.30, | EWADVFDI | 25 |

-continued

Table of Sequences

| NAME | SEQUENCE | SEQ ID NO |
|---|---|---|
| 15G15.31, 15G15.39, 15G15.84-HVR H3 | | |
| 15G15.33-HVR L2 | LGVNSVS | 26 |
| 15G15.37-HVR L2 | LGSHRDS | 27 |
| 15G15.83-HVR L2 | LGAYTVS | 28 |
| 15G15.88-HVR L2 | LGNYRVS | 29 |
| 15G15.7-HVR H1 | GHKVS | 30 |
| 15G15.17-HVR H2 | GIIPILGLDYYAQKFQG | 31 |
| 15G15.30-HVR H2 | GIIPVLGYAYYAQKFQG | 32 |
| 15G15.31-HVR H2 | GIIPILGYAYYAQKFQG | 33 |
| 15G15.39-HVR H2 | GIIPILGISYYAQKFQG | 34 |
| 15G15.84-HVR H2 | SIIPVIGYDYYAQKFQG | 35 |
| 23E4-HVR L1 | RSSQTIVHSNGNTYLE | 36 |
| 23E4-HVR L2 | KVSNRFS | 37 |
| 23E4-HVR L3 | FQGSHVPPT | 38 |
| 23E4-HVR H1 | NYWMN | 39 |
| 23E4-HVR H2 | MIDPSDNETHYSQMFKD | 40 |
| 23E4-HVR H3 | YYGNFGWFVY | 41 |
| 27C6-HVR L1 | KASQDVGDAVA | 42 |
| 27C6-HVR L2 | WTSTRHT | 43 |
| 27C6-HVR L3 | QQYRSTPLT | 44 |
| 27C6, 33F3-HVR H1 | SYNMY | 45 |
| 27C6-HVR H2 | YIDPYNGGTRHNQKFKD | 46 |
| 27C6-HVR H3 | QNYEYFDY | 47 |
| 33F3-HVR L1 | KASQDVNTAVA | 48 |
| 33F3-HVR L2 | WASTRHT | 49 |
| 33F3-HVR L3 | QQHSGTPLT | 50 |
| 33F3-HVR H2 | YIDPYNGGTSYNQKFKG | Si |
| 33F3-HVR H3 | AAYFYFDY | 52 |
| 33F9-HVR L1 | LASQTIGTWLA | 53 |
| 33F9-HVR L2 | AATTLAD | 54 |

Table of Sequences

| NAME | SEQUENCE | SEQ ID NO |
|---|---|---|
| 33F9-HVR L3 | QQLYSTPLT | 55 |
| 33F9-HVR H1 | SYVMH | 56 |
| 33F9-HVR H2 | YINPYNDGTKYNDKFKG | 57 |
| 33F9-HVR H3 | GSNYEDFAMDY | 58 |
| 33H4-HVR L1 | RASESVDSYGNSYLH | 59 |
| 33H4-HVR L2 | LASNLES | 60 |
| 33H4-HVR L3 | QQNNEDPWT | 61 |
| 33H4-HVR H1 | TFPIE | 62 |
| 33H4-HVR H2 | NFHPYNDQTKYNEEFKG | 63 |
| 33H4-HVR H3 | GYYYAFDF | 64 |
| 7A1 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 65 |
| 7A1 $V_H$ | QVQLVQSGAE VKKPGSSVKV SCKASGGTFT SYAVSWVRQA PGQGLEWMGG IIPIFGTADY AQKFQGRVTI TADESTSTAY MELSSLRSED TAVYYCAREL ADVFDIWGQG TMVTVSS | 66 |
| 9C2 $V_L$ | DVVMTQSPLS LPVAPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKLE IK | 67 |
| 9C2 $V_H$ | QVQLVQSGAE VKKPGSSVKV SCKASGDTFS SYSISWVRQA PGQGLEWMGE IIPIFGTADY AQKFQGRVTI TADISTTTAY MELSSLRSED TAVYYCARTW ADAFDIWGQG TMVTVSS | 68 |
| 9C3 $V_L$ | DIQMTQSPSS LSASVGDRVT ITCRASQGIR NDLGWYQQKP GKAPKRLIYA ASSLQSGVPS RFSGSGSGTE FTLTISSLQP EDFATYYCLQ HNSYPWTFGQ GTKLEIK | 69 |
| 9C3 $V_H$ | EVQLVESGGA LIQPGGSLRL SCVASGFTIS GNYMSWVRQA PGKGLEWVSL IYSGDSTYYA DSVKGRFNIS RDISKNTVYL QMNSLRVEDT AVYYCVRDGY YVSDMVVWGK GTTVTVSS | 70 |
| 9C3.2 $V_L$ | DIQMTQSPSS LSASVGDRVT ITCRASQGIR NDLGWYQQKP GKAPKRLIYA ASSLQSGVPS RFSGSGSGTE FTLTISSLQP EDFATYYCLQ HNSYPWTFGQ GTKLEIK | 71 |
| 9C3.2 $V_H$ | EVQLVESGGA LIQPGGSLRL SCVASGFTIS GNYMSWVRQA PGKGLEWVSL IYSGDSTYYA DSVKGRFTIS RDISKNTVYL QMNSLRVEDT AVYYCVRDGY YVSDMVVWGK GTTVTVSS | 72 |
| 9C3.3 $V_L$ | DIQMTQSPSS LSASVGDRVT ITCRASQGIR NDLGWYQQKP GKAPKRLIYA ASSLQSGVPS RFSGSGSGTE FTLTISSLQP EDFATYYCLQ HNSYPWTFGQ GTKLEIK | 73 |
| 9C3.3 $V_H$ | EVQLVESGGA LIQPGGSLRL SCVASGFTIS GNYMSWVRQA PGKGLEWVSL IYSGDSTYYA DSVKGRFSIS RDISKNTVYL QMNSLRVEDT AVYYCVRDGY YVSDMVVWGK GTTVTVSS | 74 |
| 9C3.4 $V_L$ | DIQMTQSPSS LSASVGDRVT ITCRASQGIR NDLGWYQQKP GKAPKRLIYA ASSLQSGVPS RFSGSGSGTE FTLTISSLQP EDFATYYCLQ HNSYPWTFGQ GTKLEIK | 75 |
| 9C3.4 $V_H$ | EVQLVESGGA LIQPGGSLRL SCVASGFTIS GNYMSWVRQA PGKGLEWVSL IYSGDSTYYA DSVKGRFAIS RDISKNTVYL QMNSLRVEDT AVYYCVRDGY YVSDMVVWGK GTTVTVSS | 76 |
| 10D3 $V_L$ | DVVMTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 77 |

Table of Sequences

| NAME | SEQUENCE | SEQ ID NO |
|---|---|---|
| 10D3 $V_H$ | EVQLVESGAE VKKPGSSVKV SCKASGGTLI SHAISWVRQV PGQGLEWMGG IIPIFGSANY AQKFQGRVTI TADDSTNTAY LELSSLRSED TAVYYCAREL LDVFDIWGQG TMVTVSS | 78 |
| 15G15 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 79 |
| 15G15 $V_H$ | QVQLVQSGAE VKKPGSSVKV SCKASGGIFS NHAISWVRQA PGQGLEWMGG IIPIFGTANY AQKFQGRVTI TADESTSTAF MELSSLRSED TAVYYCAREW ADVFDIWGQG TMVTVSS | 80 |
| 15G15.33 $V_L$ | EIVLTQSPLS LPVTPGEPAS ISCRSSQSLL HSNGYNYLDW YLQKPGQSPQ LLIYLGVNSV SGVPDRFSGS GSGTDFTLKI SRVEAEDVGV YYCMQALQTP WTFGQGTKVE IK | 81 |
| 15G15.33 $V_H$ | QVQLVQSGAE VKKPGSSVKV SCKASGGIFS NHAISWVRQA PGQGLEWMGG IIPIFGTANY AQKFQGRVTI TADESTSTAF MELSSLRSED TAVYYCAREW ADVFDIWGQG TMVTVSS | 82 |
| 15G15.37 $V_L$ | EIVLTQSPLS LPVTPGEPAS ISCRSSQSLL HSNGYNYLDW YLQKPGQSPQ LLIYLGSHRD SGVPDRFSGS GSGTDFTLKI SRVEAEDVGV YYCMQALQTP WTFGQGTKVE IK | 83 |
| 15G15.37 $V_H$ | QVQLVQSGAE VKKPGSSVKV SCKASGGIFS NHAISWVRQA PGQGLEWMGG IIPIFGTANY AQKFQGRVTI TADESTSTAF MELSSLRSED TAVYYCAREW ADVFDIWGQG TMVTVSS | 84 |
| 15G15.83 $V_L$ | EIVLTQSPLS LPVTPGEPAS ISCRSSQSLL HSNGYNYLDW YLQKPGQSPQ LLIYLGAYTV SGVPDRFSGS GSGTDFTLKI SRVEAEDVGV YYCMQALQTP WTFGQGTKVE IK | 85 |
| 15G15.83 $V_H$ | QVQLVQSGAE VKKPGSSVKV SCKASGGIFS NHAISWVRQA PGQGLEWMGG IIPIFGTANY AQKFQGRVTI TADESTSTAF MELSSLRSED TAVYYCAREW ADVFDIWGQG TMVTVSS | 86 |
| 15G15.88 $V_L$ | EIVLTQSPLS LPVTPGEPAS ISCRSSQSLL HSNGYNYLDW YLQKPGQSPQ LLIYLGNYRV SGVPDRFSGS GSGTDFTLKI SRVEAEDVGV YYCMQALQTP WTFGQGTKVE IK | 87 |
| 15G15.88 $V_H$ | QVQLVQSGAE VKKPGSSVKV SCKASGGIFS NHAISWVRQA PGQGLEWMGG IIPIFGTANY AQKFQGRVTI TADESTSTAF MELSSLRSED TAVYYCAREW ADVFDIWGQG TMVTVSS | 88 |
| 15G15.7 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 89 |
| 15G15.7 $V_H$ | QVQLVQSGAE VKKPGSSVKV SCKASGGIFS GHKVSWVRQA PGQGLEWMGG IIPIFGTANY AQKFQGRVTI TADESTSTAF MELSSLRSED TAVYYCAREW ADVFDIWGQG TMVTVSS | 90 |
| 15G15.17 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 91 |
| 15G15.17 $V_H$ | QVQLVQSGAE VKKPGSSVKV SCKASGGIFS NHAISWVRQA PGQGLEWMGG IIPILGLDYY AQKFQGRVTI TADESTSTAF MELSSLRSED TAVYYCAREW ADVFDIWGQG TMVTVSS | 92 |
| 15G15.30 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 93 |
| 15G15.30 $V_H$ | QVQLVQSGAE VKKPGSSVKV SCKASGGIFS NHAISWVRQA PGQGLEWMGG IIPVLGYAYY AQKFQGRVTI TADESTSTAF MELSSLRSED TAVYYCAREW ADVFDIWGQG TMVTVSS | 94 |
| 15G15.31 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 95 |

Table of Sequences

| NAME | SEQUENCE | SEQ ID NO |
|---|---|---|
| 15G15.31 $V_H$ | QVQLVQSGAE VKKPGSSVKV SCKASGGIFS NHAISWVRQA PGQGLEWMGG IIPILGYAYY AQKFQGRVTI TADESTSTAF MELSSLRSED TAVYYCAREW ADVFDIWGQG TMVTVSS | 96 |
| 15G15.39 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 97 |
| 15G15.39 $V_H$ | QVQLVQSGAE VKKPGSSVKV SCKASGGIFS NHAISWVRQA PGQGLEWMGG IIPILGISYY AQKFQGRVTI TADESTSTAF MELSSLRSED TAVYYCAREW ADVFDIWGQG TMVTVSS | 98 |
| 15G15.84 $V_L$ | EIVLTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK | 99 |
| 15G15.84 $V_H$ | QVQLVQSGAE VKKPGSSVKV SCKASGGIFS NHAISWVRQA PGQGLEWMGS IIPVIGYDYY AQKFQGRVTI TADESTSTAF MELSSLRSED TAVYYCAREW ADVFDIWGQG TMVTVSS | 100 |
| 23E4 $V_L$ | DIFMTQTPLS LPVSLGDPAS ISCRSSQTIV HSNGNTYLEW YLQKPGQSPK LLIYKVSNRF SGVPDRFSGS GSGTDFTLKI SRVEAEDLGV YYCFQGSHVP PTFGGGTKVE IK | 101 |
| 23E4 $V_H$ | EVQLQQSGAE LVRPGASVKL SCKASGYTFT NYWMNWVKQR PGQGLEWIGM IDPSDNETHY SQMFKDKATL TVDKSSSTAY MQLISLTSED SAVYYCAGYY GNFGWFVYWG QGTLVTVSA | 102 |
| 27C6 $V_L$ | DIVLTQSPKF MSTSVGDRVS ITCKASQDVG DAVAWYQQKP GQSPKLLFYW TSTRHTGVPD RFTGSGSGTE FTLTIRNVQS EDLADYFCQQ YRSTPLTFGS GTKVEIK | 103 |
| 27C6 $V_H$ | EVQLQQSGPE LVKPGASVKV SCKASGYAFT SYNMYWVKQS HGKSLEWIGY IDPYNGGTRH NQKFKDKATL TVDKSSSTAY MHLNSLTSED SAVYYCASQN YEYFDYWGQG TTLTVSS | 104 |
| 33F3 $V_L$ | EIQMTQSPKF MSTSVGDRVS ITCKASQDVN TAVAWYQQKP GQSPKLLIYW ASTRHTGVPD RFTGSGSGTD YTLTISSVQA EDLALYYCQQ HSGTPLTFGA GTKVEIK | 105 |
| 33F3 $V_H$ | EVQLQQSGPE LVKPGASVKV SCKASGYAFT SYNMYWVKQS HGKSLEWIGY IDPYNGGTSY NQKFKGKATL TVDKSSSTAY MHLNSLTSED SAVFCAPAA YFYFDYWGQG TTLTVSS | 106 |
| 33F9 $V_L$ | DIVMTQSPAS QSASLGESVT ITCLASQTIG TWLAWYQQKP GKSPQLLIYA ATTLADGVPS RFSGSGSGTK FSFKISSLQA EDFVSYYCQQ LYSTPLTFGG GTKVEIK | 107 |
| 33F9 $V_H$ | EVQLQQSGPE LVKPGASVKM SCKASGYTFT SYVMHWMKQK PGQGLEWIGY INPYNDGTKY NDKFKGKATL TSDKSSSTAY MELSSLTSED SAVYYCARGS NYEDFAMDYR GQGTSVTVSS | 108 |
| 33H4 $V_L$ | DIQMTQSPAS LTVSLGQRAT ISCRASESVD SYGNSYLHWY QQKPGQPPQL LIYLASNLES GVPARFSGSG SRTDFTLTID PVEADDAATY YCQQNNEDPW TFGGGTKVEI K | 109 |
| 33H4 $V_H$ | EVQLQQSGAE LVKPGASVKM SCKAFGYTFT TFPIEWMKQS HGKSLEWIGN FHPYNDQTKY NEEFKGRAKL TIDRSSSTVY LELGRLTSDD SAVYYCARGY YYAFDFWGQG TTLTVSS | 110 |
| CON1-HVR L2 | LGX$_1$X$_2$X$_3$X$_4$S, wherein X$_1$ is S, V, A or N, X$_2$ is N, H, or Y, X$_3$ is R, S, or T, and X$_4$ is A, V, or D | 111 |
| CON1-HVR H1 | X$_5$X$_6$X$_7$X$_8$S, wherein X$_5$ is S, N, or G, X$_6$ is Y or H, X$_7$ is A, S, or K, and X$_8$ is V or I | 112 |
| CON1-HVR H2 | X$_9$IIPX$_{10}$X$_{11}$GX$_{12}$X$_{13}$X$_{14}$YAQKFQG, wherein X9 is G, E, or S, X$_{10}$ is I or V, X$_{11}$ is F, L, or I, X$_{12}$ is T, S, L, Y, or I, X$_{13}$ is A, D, or S, and X$_{14}$ is D, N, or Y | 113 |

Table of Sequences

| NAME | SEQUENCE | SEQ ID NO |
|---|---|---|
| CON1-HVR H3 | $X_{15}X_{16}X_{17}DX_{18}FDI$, wherein $X_{15}$ is E or T, $X_{16}$ is L or W, $X_{17}$ is A or L, $X_{18}$ is V or A | 114 |
| CON2-HVR H1 | $X_{19}X_{20}X_{21}X_{22}S$, wherein $X_{19}$ is S or N, $X_{20}$ is Y or H, $X_{21}$ is A or S, and $X_{22}$ is V or I | 115 |
| CON2-HVR H2 | $X_{23}IIPIFGX_{24}AX_{25}YAQKFQG$, wherein $X_{23}$ is G or E, $X_{24}$ is T or S, $X_{25}$ is D or N | 116 |
| CON2-HVR H3 | $X_{26}X_{27}X_{28}DX_{29}FDI$, wherein $X_{26}$ is E or T, $X_{27}$ is L or W, $X_{28}$ is A or L, $X_{29}$ is V or A | 117 |
| CON3-HVR H1 | $X_{30}HX_{31}X_{32}S$, wherein $X_{30}$ is N or G, $X_{31}$ is A or K, and $X_{32}$ is V or I | 118 |
| CON3-HVR H2 | $X_{31}IIPX_{32}X_{33}GX_{34}X_{35}X_{36}YAQKFQG$, wherein $X_{31}$ is G or S, $X_{32}$ is I or V, $X_{33}$ is F, L, or I, $X_{34}$ is T, L, Y, or I, $X_{35}$ is A, D, or S, and X14 is N or Y | 119 |
| V205C cysteine engineered light chain constant region (Igκ) | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPCTKS FNRGEC | 120 |
| A118C cysteine engineered heavy chain constant region (IgG1) | CSTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK | 121 |

What is claimed is:

1. An isolated antibody that binds to CD33, wherein the antibody comprises:
    (i) (a) HVR-H1 comprising the amino acid sequence of SEQ ID NO:39; (b) HVR-H2 comprising the amino acid sequence of SEQ ID NO:40; (c) HVR-H3 comprising the amino acid sequence of SEQ ID NO:41; (d) HVR-L1 comprising the amino acid sequence of SEQ ID NO:36; (e) HVR-L2 comprising the amino acid sequence of SEQ ID NO:37; and (f) HVR-L3 comprising the amino acid sequence of SEQ ID NO:38;
    (ii) (a) HVR-H1 comprising the amino acid sequence of SEQ ID NO:45; (b) HVR-H2 comprising the amino acid sequence of SEQ ID NO:46; (c) HVR-H3 comprising the amino acid sequence of SEQ ID NO:47; (d) HVR-L1 comprising the amino acid sequence of SEQ ID NO:42; (e) HVR-L2 comprising the amino acid sequence of SEQ ID NO:43; and (f) HVR-L3 comprising the amino acid sequence of SEQ ID NO:44;
    (iii) (a) HVR-H1 comprising the amino acid sequence of SEQ ID NO:45; (b) HVR-H2 comprising the amino acid sequence of SEQ ID NO:51; (c) HVR-H3 comprising the amino acid sequence of SEQ ID NO:52; (d) HVR-L1 comprising the amino acid sequence of SEQ ID NO:48; (e) HVR-L2 comprising the amino acid sequence of SEQ ID NO:49; and (f) HVR-L3 comprising the amino acid sequence of SEQ ID NO:50;
    (iv) (a) HVR-H1 comprising the amino acid sequence of SEQ ID NO:56; (b) HVR-H2 comprising the amino acid sequence of SEQ ID NO:57; (c) HVR-H3 comprising the amino acid sequence of SEQ ID NO:58; (d) HVR-L1 comprising the amino acid sequence of SEQ ID NO:53; (e) HVR-L2 comprising the amino acid sequence of SEQ ID NO:54; and (f) HVR-L3 comprising the amino acid sequence of SEQ ID NO:55; or
    (v) (a) HVR-H1 comprising the amino acid sequence of SEQ ID NO:62; (b) HVR-H2 comprising the amino acid sequence of SEQ ID NO:63; (c) HVR-H3 comprising the amino acid sequence of SEQ ID NO:64; (d) HVR-L1 comprising the amino acid sequence of SEQ ID NO:59; (e) HVR-L2 comprising the amino acid sequence of SEQ ID NO:60; and (f) HVR-L3 comprising the amino acid sequence of SEQ ID NO:61.

2. The antibody of claim 1, wherein the antibody comprises:
    a) a heavy chain variable region comprising the sequence of SEQ ID NO: 102 and a light chain variable region comprising the sequence of SEQ ID NO: 101;
    b) a heavy chain variable region comprising the sequence of SEQ ID NO: 104 and a light chain variable region comprising the sequence of SEQ ID NO: 103;
    c) a heavy chain variable region comprising the sequence of SEQ ID NO: 106 and a light chain variable region comprising the sequence of SEQ ID NO: 105;
    d) a heavy chain variable region comprising the sequence of SEQ ID NO: 108 and a light chain variable region comprising the sequence of SEQ ID NO: 107; or
    e) a heavy chain variable region comprising the sequence of SEQ ID NO: 110 and a light chain variable region comprising the sequence of SEQ ID NO: 109.

3. The antibody of claim 1, wherein the antibody has one or more of the following characteristics:
    a) binds to recombinant human CD33;
    b) binds to recombinant cynomolgus monkey CD33;
    c) binds to endogenous CD33 on the surface of human peripheral blood mononucleocytes (PBMCs);
    d) binds to endogenous CD33 on the surface of cynomolgus monkey PBMCs;
    e) binds to endogenous CD33 on the surface of a cancer cell;
    f) binds to endogenous CD33 on the surface of an AML cancer cell;
    g) binds to endogenous CD33 on the surface of Molm-13 cells;
    h) binds to CD33 comprising a R69G mutation;
    i) binds to endogenous human CD33 with a Kd of less than 15 nM, less than 10 nM, less than 7 nM, less than 5 nM, or less than 3 nM;
    j) binds to recombinant human CD33 with a Kd of less than 10 nM, less than 7 nM, less than 5 nM, or less than 3 nM; and/or
    k) binds to recombinant cynomolgus monkey CD33 with a Kd of less than 10 nM, less than 7 nM, less than 5 nM, or less than 3 nM, less than 2 nM, or less than 1 nM.

4. The antibody of claim 1, which is a monoclonal antibody.

5. The antibody of claim 1, which is a humanized or chimeric antibody.

6. The antibody of claim 1, which is an antibody fragment that binds CD33.

7. The antibody of claim 1, wherein CD33 is human CD33 comprising amino acids 18 to 364 of SEQ ID NO: 1.

8. The antibody of claim 1, which is an IgG1, IgG2a or IgG2b antibody.

9. An isolated nucleic acid encoding the antibody of claim 1.

10. A host cell comprising the nucleic acid of claim 9.

11. A method of producing an antibody comprising culturing the host cell of claim 10 so that the antibody is produced.

12. The method of claim 11, further comprising isolating the antibody.

13. An immunoconjugate comprising the antibody of claim 1 and a cytotoxic agent.

14. The immunoconjugate of claim 13 having the formula Ab-(L-D)p, wherein:

(a) Ab is the antibody;
(b) L is a linker;
(c) D is a cytotoxic agent; and
(d) p ranges from 1-8.

15. The immunoconjugate of claim 13, wherein the cytotoxic agent is selected from a maytansinoid, a calicheamicin, a pyrrolobenzodiazepine, and a nemorubicin derivative.

16. The immunoconjugate of claim 14, wherein D is a pyrrolobenzodiazepine of Formula A:

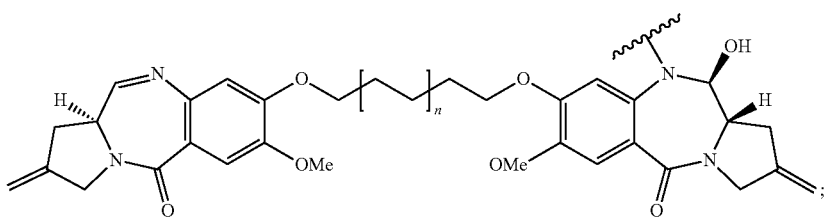

wherein the dotted lines indicate the optional presence of a double bond between C1 and C2 or C2 and C3;

$R^2$ is independently selected from H, OH, =O, =$CH_2$, CN, R, OR, =CH—$R^D$, =C($R^D$)$_2$, O—$SO_2$—R, $CO_2$R and COR, and optionally further selected from halo or dihalo, wherein $R^D$ is independently selected from R, $CO_2$R, COR, CHO, $CO_2$H, and halo;

$R^6$ and $R^9$ are independently selected from H, R, OH, OR, SH, SR, $NH_2$, NHR, NRR', $NO_2$, $Me_3$Sn and halo;

$R^7$ is independently selected from H, R, OH, OR, SH, SR, $NH_2$, NHR, NRR', $NO_2$, $Me_3$Sn and halo;

Q is independently selected from O, S and NH;

$R^{11}$ is either H, or R or, where Q is O, $SO_3$M, where M is a metal cation;

R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms and/or aromatic rings that are optionally substituted; and X and X' are independently selected from O, S and N(H).

17. The immunoconjugate of claim 14, wherein D has the structure:

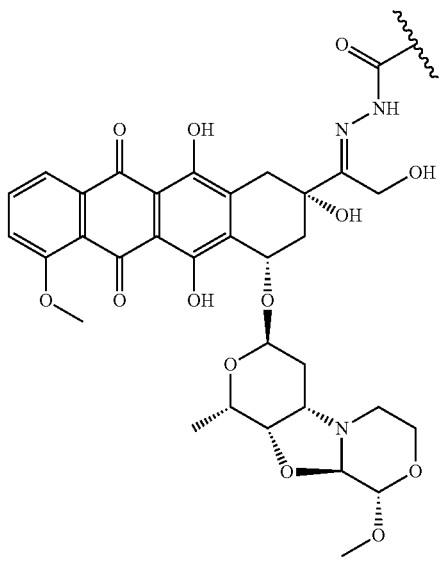

wherein n is 0 or 1.

18. The immunoconjugate of claim 14, wherein D is a nemorubicin derivative.

19. The immunoconjugate of claim 18, wherein D has a structure selected from:

; and

-continued

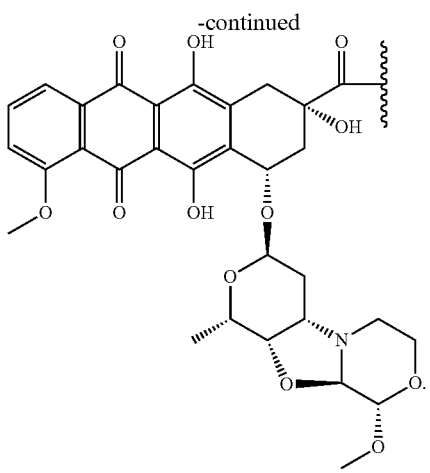

20. The immunoconjugate of claim 14, wherein the linker is cleavable by a protease.

21. The immunoconjugate of claim 14, wherein the linker is acid-labile.

22. The immunoconjugate of claim 21, wherein the linker comprises hydrazone.

23. The immunoconjugate of claim 19 having a formula selected from:

24. The immunoconjugate of claim 14, wherein p ranges from 2-5.

25. A pharmaceutical formulation comprising the immunoconjugate of claim 13 and a pharmaceutically acceptable carrier.

26. The pharmaceutical formulation of claim 25, further comprising an additional therapeutic agent.

27. A method of treating an individual having a CD33-positive cancer, the method comprising administering to the individual an effective amount of the immunoconjugate of claim 13.

28. The method of claim 27, wherein the CD33-positive cancer is AML.

29. The method of claim 27, further comprising administering an additional therapeutic agent to the individual.

30. A method of inhibiting proliferation of a CD33-positive cell, the method comprising exposing the cell to the immunoconjugate of claim 13 under conditions permissive for binding of the immunoconjugate to CD33 on the surface of the cell, thereby inhibiting proliferation of the cell.

31. The method of claim 30, wherein the cell is an AML cancer cell.

32. The antibody of claim 1, wherein the antibody is conjugated to a label.

33. The antibody of claim 32, wherein the label is a positron emitter.

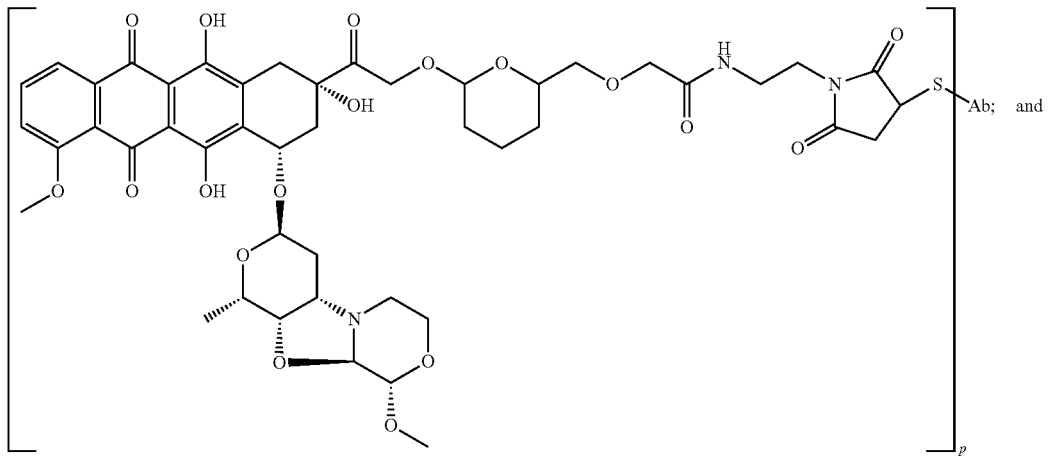

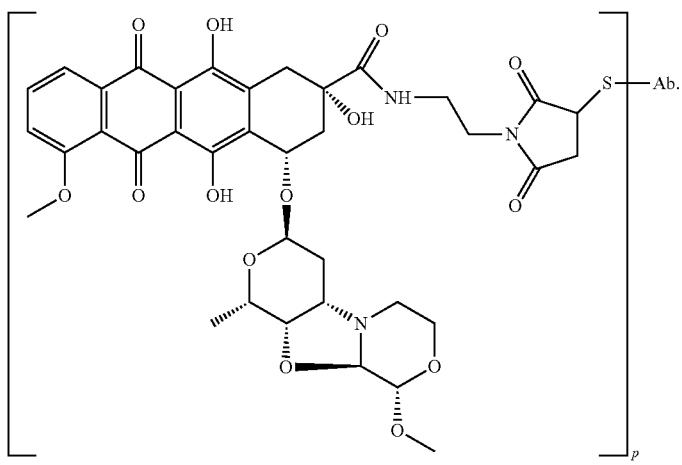

34. The antibody of claim 33, wherein the positron emitter is $^{89}$Zr.

35. A method of detecting human CD33 in a biological sample comprising contacting the biological sample with the anti-CD33 antibody of claim 1 under conditions permissive for binding of the anti-CD33 antibody to a naturally occurring human CD33, and detecting whether a complex is formed between the anti-CD33 antibody and a naturally occurring human CD33 in the biological sample.

36. The method of claim 35, wherein the biological sample is a AML endometrial cancer sample.

37. A method for detecting a CD33-positive cancer comprising (i) administering a labeled anti-CD33 antibody to a subject having or suspected of having a CD33-positive cancer, wherein the labeled anti-CD33 antibody comprises the anti-CD33 antibody of claim 1, and (ii) detecting the labeled anti-CD33 antibody in the subject, wherein detection of the labeled anti-CD33 antibody indicates a CD33-positive cancer in the subject.

38. The method of claim 37, wherein the labeled anti-CD33 antibody comprises an anti-CD33 antibody conjugated to a positron emitter.

39. The method of claim 38, wherein the positron emitter is $^{89}$Zr.

\* \* \* \* \*

SEQUENCE LISTING

<160> NUMBER OF SEQ ID NOS: 124

<210> SEQ ID NO 1
<211> LENGTH: 364
<212> TYPE: PRT
<213> ORGANISM: Homo sapiens

<400> SEQUENCE: 1

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg

```
            130                 135                 140
Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
            195                 200                 205

Asn Leu Thr Cys Gln Val Lys Phe Ala Gly Ala Gly Val Thr Thr Glu
            210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
                260                 265                 270

Leu Cys Leu Cys Leu Ile Phe Phe Ile Val Lys Thr His Arg Arg Lys
            275                 280                 285

Ala Ala Arg Thr Ala Val Gly Arg Asn Asp Thr His Pro Thr Thr Gly
290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
            355                 360

<210> SEQ ID NO 2
<211> LENGTH: 117
<212> TYPE: PRT
<213> ORGANISM: Artificial sequence
<220> FEATURE:
<223> OTHER INFORMATION: Synthetic

<400> SEQUENCE: 2

Pro Asn Phe Trp Leu Gln Val Gln Glu Ser Val Thr Val Gln Glu Gly
1               5                   10                  15

Leu Cys Val Leu Val Pro Cys Thr Phe Phe His Pro Ile Pro Tyr Tyr
                20                  25                  30

Asp Lys Asn Ser Pro Val His Gly Tyr Trp Phe Arg Glu Gly Ala Ile
            35                  40                  45

Ile Ser Arg Asp Ser Pro Val Ala Thr Asn Lys Leu Asp Gln Glu Val
        50                  55                  60

Gln Glu Glu Thr Gln Gly Arg Phe Arg Leu Leu Gly Asp Pro Ser Arg
65                  70                  75                  80

Asn Asn Cys Ser Leu Ser Ile Val Asp Ala Arg Arg Arg Asp Asn Gly
                85                  90                  95

Ser Tyr Phe Phe Arg Met Glu Arg Gly Ser Thr Lys Tyr Ser Tyr Lys
                100                 105                 110

Ser Pro Gln Leu Ser
            115
```

```
<210> SEQ ID NO 3
<211> LENGTH: 84
<212> TYPE: PRT
<213> ORGANISM: Artificial sequence
<220> FEATURE:
<223> OTHER INFORMATION: Synthetic

<400> SEQUENCE: 3

Pro Lys Ile Leu Ile Pro Gly Thr Leu Glu Pro Gly His Ser Lys Asn
1               5                   10                  15

Leu Thr Cys Ser Val Ser Trp Ala Cys Glu Gln Gly Thr Pro Pro Ile
            20                  25                  30

Phe Ser Trp Leu Ser Ala Ala Pro Thr Ser Leu Gly Pro Arg Thr Thr
        35                  40                  45

His Ser Ser Val Leu Ile Ile Thr Pro Arg Pro Gln Asp His Gly Thr
    50                  55                  60

Asn Leu Thr Cys Gln Val Lys Phe Ala Gly Ala Gly Val Thr Thr Glu
65                  70                  75                  80

Arg Thr Ile Gln

<210> SEQ ID NO 4
<211> LENGTH: 359
<212> TYPE: PRT
<213> ORGANISM: Macaca fascicularis

<400> SEQUENCE: 4

Met Pro Leu Leu Leu Leu Pro Leu Leu Trp Ala Gly Ala Leu Ala Met
1               5                   10                  15

Asp Pro Arg Val Arg Leu Glu Val Gln Glu Ser Val Thr Val Gln Glu
            20                  25                  30

Gly Leu Cys Val Leu Val Pro Cys Thr Phe Phe His Pro Val Pro Tyr
        35                  40                  45

His Thr Arg Asn Ser Pro Val His Gly Tyr Trp Phe Arg Glu Gly Ala
    50                  55                  60

Ile Val Ser Leu Asp Ser Pro Val Ala Thr Asn Lys Leu Asp Gln Glu
65                  70                  75                  80

Val Gln Glu Glu Thr Gln Gly Arg Phe Arg Leu Leu Gly Asp Pro Ser
            85                  90                  95

Arg Asn Asn Cys Ser Leu Ser Ile Val Asp Ala Arg Arg Arg Asp Asn
        100                 105                 110

Gly Ser Tyr Phe Phe Arg Met Glu Lys Gly Ser Thr Lys Tyr Ser Tyr
    115                 120                 125

Lys Ser Thr Gln Leu Ser Val His Val Thr Asp Leu Thr His Arg Pro
130                 135                 140

Gln Ile Leu Ile Pro Gly Ala Leu Asp Pro Asp His Ser Lys Asn Leu
145                 150                 155                 160

Thr Cys Ser Val Pro Trp Ala Cys Glu Gln Gly Thr Pro Pro Ile Phe
            165                 170                 175

Ser Trp Met Ser Ala Ala Pro Thr Ser Leu Gly Leu Arg Thr Thr His
        180                 185                 190

Ser Ser Val Leu Ile Ile Thr Pro Arg Pro Gln Asp His Gly Thr Asn
    195                 200                 205

Leu Thr Cys Gln Val Lys Phe Pro Gly Ala Gly Val Thr Thr Glu Arg
210                 215                 220

Thr Ile Gln Leu Asn Val Ser Tyr Ala Ser Gln Asn Pro Arg Thr Asp
225                 230                 235                 240
```

Ile Phe Leu Gly Asp Gly Ser Gly Lys Gln Gly Val Val Gln Gly Ala
                245                 250                 255

Ile Gly Gly Ala Gly Val Thr Val Leu Leu Ala Leu Cys Leu Cys Leu
            260                 265                 270

Ile Phe Phe Thr Val Lys Thr His Arg Arg Lys Ala Ala Arg Thr Ala
        275                 280                 285

Val Gly Arg Ile Asp Thr His Pro Ala Thr Gly Pro Thr Ser Ser Lys
    290                 295                 300

His Gln Lys Lys Ser Lys Leu His Gly Ala Thr Glu Thr Ser Gly Cys
305                 310                 315                 320

Ser Gly Thr Thr Leu Thr Val Glu Met Asp Glu Glu Leu His Tyr Ala
                325                 330                 335

Ser Leu Asn Phe His Gly Met Asn Pro Ser Glu Asp Thr Ser Thr Glu
            340                 345                 350

Tyr Ser Glu Val Arg Thr Gln
        355

<210> SEQ ID NO 5
<211> LENGTH: 16
<212> TYPE: PRT
<213> ORGANISM: Artificial sequence
<220> FEATURE:
<223> OTHER INFORMATION: Synthetic

<400> SEQUENCE: 5

Arg Ser Ser Gln Ser Leu Leu His Ser Asn Gly Tyr Asn Tyr Leu Asp
1               5                   10                  15

<210> SEQ ID NO 6
<211> LENGTH: 7
<212> TYPE: PRT
<213> ORGANISM: Artificial sequence
<220> FEATURE:
<223> OTHER INFORMATION: Synthetic

<400> SEQUENCE: 6

Leu Gly Ser Asn Arg Ala Ser
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic

<400> SEQUENCE: 7

Met Gln Ala Leu Gln Thr Pro Trp Thr
1               5

<210> SEQ ID NO 8
<211> LENGTH: 5
<212> TYPE: PRT
<213> ORGANISM: Artificial sequence
<220> FEATURE:
<223> OTHER INFORMATION: Synthetic

<400> SEQUENCE: 8

Ser Tyr Ala Val Ser
1               5

<210> SEQ ID NO 9
<211> LENGTH: 17

```
<212> TYPE: PRT
<213> ORGANISM: Artificial sequence
<220> FEATURE:
<223> OTHER INFORMATION: Synthetic

<400> SEQUENCE: 9

Gly Ile Ile Pro Ile Phe Gly Thr Ala Asp Tyr Ala Gln Lys Phe Gln
1               5                   10                  15
Gly

<210> SEQ ID NO 10
<211> LENGTH: 8
<212> TYPE: PRT
<213> ORGANISM: Artificial sequence
<220> FEATURE:
<223> OTHER INFORMATION: Synthetic

<400> SEQUENCE: 10

Glu Leu Ala Asp Val Phe Asp Ile
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic

<400> SEQUENCE: 11

Ser Tyr Ser Ile Ser
1               5

<210> SEQ ID NO 12
<211> LENGTH: 17
<212> TYPE: PRT
<213> ORGANISM: Artificial sequence
<220> FEATURE:
<223> OTHER INFORMATION: Synthetic

<400> SEQUENCE: 12

Glu Ile Ile Pro Ile Phe Gly Thr Ala Asp Tyr Ala Gln Lys Phe Gln
1               5                   10                  15
Gly

<210> SEQ ID NO 13
<211> LENGTH: 8
<212> TYPE: PRT
<213> ORGANISM: Artificial sequence
<220> FEATURE:
<223> OTHER INFORMATION: Synthetic

<400> SEQUENCE: 13

Thr Trp Ala Asp Ala Phe Asp Ile
1               5

<210> SEQ ID NO 14
<211> LENGTH: 11
<212> TYPE: PRT
<213> ORGANISM: Artificial sequence
<220> FEATURE:
<223> OTHER INFORMATION: Synthetic

<400> SEQUENCE: 14

Arg Ala Ser Gln Gly Ile Arg Asn Asp Leu Gly
1               5                   10
```

```
<210> SEQ ID NO 15
<211> LENGTH: 7
<212> TYPE: PRT
<213> ORGANISM: Artificial sequence
<220> FEATURE:
<223> OTHER INFORMATION: Synthetic

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic

<400> SEQUENCE: 16

Leu Gln His Asn Ser Tyr Pro Trp Thr
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic

<400> SEQUENCE: 17

Gly Asn Tyr Met Ser
1               5

<210> SEQ ID NO 18
<211> LENGTH: 16
<212> TYPE: PRT
<213> ORGANISM: Artificial sequence
<220> FEATURE:
<223> OTHER INFORMATION: Synthetic

<400> SEQUENCE: 18

Leu Ile Tyr Ser Gly Asp Ser Thr Tyr Tyr Ala Asp Ser Val Lys Gly
1               5                   10                  15

<210> SEQ ID NO 19
<211> LENGTH: 10
<212> TYPE: PRT
<213> ORGANISM: Artificial sequence
<220> FEATURE:
<223> OTHER INFORMATION: Synthetic

<400> SEQUENCE: 19

Asp Gly Tyr Tyr Val Ser Asp Met Val Val
1               5                   10

<210> SEQ ID NO 20
<211> LENGTH: 5
<212> TYPE: PRT
<213> ORGANISM: Artificial sequence
<220> FEATURE:
<223> OTHER INFORMATION: Synthetic

<400> SEQUENCE: 20

Ser His Ala Ile Ser
1               5
```

```
<210> SEQ ID NO 21
<211> LENGTH: 17
<212> TYPE: PRT
<213> ORGANISM: Artificial sequence
<220> FEATURE:
<223> OTHER INFORMATION: Synthetic

<400> SEQUENCE: 21

Gly Ile Ile Pro Ile Phe Gly Ser Ala Asn Tyr Ala Gln Lys Phe Gln
1               5                   10                  15

Gly

<210> SEQ ID NO 22
<211> LENGTH: 8
<212> TYPE: PRT
<213> ORGANISM: Artificial sequence
<220> FEATURE:
<223> OTHER INFORMATION: Synthetic

<400> SEQUENCE: 22

Glu Leu Leu Asp Val Phe Asp Ile
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic

<400> SEQUENCE: 23

Asn His Ala Ile Ser
1               5

<210> SEQ ID NO 24
<211> LENGTH: 17
<212> TYPE: PRT
<213> ORGANISM: Artificial sequence
<220> FEATURE:
<223> OTHER INFORMATION: Synthetic

<400> SEQUENCE: 24

Gly Ile Ile Pro Ile Phe Gly Thr Ala Asn Tyr Ala Gln Lys Phe Gln
1               5                   10                  15

Gly

<210> SEQ ID NO 25
<211> LENGTH: 8
<212> TYPE: PRT
<213> ORGANISM: Artificial sequence
<220> FEATURE:
<223> OTHER INFORMATION: Synthetic

<400> SEQUENCE: 25

Glu Trp Ala Asp Val Phe Asp Ile
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic

<400> SEQUENCE: 26

Leu Gly Val Asn Ser Val Ser
```

```
1               5
```

<210> SEQ ID NO 27
<211> LENGTH: 7
<212> TYPE: PRT
<213> ORGANISM: Artificial sequence
<220> FEATURE:
<223> OTHER INFORMATION: Synthetic

<400> SEQUENCE: 27

```
Leu Gly Ser His Arg Asp Ser
1               5
```

<210> SEQ ID NO 28
<211> LENGTH: 7
<212> TYPE: PRT
<213> ORGANISM: Artificial sequence
<220> FEATURE:
<223> OTHER INFORMATION: Synthetic

<400> SEQUENCE: 28

```
Leu Gly Ala Tyr Thr Val Ser
1               5
```

<210> SEQ ID NO 29
<211> LENGTH: 7
<212> TYPE: PRT
<213> ORGANISM: Artificial sequence
<220> FEATURE:
<223> OTHER INFORMATION: Synthetic

<400> SEQUENCE: 29

```
Leu Gly Asn Tyr Arg Val Ser
1               5
```

<210> SEQ ID NO 30
<211> LENGTH: 5
<212> TYPE: PRT
<213> ORGANISM: Artificial sequence
<220> FEATURE:
<223> OTHER INFORMATION: Synthetic

<400> SEQUENCE: 30

```
Gly His Lys Val Ser
1               5
```

<210> SEQ ID NO 31
<211> LENGTH: 17
<212> TYPE: PRT
<213> ORGANISM: Artificial sequence
<220> FEATURE:
<223> OTHER INFORMATION: Synthetic

<400> SEQUENCE: 31

```
Gly Ile Ile Pro Ile Leu Gly Leu Asp Tyr Tyr Ala Gln Lys Phe Gln
1               5                   10                  15

Gly
```

<210> SEQ ID NO 32
<211> LENGTH: 17
<212> TYPE: PRT
<213> ORGANISM: Artificial sequence
<220> FEATURE:
<223> OTHER INFORMATION: Synthetic

<400> SEQUENCE: 32

Gly Ile Ile Pro Val Leu Gly Tyr Ala Tyr Tyr Ala Gln Lys Phe Gln
1               5                   10                  15

Gly

<210> SEQ ID NO 33
<211> LENGTH: 17
<212> TYPE: PRT
<213> ORGANISM: Artificial sequence
<220> FEATURE:
<223> OTHER INFORMATION: Synthetic

<400> SEQUENCE: 33

Gly Ile Ile Pro Ile Leu Gly Tyr Ala Tyr Tyr Ala Gln Lys Phe Gln
1               5                   10                  15

Gly

<210> SEQ ID NO 34
<211> LENGTH: 17
<212> TYPE: PRT
<213> ORGANISM: Artificial sequence
<220> FEATURE:
<223> OTHER INFORMATION: Synthetic

<400> SEQUENCE: 34

Gly Ile Ile Pro Ile Leu Gly Ile Ser Tyr Tyr Ala Gln Lys Phe Gln
1               5                   10                  15

Gly

<210> SEQ ID NO 35
<211> LENGTH: 17
<212> TYPE: PRT
<213> ORGANISM: Artificial sequence
<220> FEATURE:
<223> OTHER INFORMATION: Synthetic

<400> SEQUENCE: 35

Ser Ile Ile Pro Val Ile Gly Tyr Asp Tyr Tyr Ala Gln Lys Phe Gln
1               5                   10                  15

Gly

<210> SEQ ID NO 36
<211> LENGTH: 16
<212> TYPE: PRT
<213> ORGANISM: Artificial sequence
<220> FEATURE:
<223> OTHER INFORMATION: Synthetic

<400> SEQUENCE: 36

Arg Ser Ser Gln Thr Ile Val His Ser Asn Gly Asn Thr Tyr Leu Glu
1               5                   10                  15

<210> SEQ ID NO 37
<211> LENGTH: 7
<212> TYPE: PRT
<213> ORGANISM: Artificial sequence
<220> FEATURE:
<223> OTHER INFORMATION: Synthetic

<400> SEQUENCE: 37

Lys Val Ser Asn Arg Phe Ser
1               5

<210> SEQ ID NO 38
<211> LENGTH: 9

```
<212> TYPE: PRT
<213> ORGANISM: Artificial sequence
<220> FEATURE:
<223> OTHER INFORMATION: Synthetic

<400> SEQUENCE: 38

Phe Gln Gly Ser His Val Pro Pro Thr
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic

<400> SEQUENCE: 39

Asn Tyr Trp Met Asn
1               5

<210> SEQ ID NO 40
<211> LENGTH: 17
<212> TYPE: PRT
<213> ORGANISM: Artificial sequence
<220> FEATURE:
<223> OTHER INFORMATION: Synthetic

<400> SEQUENCE: 40

Met Ile Asp Pro Ser Asp Asn Glu Thr His Tyr Ser Gln Met Phe Lys
1               5                   10                  15

Asp

<210> SEQ ID NO 41
<211> LENGTH: 10
<212> TYPE: PRT
<213> ORGANISM: Artificial sequence
<220> FEATURE:
<223> OTHER INFORMATION: Synthetic

<400> SEQUENCE: 41

Tyr Tyr Gly Asn Phe Gly Trp Phe Val Tyr
1               5                   10

<210> SEQ ID NO 42
<211> LENGTH: 11
<212> TYPE: PRT
<213> ORGANISM: Artificial sequence
<220> FEATURE:
<223> OTHER INFORMATION: Synthetic

<400> SEQUENCE: 42

Lys Ala Ser Gln Asp Val Gly Asp Ala Val Ala
1               5                   10

<210> SEQ ID NO 43
<211> LENGTH: 7
<212> TYPE: PRT
<213> ORGANISM: Artificial sequence
<220> FEATURE:
<223> OTHER INFORMATION: Synthetic

<400> SEQUENCE: 43

Trp Thr Ser Thr Arg His Thr
1               5

<210> SEQ ID NO 44
```

```
<211> LENGTH: 9
<212> TYPE: PRT
<213> ORGANISM: Artificial sequence
<220> FEATURE:
<223> OTHER INFORMATION: Synthetic

<400> SEQUENCE: 44

Gln Gln Tyr Arg Ser Thr Pro Leu Thr
1               5

<210> SEQ ID NO 45
<211> LENGTH: 5
<212> TYPE: PRT
<213> ORGANISM: Artificial sequence
<220> FEATURE:
<223> OTHER INFORMATION: Synthetic

<400> SEQUENCE: 45

Ser Tyr Asn Met Tyr
1               5

<210> SEQ ID NO 46
<211> LENGTH: 17
<212> TYPE: PRT
<213> ORGANISM: Artificial sequence
<220> FEATURE:
<223> OTHER INFORMATION: Synthetic

<400> SEQUENCE: 46

Tyr Ile Asp Pro Tyr Asn Gly Gly Thr Arg His Asn Gln Lys Phe Lys
1               5                   10                  15

Asp

<210> SEQ ID NO 47
<211> LENGTH: 8
<212> TYPE: PRT
<213> ORGANISM: Artificial sequence
<220> FEATURE:
<223> OTHER INFORMATION: Synthetic

<400> SEQUENCE: 47

Gln Asn Tyr Glu Tyr Phe Asp Tyr
1               5

<210> SEQ ID NO 48
<211> LENGTH: 11
<212> TYPE: PRT
<213> ORGANISM: Artificial sequence
<220> FEATURE:
<223> OTHER INFORMATION: Synthetic

<400> SEQUENCE: 48

Lys Ala Ser Gln Asp Val Asn Thr Ala Val Ala
1               5                   10

<210> SEQ ID NO 49
<211> LENGTH: 7
<212> TYPE: PRT
<213> ORGANISM: Artificial sequence
<220> FEATURE:
<223> OTHER INFORMATION: Synthetic

<400> SEQUENCE: 49

Trp Ala Ser Thr Arg His Thr
1               5
```

```
<210> SEQ ID NO 50
<211> LENGTH: 9
<212> TYPE: PRT
<213> ORGANISM: Artificial sequence
<220> FEATURE:
<223> OTHER INFORMATION: Synthetic

<400> SEQUENCE: 50

Gln Gln His Ser Gly Thr Pro Leu Thr
1               5

<210> SEQ ID NO 51
<211> LENGTH: 17
<212> TYPE: PRT
<213> ORGANISM: Artificial sequence
<220> FEATURE:
<223> OTHER INFORMATION: Synthetic

<400> SEQUENCE: 51

Tyr Ile Asp Pro Tyr Asn Gly Gly Thr Ser Tyr Asn Gln Lys Phe Lys
1               5                   10                  15

Gly

<210> SEQ ID NO 52
<211> LENGTH: 8
<212> TYPE: PRT
<213> ORGANISM: Artificial sequence
<220> FEATURE:
<223> OTHER INFORMATION: Synthetic

<400> SEQUENCE: 52

Ala Ala Tyr Phe Tyr Phe Asp Tyr
1               5

<210> SEQ ID NO 53
<211> LENGTH: 11
<212> TYPE: PRT
<213> ORGANISM: Artificial sequence
<220> FEATURE:
<223> OTHER INFORMATION: Synthetic

<400> SEQUENCE: 53

Leu Ala Ser Gln Thr Ile Gly Thr Trp Leu Ala
1               5                   10

<210> SEQ ID NO 54
<211> LENGTH: 7
<212> TYPE: PRT
<213> ORGANISM: Artificial sequence
<220> FEATURE:
<223> OTHER INFORMATION: Synthetic

<400> SEQUENCE: 54

Ala Ala Thr Thr Leu Ala Asp
1               5

<210> SEQ ID NO 55
<211> LENGTH: 9
<212> TYPE: PRT
<213> ORGANISM: Artificial sequence
<220> FEATURE:
<223> OTHER INFORMATION: Synthetic

<400> SEQUENCE: 55

Gln Gln Leu Tyr Ser Thr Pro Leu Thr
1               5
```

<210> SEQ ID NO 56
<211> LENGTH: 5
<212> TYPE: PRT
<213> ORGANISM: Artificial sequence
<220> FEATURE:
<223> OTHER INFORMATION: Synthetic

<400> SEQUENCE: 56

Ser Tyr Val Met His
1               5

<210> SEQ ID NO 57
<211> LENGTH: 17
<212> TYPE: PRT
<213> ORGANISM: Artificial sequence
<220> FEATURE:
<223> OTHER INFORMATION: Synthetic

<400> SEQUENCE: 57

Tyr Ile Asn Pro Tyr Asn Asp Gly Thr Lys Tyr Asn Asp Lys Phe Lys
1               5                   10                  15

Gly

<210> SEQ ID NO 58
<211> LENGTH: 11
<212> TYPE: PRT
<213> ORGANISM: Artificial sequence
<220> FEATURE:
<223> OTHER INFORMATION: Synthetic

<400> SEQUENCE: 58

Gly Ser Asn Tyr Glu Asp Phe Ala Met Asp Tyr
1               5                   10

<210> SEQ ID NO 59
<211> LENGTH: 15
<212> TYPE: PRT
<213> ORGANISM: Artificial sequence
<220> FEATURE:
<223> OTHER INFORMATION: Synthetic

<400> SEQUENCE: 59

Arg Ala Ser Glu Ser Val Asp Ser Tyr Gly Asn Ser Tyr Leu His
1               5                   10                  15

<210> SEQ ID NO 60
<211> LENGTH: 7
<212> TYPE: PRT
<213> ORGANISM: Artificial sequence
<220> FEATURE:
<223> OTHER INFORMATION: Synthetic

<400> SEQUENCE: 60

Leu Ala Ser Asn Leu Glu Ser
1               5

<210> SEQ ID NO 61
<211> LENGTH: 9
<212> TYPE: PRT
<213> ORGANISM: Artificial sequence
<220> FEATURE:
<223> OTHER INFORMATION: Synthetic

<400> SEQUENCE: 61

Gln Gln Asn Asn Glu Asp Pro Trp Thr
1               5

<210> SEQ ID NO 62
<211> LENGTH: 5
<212> TYPE: PRT
<213> ORGANISM: Artificial sequence
<220> FEATURE:
<223> OTHER INFORMATION: Synthetic

<400> SEQUENCE: 62

Thr Phe Pro Ile Glu
1               5

<210> SEQ ID NO 63
<211> LENGTH: 17
<212> TYPE: PRT
<213> ORGANISM: Artificial sequence
<220> FEATURE:
<223> OTHER INFORMATION: Synthetic

<400> SEQUENCE: 63

Asn Phe His Pro Tyr Asn Asp Gln Thr Lys Tyr Asn Glu Glu Phe Lys
1               5                   10                  15

Gly

<210> SEQ ID NO 64
<211> LENGTH: 8
<212> TYPE: PRT
<213> ORGANISM: Artificial sequence
<220> FEATURE:
<223> OTHER INFORMATION: Synthetic

<400> SEQUENCE: 64

Gly Tyr Tyr Tyr Ala Phe Asp Phe
1               5

<210> SEQ ID NO 65
<211> LENGTH: 112
<212> TYPE: PRT
<213> ORGANISM: Artificial sequence
<220> FEATURE:
<223> OTHER INFORMATION: Synthetic

<400> SEQUENCE: 65

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 66
<211> LENGTH: 117
<212> TYPE: PRT
<213> ORGANISM: Artificial sequence
<220> FEATURE:

<223> OTHER INFORMATION: Synthetic

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Ala Val Ser Trp Val Arg Gln Ala Pro Gly Gln Gly Leu Glu Trp Met
        35                  40                  45

Gly Gly Ile Ile Pro Ile Phe Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Leu Ala Asp Val Phe Asp Ile Trp Gly Gln Gly Thr Met
            100                 105                 110

Val Thr Val Ser Ser
        115

<210> SEQ ID NO 67
<211> LENGTH: 112
<212> TYPE: PRT
<213> ORGANISM: Artificial sequence
<220> FEATURE:
<223> OTHER INFORMATION: Synthetic

<400> SEQUENCE: 67

Asp Val Val Met Thr Gln Ser Pro Leu Ser Leu Pro Val Ala Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Leu Glu Ile Lys
            100                 105                 110

<210> SEQ ID NO 68
<211> LENGTH: 117
<212> TYPE: PRT
<213> ORGANISM: Artificial sequence
<220> FEATURE:
<223> OTHER INFORMATION: Synthetic

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ser Ile Ser Trp Val Arg Gln Ala Pro Gly Gln Gly Leu Glu Trp Met
        35                  40                  45

Gly Glu Ile Ile Pro Ile Phe Gly Thr Ala Asp Tyr Ala Gln Lys Phe

```
              50                  55                  60
Gln Gly Arg Val Thr Ile Thr Ala Asp Ile Ser Thr Thr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Trp Ala Asp Ala Phe Asp Ile Trp Gly Gln Gly Thr Met
                100                 105                 110

Val Thr Val Ser Ser
        115

<210> SEQ ID NO 69
<211> LENGTH: 107
<212> TYPE: PRT
<213> ORGANISM: Artificial sequence
<220> FEATURE:
<223> OTHER INFORMATION: Synthetic

<400> SEQUENCE: 69

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Leu Glu Ile Lys
            100                 105

<210> SEQ ID NO 70
<211> LENGTH: 118
<212> TYPE: PRT
<213> ORGANISM: Artificial sequence
<220> FEATURE:
<223> OTHER INFORMATION: Synthetic

<400> SEQUENCE: 70

Glu Val Gln Leu Val Glu Ser Gly Gly Ala Leu Ile Gln Pro Gly Gly
  1               5                  10                  15

Ser Leu Arg Leu Ser Cys Val Ala Ser Gly Phe Thr Ile Ser Gly Asn
                 20                  25                  30

Tyr Met Ser Trp Val Arg Gln Ala Pro Gly Lys Gly Leu Glu Trp Val
             35                  40                  45

Ser Leu Ile Tyr Ser Gly Asp Ser Thr Tyr Tyr Ala Asp Ser Val Lys
 50                  55                  60

Gly Arg Phe Asn Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                 85                  90                  95

Arg Asp Gly Tyr Tyr Val Ser Asp Met Val Val Trp Gly Lys Gly Thr
            100                 105                 110

Thr Val Thr Val Ser Ser
        115
```

```
<210> SEQ ID NO 71
<211> LENGTH: 107
<212> TYPE: PRT
<213> ORGANISM: Artificial sequence
<220> FEATURE:
<223> OTHER INFORMATION: Synthetic

<400> SEQUENCE: 71

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 72
<211> LENGTH: 118
<212> TYPE: PRT
<213> ORGANISM: Artificial sequence
<220> FEATURE:
<223> OTHER INFORMATION: Synthetic

<400> SEQUENCE: 72

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Thr Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 73
<211> LENGTH: 107
<212> TYPE: PRT
<213> ORGANISM: Artificial sequence
<220> FEATURE:
<223> OTHER INFORMATION: Synthetic

<400> SEQUENCE: 73

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
```

```
                    20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
                100                 105

<210> SEQ ID NO 74
<211> LENGTH: 118
<212> TYPE: PRT
<213> ORGANISM: Artificial sequence
<220> FEATURE:
<223> OTHER INFORMATION: Synthetic

<400> SEQUENCE: 74

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
                100                 105                 110

Thr Val Thr Val Ser Ser
        115

<210> SEQ ID NO 75
<211> LENGTH: 107
<212> TYPE: PRT
<213> ORGANISM: Artificial sequence
<220> FEATURE:
<223> OTHER INFORMATION: Synthetic

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95
```

```
Thr Phe Gly Gln Gly Thr Lys Leu Glu Ile Lys
            100                 105
```

```
<210> SEQ ID NO 76
<211> LENGTH: 118
<212> TYPE: PRT
<213> ORGANISM: Artificial sequence
<220> FEATURE:
<223> OTHER INFORMATION: Synthetic

<400> SEQUENCE: 76

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
50                  55                  60

Gly Arg Phe Ala Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115
```

```
<210> SEQ ID NO 77
<211> LENGTH: 112
<212> TYPE: PRT
<213> ORGANISM: Artificial sequence
<220> FEATURE:
<223> OTHER INFORMATION: Synthetic

<400> SEQUENCE: 77

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

```
<210> SEQ ID NO 78
<211> LENGTH: 117
<212> TYPE: PRT
<213> ORGANISM: Artificial sequence
<220> FEATURE:
<223> OTHER INFORMATION: Synthetic

<400> SEQUENCE: 78

Glu Val Gln Leu Val Glu Ser Gly Ala Glu Val Lys Lys Pro Gly Ser
```

```
                1               5                   10                  15
        Ser Val Lys Val Ser Cys Lys Ala Ser Gly Gly Thr Leu Ile Ser His
                        20                  25                  30

Ala Ile Ser Trp Val Arg Gln Val Pro Gly Gln Gly Leu Glu Trp Met
                        35                  40                  45

Gly Gly Ile Ile Pro Ile Phe Gly Ser Ala Asn Tyr Ala Gln Lys Phe
                        50                  55                  60

Gln Gly Arg Val Thr Ile Thr Ala Asp Asp Ser Thr Asn Thr Ala Tyr
        65                  70                  75                  80

Leu Glu Leu Ser Ser Leu Arg Ser Glu Asp Thr Ala Val Tyr Tyr Cys
                        85                  90                  95

Ala Arg Glu Leu Leu Asp Val Phe Asp Ile Trp Gly Gln Gly Thr Met
                        100                 105                 110

Val Thr Val Ser Ser
                        115

<210> SEQ ID NO 79
<211> LENGTH: 112
<212> TYPE: PRT
<213> ORGANISM: Artificial sequence
<220> FEATURE:
<223> OTHER INFORMATION: Synthetic

<400> SEQUENCE: 79

Glu Ile Val Leu Thr Gln Ser Pro Leu Ser Leu Pro Val Thr Pro Gly
        1               5                   10                  15

Glu Pro Ala Ser Ile Ser Cys Arg Ser Ser Gln Ser Leu Leu His Ser
                        20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                        50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Met Gln Ala
                        85                  90                  95

Leu Gln Thr Pro Trp Thr Phe Gly Gln Gly Thr Lys Val Glu Ile Lys
                        100                 105                 110

<210> SEQ ID NO 80
<211> LENGTH: 117
<212> TYPE: PRT
<213> ORGANISM: Artificial sequence
<220> FEATURE:
<223> OTHER INFORMATION: Synthetic

<400> SEQUENCE: 80

Gln Val Gln Leu Val Gln Ser Gly Ala Glu Val Lys Lys Pro Gly Ser
        1               5                   10                  15

Ser Val Lys Val Ser Cys Lys Ala Ser Gly Gly Ile Phe Ser Asn His
                        20                  25                  30

Ala Ile Ser Trp Val Arg Gln Ala Pro Gly Gln Gly Leu Glu Trp Met
                        35                  40                  45

Gly Gly Ile Ile Pro Ile Phe Gly Thr Ala Asn Tyr Ala Gln Lys Phe
                        50                  55                  60

Gln Gly Arg Val Thr Ile Thr Ala Asp Glu Ser Thr Ser Thr Ala Phe
        65                  70                  75                  80
```

```
Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 81
<211> LENGTH: 112
<212> TYPE: PRT
<213> ORGANISM: Artificial sequence
<220> FEATURE:
<223> OTHER INFORMATION: Synthetic

<400> SEQUENCE: 81

Glu Ile Val Leu Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Val Asn Ser Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 82
<211> LENGTH: 117
<212> TYPE: PRT
<213> ORGANISM: Artificial sequence
<220> FEATURE:
<223> OTHER INFORMATION: Synthetic

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 83
<211> LENGTH: 112
<212> TYPE: PRT
<213> ORGANISM: Artificial sequence
```

```
<220> FEATURE:
<223> OTHER INFORMATION: Synthetic

<400> SEQUENCE: 83

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser His Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 84
<211> LENGTH: 117
<212> TYPE: PRT
<213> ORGANISM: Artificial sequence
<220> FEATURE:
<223> OTHER INFORMATION: Synthetic

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 85
<211> LENGTH: 112
<212> TYPE: PRT
<213> ORGANISM: Artificial sequence
<220> FEATURE:
<223> OTHER INFORMATION: Synthetic

<400> SEQUENCE: 85

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

```
Pro Gln Leu Leu Ile Tyr Leu Gly Ala Tyr Thr Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
                100                 105                 110
```

<210> SEQ ID NO 86
<211> LENGTH: 117
<212> TYPE: PRT
<213> ORGANISM: Artificial sequence
<220> FEATURE:
<223> OTHER INFORMATION: Synthetic

<400> SEQUENCE: 86

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
                100                 105                 110

Val Thr Val Ser Ser
            115
```

<210> SEQ ID NO 87
<211> LENGTH: 112
<212> TYPE: PRT
<213> ORGANISM: Artificial sequence
<220> FEATURE:
<223> OTHER INFORMATION: Synthetic

<400> SEQUENCE: 87

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Asn Tyr Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
                100                 105                 110
```

<210> SEQ ID NO 88

<211> LENGTH: 117
<212> TYPE: PRT
<213> ORGANISM: Artificial sequence
<220> FEATURE:
<223> OTHER INFORMATION: Synthetic

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 89
<211> LENGTH: 112
<212> TYPE: PRT
<213> ORGANISM: Artificial sequence
<220> FEATURE:
<223> OTHER INFORMATION: Synthetic

<400> SEQUENCE: 89

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 90
<211> LENGTH: 117
<212> TYPE: PRT
<213> ORGANISM: Artificial sequence
<220> FEATURE:
<223> OTHER INFORMATION: Synthetic

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Gly His
            20                  25                  30

Lys Val Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Phe
 65                  70                  75                  80

Met Glu Leu Ser Ser Leu Arg Ser Glu Asp Thr Ala Val Tyr Tyr Cys
             85                  90                  95

Ala Arg Glu Trp Ala Asp Val Phe Asp Ile Trp Gly Gln Gly Thr Met
            100                 105                 110

Val Thr Val Ser Ser
            115

<210> SEQ ID NO 91
<211> LENGTH: 112
<212> TYPE: PRT
<213> ORGANISM: Artificial sequence
<220> FEATURE:
<223> OTHER INFORMATION: Synthetic

<400> SEQUENCE: 91

Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
             85                  90                  95

Leu Gln Thr Pro Trp Thr Phe Gly Gln Gly Thr Lys Val Glu Ile Lys
            100                 105                 110

<210> SEQ ID NO 92
<211> LENGTH: 117
<212> TYPE: PRT
<213> ORGANISM: Artificial sequence
<220> FEATURE:
<223> OTHER INFORMATION: Synthetic

<400> SEQUENCE: 92

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
            35                  40                  45

Gly Gly Ile Ile Pro Ile Leu Gly Leu Asp Tyr Tyr Ala Gln Lys Phe
 50                  55                  60

Gln Gly Arg Val Thr Ile Thr Ala Asp Glu Ser Thr Ser Thr Ala Phe
 65                  70                  75                  80

Met Glu Leu Ser Ser Leu Arg Ser Glu Asp Thr Ala Val Tyr Tyr Cys
             85                  90                  95

Ala Arg Glu Trp Ala Asp Val Phe Asp Ile Trp Gly Gln Gly Thr Met
            100                 105                 110

<210> SEQ ID NO 93
<211> LENGTH: 112
<212> TYPE: PRT
<213> ORGANISM: Artificial sequence
<220> FEATURE:
<223> OTHER INFORMATION: Synthetic

<400> SEQUENCE: 93

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 94
<211> LENGTH: 117
<212> TYPE: PRT
<213> ORGANISM: Artificial sequence
<220> FEATURE:
<223> OTHER INFORMATION: Synthetic

<400> SEQUENCE: 94

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Val Leu Gly Tyr Ala Tyr Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115
```

<210> SEQ ID NO 95
<211> LENGTH: 112
<212> TYPE: PRT
<213> ORGANISM: Artificial sequence
<220> FEATURE:
<223> OTHER INFORMATION: Synthetic

<400> SEQUENCE: 95

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 96
<211> LENGTH: 117
<212> TYPE: PRT
<213> ORGANISM: Artificial sequence
<220> FEATURE:
<223> OTHER INFORMATION: Synthetic

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Tyr Ala Tyr Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 97
<211> LENGTH: 112
<212> TYPE: PRT
<213> ORGANISM: Artificial sequence
<220> FEATURE:
<223> OTHER INFORMATION: Synthetic

<400> SEQUENCE: 97

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 98
<211> LENGTH: 117
<212> TYPE: PRT
<213> ORGANISM: Artificial sequence
<220> FEATURE:
<223> OTHER INFORMATION: Synthetic

<400> SEQUENCE: 98

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
                20                  25                  30

Ala Ile Ser Trp Val Arg Gln Ala Pro Gly Gln Gly Leu Glu Trp Met
            35                  40                  45

Gly Gly Ile Ile Pro Ile Leu Gly Ile Ser Tyr Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115
```

<210> SEQ ID NO 99
<211> LENGTH: 112
<212> TYPE: PRT
<213> ORGANISM: Artificial sequence
<220> FEATURE:
<223> OTHER INFORMATION: Synthetic

<400> SEQUENCE: 99

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 100
<211> LENGTH: 117
<212> TYPE: PRT
<213> ORGANISM: Artificial sequence
<220> FEATURE:
<223> OTHER INFORMATION: Synthetic

```
<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Ser Ile Ile Pro Val Ile Gly Tyr Asp Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
                100                 105                 110

Val Thr Val Ser Ser
        115

<210> SEQ ID NO 101
<211> LENGTH: 112
<212> TYPE: PRT
<213> ORGANISM: Artificial sequence
<220> FEATURE:
<223> OTHER INFORMATION: Synthetic

<400> SEQUENCE: 101

Asp Ile Phe Met Thr Gln Thr Pro Leu Ser Leu Pro Val Ser Leu Gly
1               5                   10                  15

Asp Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Val Glu Ile Lys
                100                 105                 110

<210> SEQ ID NO 102
<211> LENGTH: 119
<212> TYPE: PRT
<213> ORGANISM: Artificial sequence
<220> FEATURE:
<223> OTHER INFORMATION: Synthetic

<400> SEQUENCE: 102

Glu Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Asn Glu Thr His Tyr Ser Gln Met Phe
    50                  55                  60
```

```
Lys Asp Lys Ala Thr Leu Thr Val Asp Lys Ser Ser Thr Ala Tyr
 65                  70                  75                  80

Met Gln Leu Ile Ser Leu Thr Ser Glu Asp Ser Ala Val Tyr Tyr Cys
                 85                  90                  95

Ala Gly Tyr Tyr Gly Asn Phe Gly Trp Phe Val Tyr Trp Gly Gln Gly
            100                 105                 110

Thr Leu Val Thr Val Ser Ala
        115

<210> SEQ ID NO 103
<211> LENGTH: 107
<212> TYPE: PRT
<213> ORGANISM: Artificial sequence
<220> FEATURE:
<223> OTHER INFORMATION: Synthetic

<400> SEQUENCE: 103

Asp Ile Val Leu Thr Gln Ser Pro Lys Phe Met Ser Thr Ser Val Gly
 1               5                  10                  15

Asp Arg Val Ser Ile Thr Cys Lys Ala Ser Gln Asp Val Gly Asp Ala
            20                  25                  30

Val Ala Trp Tyr Gln Gln Lys Pro Gly Gln Ser Pro Lys Leu Leu Phe
         35                  40                  45

Tyr Trp Thr Ser Thr Arg His Thr Gly Val Pro Asp Arg Phe Thr Gly
 50                  55                  60

Ser Gly Ser Gly Thr Glu Phe Thr Leu Thr Ile Arg Asn Val Gln Ser
 65                  70                  75                  80

Glu Asp Leu Ala Asp Tyr Phe Cys Gln Gln Tyr Arg Ser Thr Pro Leu
                 85                  90                  95

Thr Phe Gly Ser Gly Thr Lys Val Glu Ile Lys
            100                 105

<210> SEQ ID NO 104
<211> LENGTH: 117
<212> TYPE: PRT
<213> ORGANISM: Artificial sequence
<220> FEATURE:
<223> OTHER INFORMATION: Synthetic

<400> SEQUENCE: 104

Glu Val Gln Leu Gln Gln Ser Gly Pro Glu Leu Val Lys Pro Gly Ala
 1               5                  10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
         35                  40                  45

Gly Tyr Ile Asp Pro Tyr Asn Gly Gly Thr Arg His Asn Gln Lys Phe
 50                  55                  60

Lys Asp Lys Ala Thr Leu Thr Val Asp Lys Ser Ser Thr Ala Tyr
 65                  70                  75                  80

Met His Leu Asn Ser Leu Thr Ser Glu Asp Ser Ala Val Tyr Tyr Cys
                 85                  90                  95

Ala Ser Gln Asn Tyr Glu Tyr Phe Asp Tyr Trp Gly Gln Gly Thr Thr
            100                 105                 110

Leu Thr Val Ser Ser
        115
```

-continued

```
<210> SEQ ID NO 105
<211> LENGTH: 107
<212> TYPE: PRT
<213> ORGANISM: Artificial sequence
<220> FEATURE:
<223> OTHER INFORMATION: Synthetic

<400> SEQUENCE: 105

Glu Ile Gln Met Thr Gln Ser Pro Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Ser Gly Thr Pro Leu
                85                  90                  95

Thr Phe Gly Ala Gly Thr Lys Val Glu Ile Lys
            100                 105

<210> SEQ ID NO 106
<211> LENGTH: 117
<212> TYPE: PRT
<213> ORGANISM: Artificial sequence
<220> FEATURE:
<223> OTHER INFORMATION: Synthetic

<400> SEQUENCE: 106

Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Phe Cys
                85                  90                  95

Ala Pro Ala Ala Tyr Phe Tyr Phe Asp Tyr Trp Gly Gln Gly Thr Thr
            100                 105                 110

Leu Thr Val Ser Ser
        115

<210> SEQ ID NO 107
<211> LENGTH: 107
<212> TYPE: PRT
<213> ORGANISM: Artificial sequence
<220> FEATURE:
<223> OTHER INFORMATION: Synthetic

<400> SEQUENCE: 107

Asp Ile Val Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30
```

-continued

Leu Ala Trp Tyr Gln Gln Lys Pro Gly Lys Ser Pro Gln Leu Leu Ile
            35                  40                  45

Tyr Ala Ala Thr Thr Leu Ala Asp Gly Val Pro Ser Arg Phe Ser Gly
        50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Leu
                85                  90                  95

Thr Phe Gly Gly Gly Thr Lys Val Glu Ile Lys
            100                 105

<210> SEQ ID NO 108
<211> LENGTH: 120
<212> TYPE: PRT
<213> ORGANISM: Artificial sequence
<220> FEATURE:
<223> OTHER INFORMATION: Synthetic

<400> SEQUENCE: 108

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Met Lys Gln Lys Pro Gly Gln Gly Leu Glu Trp Ile
        35                  40                  45

Gly Tyr Ile Asn Pro Tyr Asn Asp Gly Thr Lys Tyr Asn Asp Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ser Asn Tyr Glu Asp Phe Ala Met Asp Tyr Arg Gly Gln
            100                 105                 110

Gly Thr Ser Val Thr Val Ser Ser
            115                 120

<210> SEQ ID NO 109
<211> LENGTH: 111
<212> TYPE: PRT
<213> ORGANISM: Artificial sequence
<220> FEATURE:
<223> OTHER INFORMATION: Synthetic

<400> SEQUENCE: 109

Asp Ile Gln Met Thr Gln Ser Pro Ala Ser Leu Thr Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Tyr Leu His Trp Tyr Gln Gln Lys Pro Gly Gln Pro Pro
        35                  40                  45

Gln Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Val Glu Ile Lys

```
                   100                 105                 110

<210> SEQ ID NO 110
<211> LENGTH: 117
<212> TYPE: PRT
<213> ORGANISM: Artificial sequence
<220> FEATURE:
<223> OTHER INFORMATION: Synthetic

<400> SEQUENCE: 110

Glu Val Gln Leu Gln Gln Ser Gly Ala Glu Leu Val Lys Pro Gly Ala
1               5                   10                  15

Ser Val Lys Met Ser Cys Lys Ala Phe Gly Tyr Thr Phe Thr Thr Phe
            20                  25                  30

Pro Ile Glu Trp Met Lys Gln Ser His Gly Lys Ser Leu Glu Trp Ile
        35                  40                  45

Gly Asn Phe His Pro Tyr Asn Asp Gln Thr Lys Tyr Asn Glu Glu Phe
    50                  55                  60

Lys Gly Arg Ala Lys Leu Thr Ile Asp Arg Ser Ser Thr Val Tyr
65                  70                  75                  80

Leu Glu Leu Gly Arg Leu Thr Ser Asp Asp Ser Ala Val Tyr Tyr Cys
                85                  90                  95

Ala Arg Gly Tyr Tyr Tyr Ala Phe Asp Phe Trp Gly Gln Gly Thr Thr
            100                 105                 110

Leu Thr Val Ser Ser
        115

<210> SEQ ID NO 111
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: S, V, A or N
<220> FEATURE:
<221> NAME/KEY: MISC_FEATURE
<222> LOCATION: (4)..(4)
<223> OTHER INFORMATION: N, H, or Y
<220> FEATURE:
<221> NAME/KEY: MISC_FEATURE
<222> LOCATION: (5)..(5)
<223> OTHER INFORMATION: R, S, or T
<220> FEATURE:
<221> NAME/KEY: MISC_FEATURE
<222> LOCATION: (6)..(6)
<223> OTHER INFORMATION: A, V, or D

<400> SEQUENCE: 111

Leu Gly Xaa Xaa Xaa Xaa Ser
1               5

<210> SEQ ID NO 112
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S, N, or G
<220> FEATURE:
<221> NAME/KEY: MISC_FEATURE
<222> LOCATION: (2)..(2)
```

```
<223> OTHER INFORMATION: Y or H
<220> FEATURE:
<221> NAME/KEY: MISC_FEATURE
<222> LOCATION: (3)..(3)
<223> OTHER INFORMATION: A, S, or K
<220> FEATURE:
<221> NAME/KEY: MISC_FEATURE
<222> LOCATION: (4)..(4)
<223> OTHER INFORMATION: V or I

<400> SEQUENCE: 112

Xaa Xaa Xaa Xaa Ser
1               5

<210> SEQ ID NO 113
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: G, E, or S
<220> FEATURE:
<221> NAME/KEY: MISC_FEATURE
<222> LOCATION: (5)..(5)
<223> OTHER INFORMATION: I or V
<220> FEATURE:
<221> NAME/KEY: MISC_FEATURE
<222> LOCATION: (6)..(6)
<223> OTHER INFORMATION: F, L, or I
<220> FEATURE:
<221> NAME/KEY: MISC_FEATURE
<222> LOCATION: (8)..(8)
<223> OTHER INFORMATION: T, S, L, Y, or I
<220> FEATURE:
<221> NAME/KEY: MISC_FEATURE
<222> LOCATION: (9)..(9)
<223> OTHER INFORMATION: A, D, or S
<220> FEATURE:
<221> NAME/KEY: MISC_FEATURE
<222> LOCATION: (10)..(10)
<223> OTHER INFORMATION: D, N, or Y

<400> SEQUENCE: 113

Xaa Ile Ile Pro Xaa Xaa Gly Xaa Xaa Xaa Tyr Ala Gln Lys Phe Gln
1               5                   10                  15

Gly

<210> SEQ ID NO 114
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: E or T
<220> FEATURE:
<221> NAME/KEY: MISC_FEATURE
<222> LOCATION: (2)..(2)
<223> OTHER INFORMATION: L or W
<220> FEATURE:
<221> NAME/KEY: MISC_FEATURE
<222> LOCATION: (3)..(3)
<223> OTHER INFORMATION: A or L
<220> FEATURE:
<221> NAME/KEY: MISC_FEATURE
<222> LOCATION: (5)..(5)
<223> OTHER INFORMATION: V or A

<400> SEQUENCE: 114
```

```
Xaa Xaa Xaa Asp Xaa Phe Asp Ile
1               5

<210> SEQ ID NO 115
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S or N
<220> FEATURE:
<221> NAME/KEY: MISC_FEATURE
<222> LOCATION: (2)..(2)
<223> OTHER INFORMATION: Y or H
<220> FEATURE:
<221> NAME/KEY: MISC_FEATURE
<222> LOCATION: (3)..(3)
<223> OTHER INFORMATION: A or S
<220> FEATURE:
<221> NAME/KEY: MISC_FEATURE
<222> LOCATION: (4)..(4)
<223> OTHER INFORMATION: V or I

<400> SEQUENCE: 115

Xaa Xaa Xaa Xaa Ser
1               5

<210> SEQ ID NO 116
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: G or E
<220> FEATURE:
<221> NAME/KEY: MISC_FEATURE
<222> LOCATION: (8)..(8)
<223> OTHER INFORMATION: T or S
<220> FEATURE:
<221> NAME/KEY: MISC_FEATURE
<222> LOCATION: (10)..(10)
<223> OTHER INFORMATION: D or N

<400> SEQUENCE: 116

Xaa Ile Ile Pro Ile Phe Gly Xaa Ala Xaa Tyr Ala Gln Lys Phe Gln
1               5                   10                  15

Gly

<210> SEQ ID NO 117
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: E or T
<220> FEATURE:
<221> NAME/KEY: MISC_FEATURE
<222> LOCATION: (2)..(2)
<223> OTHER INFORMATION: L or W
<220> FEATURE:
<221> NAME/KEY: MISC_FEATURE
<222> LOCATION: (3)..(3)
<223> OTHER INFORMATION: A or L
```

```
<220> FEATURE:
<221> NAME/KEY: MISC_FEATURE
<222> LOCATION: (5)..(5)
<223> OTHER INFORMATION: V or A

<400> SEQUENCE: 117

Xaa Xaa Xaa Asp Xaa Phe Asp Ile
1               5

<210> SEQ ID NO 118
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N or G
<220> FEATURE:
<221> NAME/KEY: MISC_FEATURE
<222> LOCATION: (3)..(3)
<223> OTHER INFORMATION: A or K
<220> FEATURE:
<221> NAME/KEY: MISC_FEATURE
<222> LOCATION: (4)..(4)
<223> OTHER INFORMATION: V or I

<400> SEQUENCE: 118

Xaa His Xaa Xaa Ser
1               5

<210> SEQ ID NO 119
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: G or S
<220> FEATURE:
<221> NAME/KEY: MISC_FEATURE
<222> LOCATION: (5)..(5)
<223> OTHER INFORMATION: I or V
<220> FEATURE:
<221> NAME/KEY: MISC_FEATURE
<222> LOCATION: (6)..(6)
<223> OTHER INFORMATION: F, L, or I
<220> FEATURE:
<221> NAME/KEY: MISC_FEATURE
<222> LOCATION: (8)..(8)
<223> OTHER INFORMATION: T, L, Y or I
<220> FEATURE:
<221> NAME/KEY: MISC_FEATURE
<222> LOCATION: (9)..(9)
<223> OTHER INFORMATION: A, D, or S
<220> FEATURE:
<221> NAME/KEY: MISC_FEATURE
<222> LOCATION: (10)..(10)
<223> OTHER INFORMATION: N or Y

<400> SEQUENCE: 119

Xaa Ile Ile Pro Xaa Xaa Gly Xaa Xaa Xaa Tyr Ala Gln Lys Phe Gln
1               5                   10                  15

Gly

<210> SEQ ID NO 120
<211> LENGTH: 106
<212> TYPE: PRT
<213> ORGANISM: Artificial sequence
```

<220> FEATURE:
<223> OTHER INFORMATION: Synthetic

<400> SEQUENCE: 120

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Cys Thr Lys Ser Phe Asn Arg Gly Glu Cys
            100                 105

<210> SEQ ID NO 121
<211> LENGTH: 330
<212> TYPE: PRT
<213> ORGANISM: Artificial sequence
<220> FEATURE:
<223> OTHER INFORMATION: Synthetic

<400> SEQUENCE: 121

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu

```
                225                 230                 235                 240
Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 122
<211> LENGTH: 119
<212> TYPE: PRT
<213> ORGANISM: Homo sapiens

<400> SEQUENCE: 122

Met Asp Pro Asn Phe Trp Leu Gln Val Gln Glu Ser Val Thr Val Gln
1               5                   10                  15

Glu Gly Leu Cys Val Leu Val Pro Cys Thr Phe Phe His Pro Ile Pro
                20                  25                  30

Tyr Tyr Asp Lys Asn Ser Pro Val His Gly Tyr Trp Phe Arg Glu Gly
            35                  40                  45

Ala Ile Ile Ser Gly Asp Ser Pro Val Ala Thr Asn Lys Leu Asp Gln
        50                  55                  60

Glu Val Gln Glu Glu Thr Gln Gly Arg Phe Arg Leu Leu Gly Asp Pro
65                  70                  75                  80

Ser Arg Asn Asn Cys Ser Leu Ser Ile Val Asp Ala Arg Arg Arg Asp
                85                  90                  95

Asn Gly Ser Tyr Phe Phe Arg Met Glu Arg Gly Ser Thr Lys Tyr Ser
            100                 105                 110

Tyr Lys Ser Pro Gln Leu Ser
        115

<210> SEQ ID NO 123
<211> LENGTH: 119
<212> TYPE: PRT
<213> ORGANISM: Homo sapiens

<400> SEQUENCE: 123

Met Asp Pro Asn Phe Trp Leu Gln Val Gln Glu Ser Val Thr Val Gln
1               5                   10                  15

Glu Gly Leu Cys Val Leu Val Pro Cys Thr Phe Phe His Pro Ile Pro
                20                  25                  30

Tyr Tyr Asp Lys Asn Ser Pro Val His Gly Tyr Trp Phe Arg Glu Gly
            35                  40                  45

Ala Ile Ile Ser Arg Asp Ser Pro Val Ala Thr Asn Lys Leu Asp Gln
        50                  55                  60
```

```
Glu Val Gln Glu Glu Thr Gln Gly Arg Phe Arg Leu Leu Gly Asp Pro
 65                  70                  75                  80

Ser Arg Asn Asn Cys Ser Leu Ser Ile Val Asp Ala Arg Arg Arg Asp
                 85                  90                  95

Asn Gly Ser Tyr Phe Phe Arg Met Glu Arg Gly Ser Thr Lys Tyr Ser
                100                 105                 110

Tyr Lys Ser Pro Gln Leu Ser
            115

<210> SEQ ID NO 124
<211> LENGTH: 10
<212> TYPE: PRT
<213> ORGANISM: Artificial Sequence
<220> FEATURE:
<223> OTHER INFORMATION: C-terminal Flag

<400> SEQUENCE: 124

Arg Ala Asp Tyr Lys Asp Asp Asp Asp Lys
 1               5                  10
```